(12) United States Patent
Altman et al.

(10) Patent No.: US 11,702,430 B2
(45) Date of Patent: Jul. 18, 2023

(54) AZA-BENZOTHIOPHENE COMPOUNDS AS STING AGONISTS

(71) Applicants: Merck Sharp & Dohme LLC, Rahway, NJ (US); Michael D. Altman, Needham, MA (US); Brandon D. Cash, Stoughton, MA (US); Jared N. Cumming, Winchester, MA (US); Duane E. DeMong, Hanover, MA (US); Andrew M. Haidle, Somerville, MA (US); James P. Jewell, Newton, MA (US); Matthew A. Larsen, Dedham, MA (US); Min Lu, Brookline, MA (US); Ryan D. Otte, Natick, MA (US); Brandon M. Taoka, San Francisco, CA (US); Benjamin Wesley Trotter, Medfield, MA (US); Quang T. Truong, Morganville, NJ (US)

(72) Inventors: Michael D. Altman, Needham, MA (US); Brandon D. Cash, Stoughton, MA (US); Jared N. Cumming, Winchester, MA (US); Duane E. DeMong, Hanover, MA (US); Andrew M. Haidle, Somerville, MA (US); James P. Jewell, Newton, MA (US); Matthew A. Larsen, Dedham, MA (US); Min Lu, Brookline, MA (US); Ryan D. Otte, Natick, MA (US); Brandon M. Taoka, San Francisco, CA (US); Benjamin Wesley Trotter, Medfield, MA (US); Quang T. Truong, Morganville, NJ (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 40 days.

(21) Appl. No.: 17/040,192

(22) PCT Filed: Mar. 28, 2019

(86) PCT No.: PCT/US2019/024455
§ 371 (c)(1),
(2) Date: Sep. 22, 2020

(87) PCT Pub. No.: WO2019/195063
PCT Pub. Date: Oct. 10, 2019

(65) Prior Publication Data
US 2021/0009608 A1    Jan. 14, 2021

Related U.S. Application Data

(60) Provisional application No. 62/651,968, filed on Apr. 3, 2018.

(51) Int. Cl.
*C07D 513/04* (2006.01)
*C07D 495/04* (2006.01)
(Continued)

(52) U.S. Cl.
CPC ............ *C07D 513/04* (2013.01); *A61P 37/04* (2018.01); *C07D 495/04* (2013.01)

(58) Field of Classification Search
CPC .. C07D 513/04; C07D 495/04; C07D 277/64; A61P 37/04; A61P 35/00
See application file for complete search history.

(56) References Cited

U.S. PATENT DOCUMENTS 4,299,769 A    11/1981 McEvoy et al.
4,342,689 A    8/1982 McEvoy et al.
(Continued)

FOREIGN PATENT DOCUMENTS

EP    0146243 A1    6/1985
EP    0350990 A1    1/1990
(Continued)

OTHER PUBLICATIONS

RN3751-73-3, registry database compound, 1984.*
(Continued)

*Primary Examiner* — Sun Jae Yoo
(74) *Attorney, Agent, or Firm* — Julie M. Lake; Catherine D. Fitch

(57) ABSTRACT

Compounds of general formula (I), and their pharmaceutically acceptable salts, wherein $R^1$, $R^2$, $R^3$, $R^5$, $R^6$, $R^8$, $R^9$, A, $X^1$, $X^2$, and $X^3$ are defined herein, that may be useful as inductors of type I interferon production, specifically as STING active agents, are provided. Also provided are compositions comprising such compounds, processes for the synthesis of such compounds, and to uses of such compounds, including administration of such compounds to induce immune response, to induce STING-dependent type I interferon production, and/or to treat a cell proliferation disorder, such as cancer.

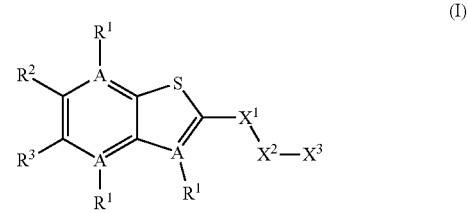

(I)

21 Claims, No Drawings

Specification includes a Sequence Listing.

(51) Int. Cl.
  *C07D 277/64* (2006.01)
  *A61P 37/04* (2006.01)
  *A61P 35/00* (2006.01)

(56) References Cited

U.S. PATENT DOCUMENTS

| | | |
|---|---|---|
| 4,342,690 A | 8/1982 | McEvoy et al. |
| 4,342,691 A | 8/1982 | McEvoy et al. |
| 4,952,571 A | 8/1990 | Redpath et al. |
| 5,569,655 A | 10/1996 | Dority, Jr. et al. |
| 6,262,055 B1 | 7/2001 | Young et al. |
| 7,288,567 B2 | 10/2007 | Delorme et al. |
| 7,488,802 B2 | 2/2009 | Collins et al. |
| 7,521,051 B2 | 4/2009 | Collins et al. |
| 7,595,048 B2 | 9/2009 | Honjo et al. |
| 8,008,449 B2 | 8/2011 | Korman et al. |
| 8,168,757 B2 | 5/2012 | Finnefroch et al. |
| 8,343,967 B2 | 1/2013 | Ding et al. |
| 8,354,509 B2 | 1/2013 | Carven et al. |
| 8,383,796 B2 | 2/2013 | Korman et al. |
| 8,664,255 B2 | 3/2014 | Freundlich et al. |
| 9,439,962 B2 | 9/2016 | Honjo et al. |
| 9,724,408 B2 | 8/2017 | Dubensky, Jr. et al. |
| 10,414,747 B2 | 9/2019 | Altman et al. |
| 2002/0115826 A1 | 8/2002 | Delorme et al. |
| 2003/0060461 A1 | 3/2003 | Kodama et al. |
| 2006/0040887 A1 | 2/2006 | Karaolls |
| 2006/0194821 A1 | 8/2006 | Lansbury et al. |
| 2008/0025979 A1 | 1/2008 | Honjo et al. |
| 2008/0286296 A1 | 11/2008 | Ebensen et al. |
| 2009/0181971 A1 | 7/2009 | Delorme et al. |
| 2010/0113477 A1 | 5/2010 | Freundlich et al. |
| 2011/0271358 A1 | 11/2011 | Freeman et al. |
| 2014/0017444 A1 | 1/2014 | Shimizu et al. |
| 2014/0206640 A1 | 7/2014 | Girijavallabhan et al. |
| 2014/0329889 A1 | 11/2014 | Vance et al. |
| 2014/0341976 A1 | 11/2014 | Dubensky, Jr. et al. |
| 2015/0056224 A1 | 2/2015 | Dubensky, Jr. et al. |
| 2015/0158886 A1 | 6/2015 | Jones et al. |
| 2016/0287698 A1 | 10/2016 | Yan et al. |
| 2016/0362441 A1 | 12/2016 | Vernejoul et al. |
| 2017/0050967 A1 | 2/2017 | Burai et al. |
| 2017/0146519 A1 | 5/2017 | DeFilippis et al. |
| 2017/0158724 A1 | 6/2017 | Adams et al. |
| 2018/0093964 A1 | 4/2018 | Altman et al. |

FOREIGN PATENT DOCUMENTS

| | | |
|---|---|---|
| EP | 0350990 B1 | 9/1995 |
| EP | 3135290 A1 | 1/2018 |
| GB | 532822 | 1/1941 |
| WO | 1994008962 A1 | 4/1994 |
| WO | 199962897 A1 | 12/1999 |
| WO | 2001002369 A2 | 1/2001 |
| WO | 2001002369 A3 | 1/2001 |
| WO | 2001070675 A2 | 9/2001 |
| WO | 2002010192 A2 | 2/2002 |
| WO | 2002068470 A2 | 9/2002 |
| WO | 2004004771 A1 | 1/2004 |
| WO | 2004056875 A1 | 7/2004 |
| WO | 2004072286 A1 | 8/2004 |
| WO | 2005020917 A2 | 3/2005 |
| WO | 2009028727 A1 | 3/2009 |
| WO | 2010027827 A2 | 3/2010 |
| WO | 2010047774 A2 | 4/2010 |
| WO | 2010077634 A1 | 7/2010 |
| WO | 2011066342 A2 | 6/2011 |
| WO | 2012068702 A1 | 5/2012 |
| WO | 2013019906 A1 | 2/2013 |
| WO | 2013185052 A1 | 12/2013 |
| WO | 2014093936 A1 | 6/2014 |
| WO | 2014099824 A1 | 6/2014 |
| WO | 2014099941 A1 | 6/2014 |
| WO | 2014139388 A1 | 9/2014 |
| WO | 2014179335 A1 | 11/2014 |
| WO | 2014179760 A1 | 11/2014 |
| WO | 2014189805 A1 | 11/2014 |
| WO | 2014189806 A1 | 11/2014 |
| WO | 2015017652 A1 | 2/2015 |
| WO | 2015074145 A1 | 5/2015 |
| WO | 2015077354 A1 | 5/2015 |
| WO | 2015148746 A1 | 10/2015 |
| WO | 2015161137 A1 | 10/2015 |
| WO | 2015185565 A1 | 12/2015 |
| WO | 2015189117 A1 | 12/2015 |
| WO | 2016096174 A1 | 6/2016 |
| WO | 2016096577 A1 | 6/2016 |
| WO | 2016100261 A2 | 6/2016 |
| WO | 2016120305 A1 | 8/2016 |
| WO | 2016145102 A1 | 9/2016 |
| WO | 2017011622 A1 | 1/2017 |
| WO | 2017011920 A1 | 1/2017 |
| WO | 2017027645 A1 | 2/2017 |
| WO | 2017027646 A1 | 2/2017 |
| WO | 2017075477 A1 | 5/2017 |
| WO | 2017093933 A1 | 6/2017 |
| WO | 2017100305 A2 | 6/2017 |
| WO | 2017123657 A1 | 7/2017 |
| WO | 2017123669 A1 | 7/2017 |
| WO | 2017161349 A1 | 9/2017 |
| WO | 2017175147 A1 | 10/2017 |
| WO | 2017175156 A1 | 10/2017 |
| WO | 2017216726 A1 | 12/2017 |
| WO | 2018009466 A1 | 1/2018 |
| WO | 2018067423 A1 | 4/2018 |

OTHER PUBLICATIONS

RN381711-20-2, registry database compound, 2002.*
RN211067-64-4, registry database compound, 2017.*
RN676165-51-8, registry database compound, 2004.*
English language translation of Markert, Jurgen et al., Darstellung von 1,2-Benzisothiazolen und einige Folgereaktionen, Liebigs Ann. Chem., 1980, 768-778, 5.
Cuevas-Hernandez, Roberto et al., Fluorine-containing benzothiazole as a novel trypanocidal agent: design, in silico study, synthesis and activity evaluation, Medicinal Chemistry Research, 2016, 211-224, 25.
Database Registry [Online] Chemical Abstracts Service, Columbus, Ohio, US; Aug. 2, 2017, Aurora Fine Chemicals: "2-Benzothiazolepropanoic acid, 5-amino-6-fluoro-, methyl ester", XP055862115, retrieved from STN Database accession No. 2108128-16-9, 1 page.
Ablasser et al., Cell intrinsic immunity spreads to bystander cells via the intercellular transfer of cGAMP, Nature, Nov. 28, 2013, 530-546, 503.
Ablasser et al., cGAS produces a 2'-5'-linked cyclic dinucleotide second messenger that activates STING, Nature, Jun. 20, 2013, 380-385, 498.
Ausmees et al., Genetic Data Indicate that Proteins Containing the GGDEF Domain Possess Diguanylate Cyclase Activity, FEMS Microbiology, 2001, 163-167, Letters 204.
Berge, S.M., et al.,, "Pharmaceutical Salts", J. Pharm. Sci, 1977, pp. 1-19, vol. 66, No. 1.
Bhattacharjee et al, Synthesis of heterocyclic steroids-III: An unsuccessful attempt at the Synthesis of B-Nor-6-thiaequilenin through 3-cyano-7-methoxy-4-oxo-1,2,3,4-Tetrahydrodibenzothiophene, Tetrahedron, 1960, 215-222, 10.
Bookser et al., High-Throughput Five Minute Microwave Accelerated Glycosylation Approach to the Synthesis of Nucleoside Libraries, JOC Article, 2007, 173-179, 72.
Bruno et al., N-Substituted 2-aminobiphenylpalladium Methanesulfonate Precatalysts and Their Use in C—C and C—N Cross Couplings, The Journal of Organic Chamistry, 2014, 4161-4166, 79.
Burdette, Dara L., STING and the innate immune response to nucleic acids in the cytosol, Nature Immunology, Jan. 2013, 19-26, 14(1).
Burdette, Dara L., STING is a direct innate immune sensor of cyclic di-GMP, Nature, Oct. 27, 2011, 515-519, 478.

(56) References Cited

OTHER PUBLICATIONS

Burtner, et al., Synthetic Choleretics. I. Naphthol Derivatives, Journal of the American Chemical Society, 1951, 897-900, vol. 73.
Cagniant, et al., Condensed sulfur heterocycles. III. 1,2,3,4-Tetrahydrodibenzothiophene and, Bulletin de la Societe Chimique de France, 1952, 336-343.
Cagniant, et al., Condensed sulfur heterocycles. IV. Condensation of thianaphthene with glutaric anhydride and the, Bulletin de la Societe Chimique de France, 1952, 629-633.
Cagniant, et al., Condensed sulfur heterocycles. XIX. Synthesis of some ω-thionaphthenylalkanoic acids, Bulletin de la Societe Chimique de France, 1962, 576-581.
Child, et al., A New Non-steroidal Anti-Inflammatory Analgesic: y-Oxo.(1,1'-biphenyl)-4-butanoic Acid (Fenbufen), Arzneimittel-Forschung, 1980, 695-702, vol. 30; Issue 4A.
Dande et al., Improving RNA Interference in Mammalian Cells by 4'-Thio-Modified Small Interfering RNA (siRNA): Effect on siRNA Activity and Nuclease Stability When Used in Combination with 2'-O-Alkyl Modifications, Journal of Medicinal Chemistry, 2006, 1624-1634, 49(5).
Diner et al., The Innate Immune DNA Sensor cGAS Produces a Noncanonical Cyclic Dinucleotide that Activates Human STING, 3 Cell Reports, Cell Reports, 2013, 1355-1361, 3.
Downey et al., DMXAA Causes Tumor Site-Specific Vascular Disruption in Murine Non-Small Molecule Lung Cancer, and Like the Endogenous Non-Canonical Cyclic Dinucleotide STING Agonist, 2'3'-cGAMP, Induces M2 Macrophage Repolarization, PLoS One, 2014, 1-14, 9-6-e99988.
Ertem et al., Synthesis of RNA oligomers on heterogeneous templates, Nature, 1996, 238-240, 379-18.
Fagundes et al., Building unique bonds to fight misplaced DNA, Cell Research, 2013, 1065-1066, 2-9.
Fu, Juan, et al., STING agonist formulated cancer vaccines can cure established tumors resistant to PD-1 blockade, Science Translational Medicine, 2015, 1-13, 7.
Gadthula et al., Synthesis and Anti-HIV Activity of β-D-3'-Azido-2',3'-unsaturated Nucleosides and β-D-3'-Azido-3'deoxyribofuranosylnucleosides, Nucleoside, Nucleotides, Nucleic Acids, 2005, 1707-1727, 24.
Gao et al., Cyclic [G(2',5')pA(3',5")p] Is the Metazoan Second Messenger Produced by DNA-Activated Cyclic GMP-AMP Synthase, Cell, 2013, 1094-1107, 153.
Gao et al., Structure-Function Ananlysis of STING Activation by c[G(2',5')pA(3',5')p] and Targeting by Antiviral DMXAA, Cell, 2013, 748-762, 154.
Goerlitzer, et al., 1,3-Dicarbonyl Compounds. XIV: 4-Oxo-4H-[1]benzofuro[3,2-b]pyrans, Archiv der Pharmazie, 1980, 385-398, vol. 313; Issue 5.
Gopinath et al., As many as six tandem reactions in one step! Unprecendented formation of highly functionalized benzothiophenes, Chemical Communication, Jul. 17, 2009, 7131-7133, vol. 46.
Gopinath, et al., Highly chemoselective Esterification Reactions and Boc/THP/TBDMS Discriminating Deprotections UnderSamarium(III) Catalysis, Organic Letters, 2011, 1932-1935, vol. 13, Issue No. 8.
Gosselin et al., Systematic Synthesis and Biological Evaluation of α- and β-D-lyxofuranosyl Nucleosides of the Five Naturally Occurring Nucleic Acid Bases, J. Med. Chem, 1987, 982-991, 30.
Gould, Salt Selections for Basic Drugs, Intl. J. Pharmaceutics, 1986, pp. 201-217, vol. 33.
Hornfeldt, et al., Unsaturted y-thiolactones II*. The Structures of 3-and 4-Methyl-2-thienols, Acta chem. Scand., 1962, 789-791, vol. 16; Issue No. 2.
Ikeuchi et al., Practical synthesis of natural plant-growth regulator 2-azahypoxanthine, its derivatives, and biotin-labeled probes, Organic & Biomolecular Chemistry, 2014, 3813, 12(23).
Joshi et al., Selectivity of montmorillonite catalyzed prebiotic reactions of D, L-nucleotides, Orig Life Evol Biosph, 2007, 3-26, 37-3.

Kim et al., A Convenient and Versatile Syntheses of 2' (and 3') amino (and azido)-2'(and 3') deoxyadenosine as Diverse Synthetic Precursors of Cyclic Adenosine Diphosphate Ribose (cADPR), Bull. Korean Chem. Soc., 2004, 243, 25-2.
Kobayashi et al., Bacterial c-di-GMP Affects Hematopoietic Stem/Progenitors and their Niches through STING, Cell Reports, 2015, 71-84, 11.
Kranzusch et al., Structure-Guided Reporgramming of Human cGAS Dinucleotide Linkage Specificity, Cell Inc., Elsevier Inc., 2014, 1011-1021, 158.
Kudo, et al., Synthesis of Monoamino and Monohydroxydibenzothiophenes, J. Heterocyclic Chem., 1985, 215218, vol. 22.
Li et al., Cyclic GMP-AMP Synthase is Activated by Double-Stranded DNA-Induced Oligomerization, Immunity, 2013, 1019-1031, 39.
Li et al., Hydrolysis of 2'3'-cGAMP by ENPPI and Design of Nonhydrolyzable Analogs, 10 Nature Chemical Biology 1043 (Dec. 2014); Li et al., Hydrolysis of 2'3'-cGAMP by ENPPI and Design of Nonhydrolyzable Analogs: ERRATUM, Nature Chemical Biology, 2014, 1043, 10.
Liu et al., Activated STING in a Vascular and Pulmonary Syndrome, The New England Journal of Medicine, 2015, 507, 371-6.
Liu et al., Hepatitis B Virus Polymerase Disrupts K63-Linked Ubiquitination of STING to Block Inate Cytosolic DNA-Sensing Pathways, Journal of Virology, 2015, 2287, 89-4.
Lolicato et al., Cyclic Dinucleotides Bind the C-Linker of HCN4 to Control Channel cGAMP Responsiveness, 10 Nature Chemical Biology 457 (Jun. 2014); Lolicato et al., Cyclic Dinucleotides Bind the C-Linker of HCN4 to Control Channel cGAMP Responsiveness, Nature Chemical Biology, 2014, 457, 10.
Markert, Jurgen et al., Darstellung von 1,2-Benzisothiazolen und einige Folgereaktionen, Liebigs Ann. Chem., 1980, 768-778, 5.
Mikhailov et al., Conformational Peculiarities of 5'-C-methylnucleosides, Bioorganicheskaya Khimiya, 1989, 969-975, 15(7).
Minakawa et al., Nucleosides and nucleotides. 116. Convenient syntheses of 3-deazaadenosine, 3-deazaguanosine, and 3-deazainosine via ring closure of 5-ethynyl-1-B-D-ribofuranosylimidazole-4-carboxamide or—carbonitrile, Tetrahedron, 1993, 557-570, 49(3).
Minakawa et al., Nucleosides and Nucleotides. 143. Synthesis of 5-Amino-4-imidazolecarboxamide (AICA) Deoxyribosides from Deoxyinosines and Their Conversion into 3-Deazapurine Derivatives, Chemical & Pharmaceutical Bulletin, 1996, 288-295, 44(2).
Mlochowski, et al., A Simple Route to Benzo[b]thiophenes: Sulfanylation-acylation of C—H Acids With 2-(Chlorosulfanyl)benzoyl Chloride, Phosphorus, Sulfur, and Silicon, 2009, 1115-1123, vol. 184; Issue 5.
O'Neill et al., Sensing the Dark Side of DNA, Sceince, 2013, 763, 339.
Ora et al., Hydrolytic reactions of cyclic bis(3'-5') diadenylic acid (c-di-AMP), J. Phys. Org. Chem, 2013, 218-225, 26.
Panne et al., Cytosolic DNA sensing unraveled, Nature Chemical Biology, 2013, 533, 9.
Patil et al., 4-aza-7,9-dideazaadenosine, a new cytotoxic synthetic C-nucleoside analogue of adenosine, Tetrahedron Letters, 1994, 5339-5342, 35(30).
Puech et al., Synthesis of 9-(3-deoxy- and 2,3-dideoxy-3-fluoro-β-D-xylofuranosyl)guanines as potential antiviral agents, Tetrahedron Letters, 1989, 3171-3174, 30-24.
Ramesh et al., A convenient synthesis of 1-(β-D-ribofuranosyl)imidazo[4,5-d]pyridazin-4(5H)-one (2-aza-3-deazainosine) and its 2'-deoxy counterpart by ring closure of imidazole nucleosides, Journal of the Chemical Society, Perkin Transaction 1, 1989, 1769-1774, 10.
Roembke et al., A cyclic dinucleotide contianing 2-aminopurine is a general fluorescent sensor for c-di-GMP and 3'-3'-cGAMP, Molecular BioSystems, 2014, 1568-1575, 10.
Sali, et al., Characterization of a Novel Human-Specific STING Agonist that Elicits Antiviral Activity Against Emerging Alphaviruses, PLoS Pathogens, 2015, 1-30.
Sheridan, Cormac, Drug Developers Switch Gears to Inhibit STING, Nature Biotechnology, Mar. 4, 2019, 199-208, 37.

(56) References Cited

OTHER PUBLICATIONS

Shi, Heping, et al., Molecular basis for the specific recognition of the metazoan cyclic GMP-AMP by the innate immune adaptor protein STING, PNAS, 2015, 8947-8952, vol. 112/No. 29.

Simm et al., Phenotypic Convergence Mediated by GGDEF-Domain-Containing Proteins, Journal of Bacteriology, 2005, 6816-6823, 187(19).

Stahl et al., Aminoquinazoline Compounds as A2A Antagonist, Handbook of Pharmaceutical Salts Properties, Selection, and Use, 2002, 330-331.

Sun et al., Cyclic GMP-AMP Synthase Is a Cytosolic DNA Sensor That Activates the Type I Interferon Pathway, Science, 2013, 786, 339.

Tang et al., Single Amino Acid change in STING Leads to Constitutive Active Signaling, PLoS One, 2015, 1-10, (10)3.

Tosolini et al., Human Monocyte Recognition of Adenosine-Based Cyclic Dinucleotides Unveils the A2a G∞s Protein-Coupled Receptor Tonic Inhibition of Mitochondrially Induced Cell Death, Molecular and Cellular Biology, 2015, 479-495, 35-2.

Urata et al., Regio- and Diastereo-Selectivity of Montmorillonite-Catalyzed Oligomerization of Racemic Adenosine 5'-Phosphorimidazolide, Nucleosides, Nucleotides and Nucleic Acids, Nucleosides, Nucleotides and Nucleic Acids, 2008, 421-430, 27.

Wang et al., Synthesis and Biological Activity of 5-Fluorotubercidin, Nucleosides, Nucleotides and Nucleic Acids, 2004, 161-170, 23(1).

Wu et al., Cyclic GMP-AMP Is an Endogenous Second Messenger in Innate Immune Signaling by Cytosolic DNA, Science 826, 2013, 826-830, 339.

Yi, Guanghui et al., Single Nucleotide Polymorphisms of Human STING Can Affect Innate Immune Response to Cyclic Dinucleotides, PLoS One, 2013, 1-16, 8-10-e77846.

Zeng et al., MAVS, cGAS, and Endogenous Retroviruses in T-Independent B Cell Responses, Science, 2014, 1486-1492, 346-6216.

Zhang et al., Cyclic GMP-AMP Containing Mixed Phosphodiester Linkages Is an Endogenous High-Affinity Ligand tor STING, Molecular Cell, 2013, 226-235, 51.

Zhou et al., The ER-Associated Protein ZDHHC1 Is a Positive Regulator of DNA Virus-Triggered, MITA/STING-Dependent Innate Immune Signaling, Cell Host & Microbe, 2014, 450-461, 16.

\* cited by examiner

AZA-BENZOTHIOPHENE COMPOUNDS AS STING AGONISTS

CROSS-REFERENCE TO RELATED APPLICATIONS

This application is a National Stage application of International Patent Application No. PCT/US2019/024455, filed Mar. 28, 2019, which claims the benefit of priority to U.S. Provisional Patent Application No. 62/651,968, filed Apr. 3, 2018.

FIELD OF THE INVENTION

The present disclosure relates to compounds and derivatives thereof that may be useful as STING (Stimulator of Interferon Genes) agonists that activate the STING pathway. The present disclosure also relates to compositions comprising such compounds, processes for the synthesis of such compounds, and to uses of such compounds, including administration of such compounds to induce immune response, to induce STING-dependent type I interferon production, and/or to treat a cell proliferation disorder, such as cancer.

REFERENCE TO SEQUENCE LISTING SUBMITTED ELECTRONICALLY

The sequence listing of the present application is submitted electronically via EFS-Web as an ASCII-formatted sequence listing, with a file name of "24577-SEQLIST-MARCH2019.txt", a creation date of Mar. 11, 2019, and a size of 13 KB. This sequence listing submitted via EFS-Web is part of the specification and is herein incorporated by reference in its entirety.

BACKGROUND OF THE INVENTION

The immune system has evolved to recognize and neutralize different types of threats in order to maintain the homeostasis of the host, and it is generally broken down into two arms: adaptive and innate. The adaptive immune system is specialized to recognize as foreign those antigens not naturally expressed in the host and to mount an anti-antigen response through the coordinated actions of many leukocyte subsets. The hallmark of adaptive immune responses is their ability to provide "memory" or long-lasting immunity against the encountered antigen. While this specific and long-lasting effect is critical to host health and survival, the adaptive immune response requires time to generate a full-blown response.

The innate immune system compensates for this time delay and is specialized to act quickly against different insults or danger signals. It provides the first line of defense against bacteria, viruses, parasites and other infectious threats, but it also responds strongly to certain danger signals associated with cellular or tissue damage. The innate immune system has no antigen specificity but does respond to a variety of effector mechanisms. Opsonization, phagocytosis, activation of the complement system, and production of soluble bioactive molecules such as cytokines or chemokines are all mechanisms by which the innate immune system mediates its response. By responding to these damage-associated molecular patterns (DAMPs) or pathogen-associated molecular patterns (PAMPs) described above, the innate immune system is able to provide broad protection against a wide range of threats to the host.

Free cytosolic DNA and RNA are among these PAMPs and DAMPs. It has recently been demonstrated that the main sensor for cytosolic DNA is cGAS (cyclic GMP-AMP synthase). Upon recognition of cytosolic DNA, cGAS catalyzes the generation of the cyclic-dinucleotide 2'3'-cGAMP, an atypical second messenger that strongly binds to the ER-transmembrane adaptor protein STING. A conformational change is undergone by cGAMP-bound STING, which translocates to a perinuclear compartment and induces the activation of critical transcription factors IRF-3 and NF-κB. This leads to a strong induction of type I interferons and production of pro-inflammatory cytokines such as IL-6, TNF-α and IFN-γ.

The importance of type I interferons and pro-inflammatory cytokines on various cells of the immune system has been very well established. In particular, these molecules strongly potentiate T-cell activation by enhancing the ability of dendritic cells and macrophages to uptake, process, present and cross-present antigens to T-cells. The T-cell stimulatory capacity of these antigen-presenting cells is augmented by the up-regulation of critical co-stimulatory molecules, such as CD80 or CD86. Finally, type I interferons can rapidly engage their cognate receptors and trigger the activation of interferon-responsive genes that can significantly contribute to adaptive immune cell activation.

From a therapeutic perspective, type I interferons are shown to have antiviral activities by directly inhibiting human hepatitis B virus and hepatitis C virus replication, and by stimulating immune responses to virally infected cells. Compounds that can induce type I interferon production are used in vaccines, where they act as adjuvants, enhancing specific immune responses to antigens and minimizing side effects by reducing dosage and broadening the immune response.

In addition, interferons, and compounds that can induce interferon production, have potential use in the treatment of human cancers. Such molecules are potentially useful as anti-cancer agents with multiple pathways of activity. Interferons can inhibit human tumor cell proliferation directly and may be synergistic with various approved chemotherapeutic agents. Type I interferons can significantly enhance anti-tumor immune responses by inducing activation of both the adaptive and innate immune cells. Finally, tumor invasiveness may be inhibited by interferons by modulating enzyme expression related to tissue remodeling.

In view of the potential of type I interferons and type I interferon-inducing compounds as anti-viral and anti-cancer agents, there remains a need for new agents that can induce potent type I interferon production. With the growing body of data demonstrating that the cGAS-STING cytosolic DNA sensory pathway has a significant capacity to induce type I interferons, the development of STING activating agents is rapidly taking an important place in today's anti-tumor therapy landscape.

SUMMARY OF THE INVENTION

The present disclosure relates to novel compounds of general formula (I). In particular, the present disclosure relates to compounds having the general structural formula (I):

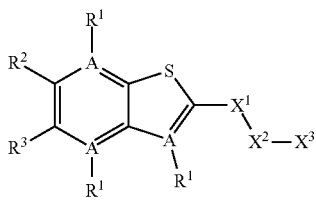

or pharmaceutically acceptable salts thereof, as described herein. Uses of compounds of general formula (I) and processes for making compounds of general formula (I) are also disclosed.

Other embodiments, aspects and features of the present disclosure are either further described in or will be apparent from the ensuing description, examples and appended claims.

BRIEF DESCRIPTION OF THE DRAWINGS

Not Applicable.

DETAILED DESCRIPTION OF THE INVENTION

The present disclosure includes compounds of general formula (I), and pharmaceutically acceptable salts thereof. These compounds and their pharmaceutically acceptable salts may be useful as agents to induce immune responses, to induce STING-dependent type I interferon production, and/or to treat a cell proliferation disorder.

In particular, the disclosure relates to compounds of general formula (I):

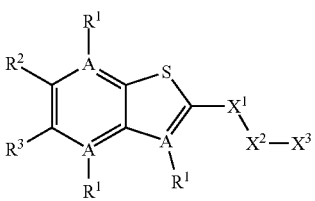

or a pharmaceutically acceptable salt thereof, wherein each A-$R^1$ is selected independently from the group consisting of C—$R^1$ and N, and at least one A-$R^1$ is CH; each $R^1$ is selected independently from the group consisting of H, halogen, $OR^6$, $N(R^6)_2$, $SR^6$, $C_1$-$C_6$ alkyl, $C_1$-$C_6$ haloalkyl, $C_1$-$C_6$ alkyl substituted by $OR^6$, $C_1$-$C_6$ alkyl substituted by $SR^6$, $C_1$-$C_6$ alkyl substituted by $N(R^6)_2$, $C_1$-$C_6$ haloalkyl substituted by $OR^6$, $C_1$-$C_6$ haloalkyl substituted by $SR^6$, and $C_1$-$C_6$ haloalkyl substituted by $N(R^6)_2$; $R^2$ is selected from the group consisting of H, halogen, CN, $OR^6$, $N(R^6)_2$, $COOR^6$, $C(O)N(R^6)_2$, $SR^6$, $SO_2R^6$, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and a 3- to 6-membered heterocyclic ring including 1 to 2 ring members selected from the group consisting of O, S, N, and $N(R^6)$, wherein said $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and 3- to 6-membered heterocyclic ring groups are optionally substituted by one or more substituents independently selected from the group consisting of CN, $OR^6$, $N(R^6)_2$, and $SR^6$, and wherein said $C_3$-$C_6$ cycloalkyl and 3- to 6-membered heterocyclic ring are each further optionally substituted with a member of the group consisting of $C_1$-$C_3$ alkyl and $C_1$-$C_3$ haloalkyl; $R^3$ is selected from the group consisting of H, halogen, CN, $OR^6$, $N(R^6)_2$, $COOR^6$, $C(O)N(R^6)_2$, $SR^6$, $SO_2R^6$, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and a 3- to 6-membered heterocyclic ring including 1 to 2 ring members selected from the group consisting of O, S, N, and $N(R^6)$, wherein said $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and 3- to 6-membered heterocyclic ring groups are optionally substituted by one or more substituents independently selected from the group consisting of CN, $OR^6$, $N(R^6)_2$, and $SR^6$, and wherein said $C_3$-$C_6$ cycloalkyl and 3- to 6-membered heterocyclic ring are each further optionally substituted with a member of the group consisting of $C_1$-$C_3$ alkyl and $C_1$-$C_3$ haloalkyl; optionally $R^3$ and an adjacent A-$R^1$ may be taken together with the atoms to which they are attached form a 5- or 6-membered heterocyclic ring including 1 to 2 ring members selected from the group consisting of O, S, N, and $N(R^6)$ wherein said heterocyclic ring is optionally substituted with or more members of the group consisting of $C_1$-$C_3$ alkyl and $C_1$-$C_3$ haloalkyl; each $R^6$ is independently selected from the group consisting of H, $C_1$-$C_6$ alkyl, and $C_1$-$C_6$ haloalkyl, wherein said $C_1$-$C_6$ alkyl, and $C_1$-$C_6$ haloalkyl are optionally substituted with OH, O($C_1$-$C_3$ alkyl), and O($C_1$-$C_3$ haloalkyl); $X^1$ is selected from the group consisting of $CH_2$ and C(O); $X^2$ is $(C(R^8)_2)_{(1-3)}$; each $R^8$ is independently selected from the group consisting of H, halogen, CN, $OR^6$, $N(R^6)_2$, $SR^6$, $C_1$-$C_6$ alkyl, $C_1$-$C_6$ haloalkyl, $C_3$-$C_6$ cycloalkyl, and a 3- to 6-membered heterocyclic ring including 1 to 2 ring members selected from the group consisting of O, S, N, and $N(R^6)$, wherein said $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and 3- to 6-membered heterocyclic ring groups are optionally substituted by one or more substituents independently selected from the group consisting of CN, $OR^6$, $N(R^6)_2$, and $SR^6$, and wherein said $C_3$-$C_6$ cycloalkyl and 3- to 6-membered heterocyclic ring are each further optionally substituted with a member of the group consisting of $C_1$-$C_3$ alkyl and $C_1$-$C_3$ haloalkyl; optionally 2 $R^8$ on different carbon atoms may be taken together, along with the atoms to which they are attached, to form a 3- to 6-membered fused ring; optionally 2 $R^8$ on a single carbon atom may be taken together, along with the atom to which they are attached, to form a 3- to 6-membered spirocycle; $X^3$ is selected from the group consisting of $COOR^6$,

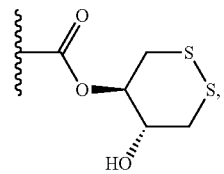

$C(O)SR^6$, $C(S)OR^6$, $SO_2R^6$, and $C(O)N(R^9)_2$; and each $R^9$ is independently selected from the group consisting of H, $COOR^6$, and $SO_2R^6$.

In a first embodiment, each A-$R^1$ is selected independently from the group consisting of C—$R^1$ and N, and at least one A-$R^1$ is CH. In particular aspects of this embodiment,

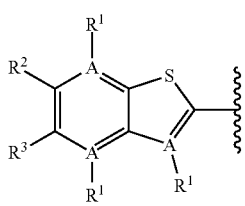

is selected from the group consisting of

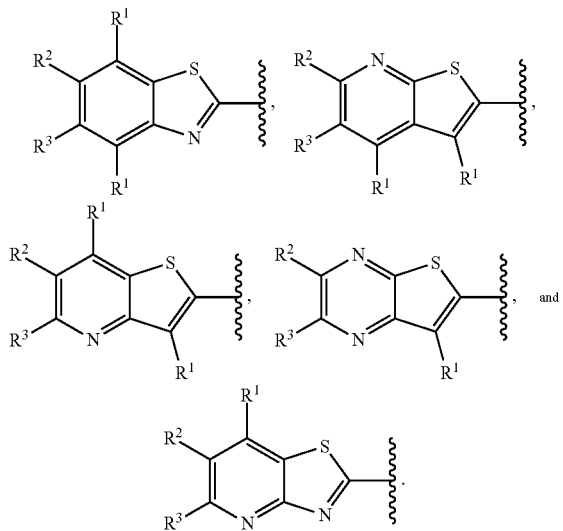

In more particular aspects of this embodiment,

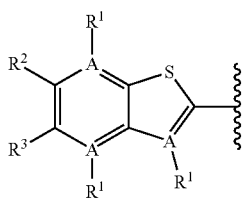

is selected from the group consisting of

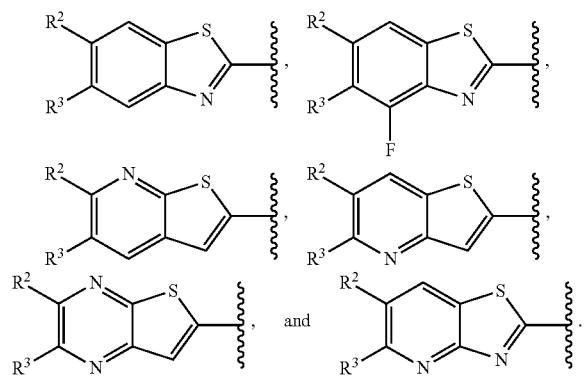

In this embodiment, all other groups are as provided in the general formula (I) above.

In a second embodiment, each $R^1$ is selected independently from the group consisting of H, halogen, $OR^6$, $N(R^6)_2$, $C_1$-$C_6$ alkyl, $C_1$-$C_6$ haloalkyl, $C_1$-$C_6$ alkyl substituted by $OR^6$, $C_1$-$C_6$ alkyl substituted by $N(R^6)_2$, $COOR^6$, and $C(O)N(R^6)_2$. In instances of this aspect, each $R^1$ is selected independently from the group consisting of H, F, Cl, $C_1$-$C_3$ alkyl, and $C_1$-$C_3$ haloalkyl. In particular instances of this aspect, $R^1$ each $R^1$ is selected independently from the group consisting of H and F. In this embodiment, all other groups are as provided in the general formula (I) or in the first embodiment above.

In a third embodiment, $R^2$ is selected from the group consisting of halogen, CN, $OR^6$, $N(R^6)_2$, $COOR^6$, $C(O)N(R^6)_2$, $SO_2R^6$, $C_1$-$C_6$ alkyl, $C_1$-$C_6$ haloalkyl, $C_1$-$C_6$ alkyl substituted by $OR^6$, $C_2$-$C_6$ alkenyl, $C_2$-$C_6$ haloalkenyl, $C_2$-$C_6$ alkenyl substituted by $OR^6$, $C_2$-$C_6$ alkynyl, $C_2$-$C_6$ haloalkynyl, $C_2$-$C_6$ alkynyl substituted by $OR^6$, $C_3$-$C_6$ cycloalkyl, and a 3- to 6-membered heterocyclic ring including 1 to 2 ring members selected from the group consisting of O, S, and $N(R^6)$. In instances of this aspect, $R^2$ is selected from the group consisting of halogen, $C_1$-$C_3$ alkyl, $C_1$-$C_3$ haloalkyl, $OC_1$-$C_3$ alkyl, $C_2$-$C_3$ alkenyl, and $N(R^6)_2$. In particular instances of this aspect, $R^2$ is selected from the group consisting of Br, Cl, $CH_3$, $CH_2CH_3$, $CH=CH_2$, $OCH_3$, and $N(R^6)_2$. In more particular instances of this aspect, $R^2$ is selected from the group consisting of Br and $OCH_3$. In this embodiment, all other groups are as provided in the general formula (I) or in the first or second embodiments described above.

In a fourth embodiment, $R^3$ is selected from the group consisting of halogen, CN, $OR^6$, $N(R^6)_2$, $COOR^6$, $C(O)N(R^6)_2$, $SO_2R^6$, $C_1$-$C_6$ alkyl, $C_1$-$C_6$ haloalkyl, $C_1$-$C_6$ alkyl substituted by $OR^6$, $C_2$-$C_6$ alkenyl, $C_2$-$C_6$ haloalkenyl, $C_2$-$C_6$ alkenyl substituted by $OR^6$, $C_2$-$C_6$ alkynyl, $C_2$-$C_6$ haloalkynyl, $C_2$-$C_6$ alkynyl substituted by $OR^6$, $C_3$-$C_6$ cycloalkyl, and a 3- to 6-membered heterocyclic ring including 1 to 2 ring members selected from the group consisting of O, S, and $N(R^6)$. In instances of this aspect, $R^3$ is selected from the group consisting of halogen, $C_1$-$C_3$ alkyl, $C_1$-$C_3$ haloalkyl, $OC_1$-$C_3$ alkyl, $C_2$-$C_3$ alkenyl, and $N(R^6)_2$. In particular instances of this aspect, $R^3$ is selected from the group consisting of Br, Cl, $CH_3$, $CH_2CH_3$, $CH=CH_2$, $OCH_3$, and $N(R^6)_2$. In more particular instances of this aspect, $R^3$ is selected from the group consisting of Br, Cl, and $OCH_3$. In certain embodiments, $R^3$ and an adjacent A-$R^1$ may be taken together with the atoms to which they are attached form a 5- or 6-membered heterocyclic ring including 1 to 2 ring members selected from the group consisting of O, S, N, and $N(R^6)$, wherein said heterocyclic ring is optionally substituted with or more members of the group consisting of $C_1$-$C_3$ alkyl and $C_1$-$C_3$ haloalkyl. In this embodiment, all other groups are as provided in the general formula (I) or in the first through third embodiments described above.

In a fifth embodiment, each $R^6$ is selected independently from the group consisting of H, $C_1$-$C_6$ alkyl, and $C_1$-$C_6$ haloalkyl. In aspects of this embodiment, each $R^6$ is selected independently from the group consisting of H, $C_1$-$C_3$ alkyl, and $C_1$-$C_3$ haloalkyl. In particular aspects of this embodiment, each $R^6$ is selected independently from the group consisting of H and $CH_3$. In this embodiment, all other groups are as provided in the general formula (I) or in the first through fourth embodiments described above.

In a sixth embodiment, $X^3$ is selected from the group consisting of $COOR^6$, $C(O)SR^6$, $C(S)OR^6$,

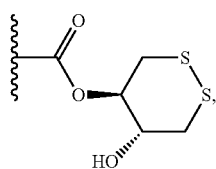 [SMILES: *C(=O)O[C@H]1CSSC[C@@H]1O]

$SO_2R^6$, and $C(O)N(R^9)_2$. In aspects of this embodiment, $X^3$ is selected from the group consisting of $COOR^6$,

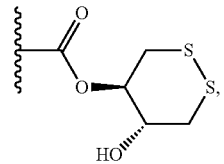 [SMILES: *C(=O)O[C@H]1CSSC[C@@H]1O]

$SO_2R^6$, and $C(O)N(R^9)_2$. In particular aspects of this embodiment, $X^3$ is $COOR^6$. In even more particular aspects of this embodiment, $X^3$ is COOH. In this embodiment, all other groups are as provided in the general formula (I) or in the first through fifth embodiments described above.

In a seventh embodiment, each $R^9$ is independently selected from the group consisting of H, $COOR^6$, and $SO_2R^6$. In instances of this embodiment, each $R^9$ is independently H. In this embodiment, all other groups are as provided in the general formula (I) or in the first through sixth embodiments described above.

In an eighth embodiment, $X^2$ is $(C(R^8)_2)_{(1-3)}$, wherein each $R^8$ is independently selected from the group consisting of H, halogen, $C_1$-$C_6$ alkyl, CN, $OR^6$, $N(R^6)_2$, $C_1$-$C_6$ haloalkyl, $C_3$-$C_6$ cycloalkyl, $C_1$-$C_6$ alkyl substituted by $OR^6$, and $C_1$-$C_6$ alkyl substituted by $N(R^6)_2$; optionally 2 $R^8$ on different carbon atoms may be taken together, along with the atoms to which they are attached, to form a 3- to 6-membered fused ring; optionally 2 $R^8$ on a single carbon atom may be taken together, along with the atom to which they are attached, to form a 3- to 6-membered spirocycle. In a first aspect of this embodiment, $X^2$ is $CH_2CHR^8$, where $R^8$ is selected from the group consisting of H, $C_1$-$C_3$ alkyl, $C_1$-$C_3$ alkyl substituted by OH, $C_1$-$C_3$ alkyl substituted by $OC_1$-$C_3$ alkyl, and $C_3$-$C_6$ cycloalkyl. In particular instances of this first aspect, $X^2$ is $CH_2CHR^8$, wherein $R^8$ is selected from the group consisting of H, $CH_3$, $CH_2OH$, $CH_2CH_3$, $CH_2CH_2CH_3$, $CH(CH_3)_2$, $CH_2OCH_3$, and cyclopropyl. In a second aspect of this embodiment, $X^2$ is $CHR^8CHR^8$, where $R^8$ is selected from the group consisting of H, $C_1$-$C_3$ alkyl, $C_1$-$C_3$ alkyl substituted by OH, $C_1$-$C_3$ alkyl substituted by $OC_1$-$C_3$ alkyl, and $C_3$-$C_6$ cycloalkyl, and optionally 2 $R^8$ on different carbon atoms are taken together, along with the atoms to which they are attached, to form a 3- to 6-membered fused ring. In particular instances of this second aspect, $X^2$ is $CHR^8CHR^8$, where $R^8$ is selected from the group consisting of H and $C_1$-$C_3$ alkyl, and optionally 2 $R^8$ on different carbon atoms may be taken together, along with the atoms to which they are attached, to form a 3- to 6-membered fused ring. In a third aspect of this embodiment, $X^2$ is $CH_2C(R^8)_2$, where $R^8$ is selected from the group consisting of H, $C_1$-$C_3$ alkyl, $C_1$-$C_3$ alkyl substituted by OH, $C_1$-$C_3$ alkyl substituted by $OC_1$-$C_3$ alkyl, and $C_3$-$C_6$ cycloalkyl, and optionally 2 $R^8$ on a single carbon atom may be taken together, along with the atom to which they are attached, to form a 3- to 6-membered spirocycle. In particular instances of this third aspect, $X^2$ is $CH_2C(R^8)_2$, where $R^8$ is selected from the group consisting of H and $C_1$-$C_3$ alkyl, and optionally 2 $R^8$ on a single carbon atom may be taken together, along with the atom to which they are attached, to form a 3- to 6-membered spirocycle. In this embodiment, all other groups are as provided in the general formula (I) or in the first through seventh embodiments described above.

In a ninth embodiment, $X^1$ is C(O) or $CH_2$. In aspects of this embodiment, $X^1$ is C(O). In this embodiment, all other groups are as provided in the general formula (I) or in the first through eighth embodiments described above.

In a tenth embodiment,

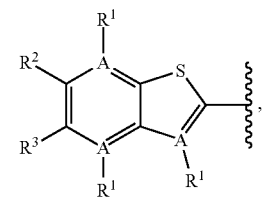

is selected from the group consisting of

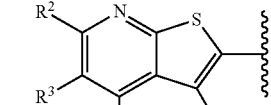

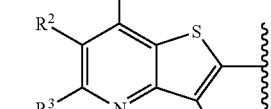

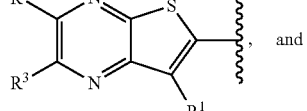

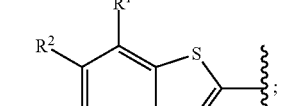

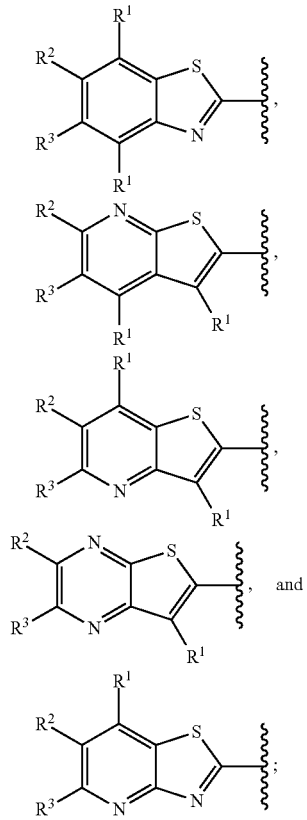

each $R^1$ is selected independently from the group consisting of H, F, Cl, $C_1$-$C_3$ alkyl, and $C_1$-$C_3$ haloalkyl; $R^2$ is selected from the group consisting of halogen, $C_1$-$C_3$ alkyl, $C_1$-$C_3$ haloalkyl, $OC_1$-$C_3$ alkyl, $C_2$-$C_3$ alkenyl, and $N(R^6)_2$; $R^3$ is selected from the group consisting of halogen, $C_1$-$C_3$ alkyl, $C_1$-$C_3$ haloalkyl, $OC_1$-$C_3$ alkyl, $C_2$-$C_3$ alkenyl, and $N(R^6)_2$; $X^1$-$X^2$-$X^3$ is selected from the group consisting of C(O)—$CH_2CHR^8$—$COOR^6$, C(O)—$CH_2CHR^8$—$SO_2R^6$, and C(O)—$CH_2CHR^8$—$C(O)N(R^9)_2$; each $R^6$ is independently selected from the group consisting of H, $C_1$-$C_3$ alkyl, and $C_1$-$C_3$ haloalkyl; and each $R^8$ is selected from the group consisting of H, $C_1$-$C_3$ alkyl, $C_1$-$C_3$ alkyl substituted by OH, $C_1$-$C_3$ alkyl substituted by $OC_1$-$C_3$ alkyl, and $C_3$-$C_6$ cycloalkyl. In instances of this aspect,

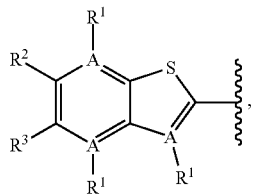

is selected from the group consisting of

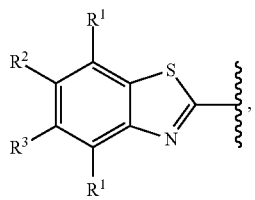

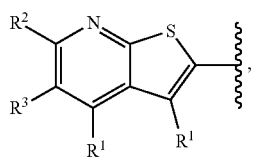

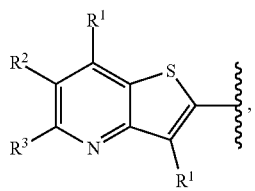

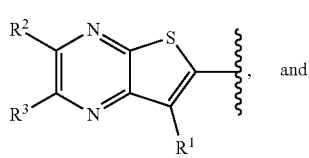

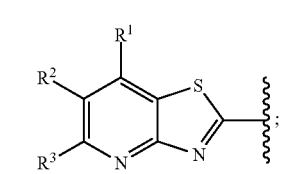

each $R^1$ is selected from the group consisting of H and F; $R^2$ is selected from the group consisting of Br, Cl, $CH_3$, $CH_2CH_3$, CH=$CH_2$, $OCH_3$, and $N(R^6)_2$; $R^3$ is selected from the group consisting of Br, Cl, $CH_3$, $CH_2CH_3$, CH=$CH_2$, $OCH_3$, and $N(R^6)_2$; $X^1$-$X^2$-$X^3$ is C(O)—$CH_2CHR^8$—COOH; each $R^6$ is independently selected from the group consisting of H and $CH_3$; $R^8$ is selected from the group consisting of H, $CH_3$, $CH_2CH_3$, $CH_2CH_2CH_3$, $CH(CH_3)_2$, $CH_2OCH_3$, and cyclopropyl. In still more particular instances,

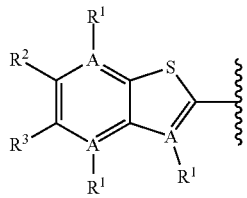

is selected from the group consisting of

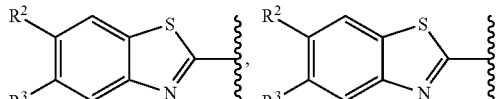

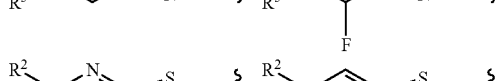

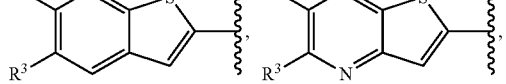

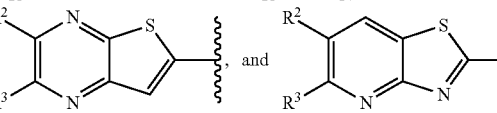

$R^2$ is selected from the group consisting of Br, Cl, $CH_3$, $CH_2CH_3$, CH=$CH_2$, $OCH_3$, and $N(R^6)_2$; $R^3$ is selected from the group consisting of Br, Cl, $CH_3$, $CH_2CH_3$, CH=$CH_2$, $OCH_3$, and $N(R^6)_2$; $X^1$-$X^2$-$X^3$ is C(O)—$CH_2CHR^8$—COOH; each $R^6$ is independently selected from the group consisting of H and $CH_3$; $R^8$ is selected from the group consisting of H, $CH_3$, $CH_2CH_3$, $CH_2CH_2CH_3$, $CH(CH_3)_2$, $CH_2OCH_3$, and cyclopropyl. In this embodiment, all other groups are as provided in the general formula (I) or in the first through ninth embodiments described above.

An eleventh embodiment relates to a pharmaceutical composition, said pharmaceutical composition comprising (a) a compound according to general formula (I) above or the first through tenth embodiments described above or a pharmaceutically acceptable salt thereof; and (b) a pharmaceutically acceptable carrier.

A twelfth embodiment relates to methods of inducing an immune response in a patient in need of therapy, comprising administering a therapeutically effective amount of a compound according to general formula (I) above or the first through tenth embodiments described above described above or a pharmaceutically acceptable salt thereof to the patient.

A thirteenth embodiment relates to methods of inducing an immune response in a patient in need of therapy, comprising administering a therapeutically effective amount of a composition according to the eleventh aspect described above to the patient.

A fourteenth embodiment relates to methods of inducing a STING-dependent type I interferon production in a patient in need of therapy, comprising administering a therapeutically effective amount of a compound according to general formula (I) above or the first through tenth embodiments described above or a pharmaceutically acceptable salt thereof to the patient.

A fifteenth embodiment relates to methods of inducing STING-dependent type I interferon production in a patient in need of therapy, comprising administering a therapeutically effective amount of a composition according to the eleventh aspect described above to the patient.

A sixteenth embodiment relates to methods of inducing STING-dependent cytokine production in a patient in need of therapy, comprising administering a therapeutically effective amount of a compound according to general formula (I) above or the first through tenth embodiments described above or a pharmaceutically acceptable salt thereof to the patient.

A seventeenth embodiment relates to methods of inducing a STING-dependent cytokine production in a patient in need of therapy, comprising administering a therapeutically effective amount of a composition according to the eleventh aspect described above to the patient.

An eighteenth embodiment relates to methods of treating a cell proliferation disorder in a patient in need of therapy, comprising administering a therapeutically effective amount of a compound of general formula (I), or a pharmaceutically acceptable salt thereof to the patient. In aspects of this eighteenth embodiment, the cell proliferation disorder is cancer.

A nineteenth embodiment relates to methods of treating a cell proliferation disorder in a patient in need of therapy, said method comprising administering a therapeutically effective amount of a composition according to the eleventh aspect described above to the patient. In aspects of this nineteenth embodiment, the cell proliferation disorder is cancer.

In each embodiment described herein, variables $R^1$, $R^2$, $R^3$, $R^6$, $R^8$, $R^9$, A, $X^1$, $X^2$, and $X^3$ of general formula (I), and the various aspects and instances thereof, are each selected independently from each other, with the proviso that at least one of $R^1$, $R^2$, $R^3$, $R^6$, $R^8$, and $R^9$ is not H.

A twentieth embodiment relates to a compound selected from the group consisting of

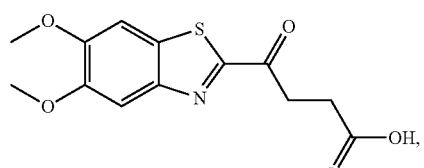

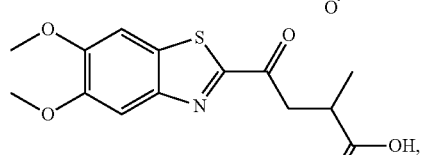

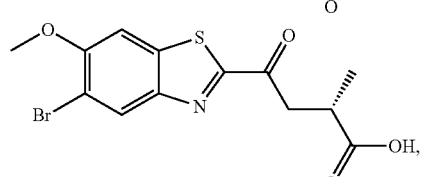

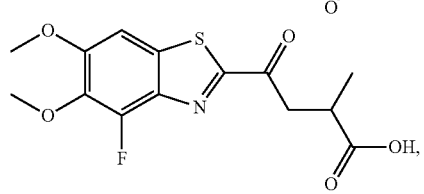

-continued

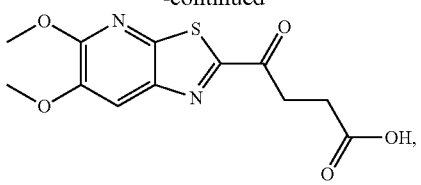

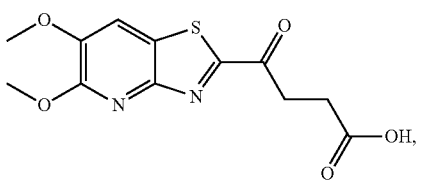

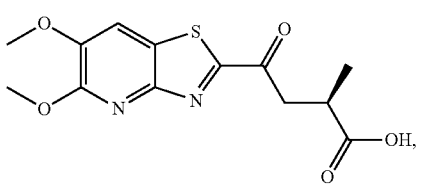

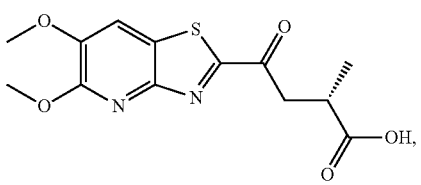

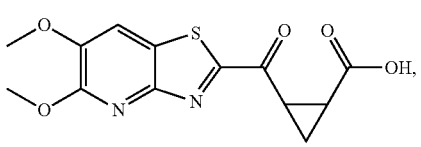

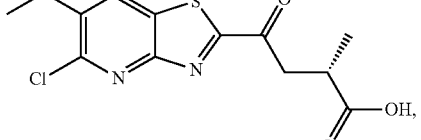

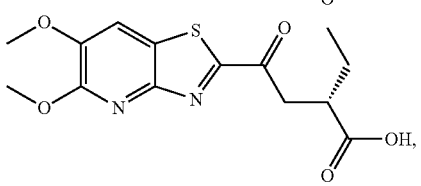

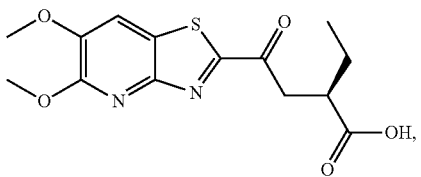

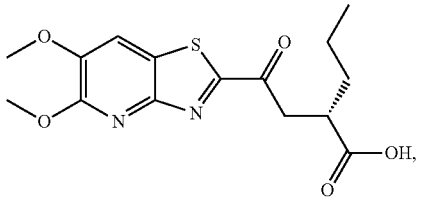

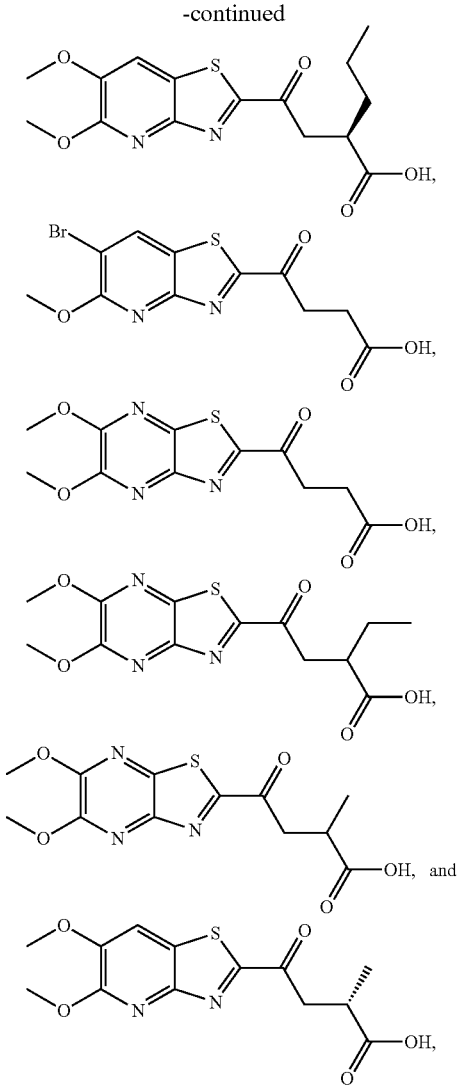

and pharmaceutically acceptable salts thereof.

A first aspect of the twentieth embodiment relates to methods of inducing an immune response in a patient in need of therapy, comprising administering a therapeutically effective amount of a compound according to the twentieth embodiment above or a pharmaceutically acceptable salt thereof to the patient.

A second aspect of the twentieth embodiment relates to methods of inducing an immune response in a patient in need of therapy, comprising administering a therapeutically effective amount of a composition comprising a compound according to the twentieth embodiment above or a pharmaceutically acceptable salt thereof to the patient.

A third aspect of the twentieth embodiment relates to methods of inducing STING-dependent type I interferon production in a patient in need of therapy, comprising administering a therapeutically effective amount of a compound according to the twentieth embodiment above or a pharmaceutically acceptable salt thereof to the patient.

A fourth aspect of the twentieth embodiment relates to methods of inducing STING-dependent type I interferon production in a patient in need of therapy, comprising administering a therapeutically effective amount of a composition comprising a compound according to the twentieth embodiment above or a pharmaceutically acceptable salt thereof to the patient.

A fifth aspect of the twentieth embodiment relates to methods of inducing STING-dependent cytokine production in a patient in need of therapy, comprising administering a therapeutically effective amount of a compound according to the twentieth embodiment above or a pharmaceutically acceptable salt thereof to the patient.

A sixth aspect of the twentieth embodiment relates to methods of inducing a STING-dependent cytokine production in a patient in need of therapy, comprising administering a therapeutically effective amount of a composition comprising a compound according to the twentieth embodiment above or a pharmaceutically acceptable salt thereof to the patient.

A seventh aspect of the twentieth embodiment relates to methods of treating a cell proliferation disorder in a patient in need of therapy, comprising administering a therapeutically effective amount of a compound of general formula (I), or a pharmaceutically acceptable salt thereof to the patient. In instances of this seventh aspect of the twentieth embodiment, the cell proliferation disorder is cancer.

An eighth aspect of the twentieth embodiment relates to methods of treating a cell proliferation disorder in a patient in need of therapy, said method comprising administering a therapeutically effective amount of a composition according to the eleventh aspect described above to the patient. In instances of this eighth aspect of the twentieth embodiment, the cell proliferation disorder is cancer.

A twenty-first embodiment relates to a compound selected from the exemplary species depicted in Examples 1 through 19 shown below.

A first aspect of the twenty-first embodiment relates to methods of inducing an immune response in a patient in need of therapy, comprising administering a therapeutically effective amount of a compound according to the twenty-first embodiment above or a pharmaceutically acceptable salt thereof to the patient.

A second aspect of the twenty-first embodiment relates to methods of inducing an immune response in a patient in need of therapy, comprising administering a therapeutically effective amount of a composition comprising a compound according to the twenty-first embodiment above or a pharmaceutically acceptable salt thereof to the patient.

A third aspect of the twenty-first embodiment relates to methods of inducing STING-dependent type I interferon production in a patient in need of therapy, comprising administering a therapeutically effective amount of a compound according to the twenty-first embodiment above or a pharmaceutically acceptable salt thereof to the patient.

A fourth aspect of the twenty-first embodiment relates to methods of inducing STING-dependent type I interferon production in a patient in need of therapy, comprising administering a therapeutically effective amount of a composition comprising a compound according to the twenty-first embodiment above or a pharmaceutically acceptable salt thereof to the patient.

A fifth aspect of the twenty-first embodiment relates to methods of inducing STING-dependent cytokine production in a patient in need of therapy, comprising administering a therapeutically effective amount of a compound according to the twenty-first embodiment above or a pharmaceutically acceptable salt thereof to the patient.

A sixth aspect of the twenty-first embodiment relates to methods of inducing STING-dependent cytokine production in a patient in need of therapy, comprising a therapeutically effective amount of a composition comprising a compound according to the twenty-first embodiment above or a pharmaceutically acceptable salt thereof to the patient.

A seventh aspect of the twenty-first embodiment relates to methods of treating a cell proliferation disorder in a patient in need of therapy, comprising administering a therapeutically effective amount of a compound of general formula (I), or a pharmaceutically acceptable salt thereof to the patient. In instances of this seventh aspect of the twenty-first embodiment, the cell proliferation disorder is cancer.

An eighth aspect of the twenty-first embodiment relates to methods of treating a cell proliferation disorder in a patient in need of therapy, said method comprising administering a therapeutically effective amount of a composition according to the eleventh aspect described above to the patient. In instances of this eighth aspect of the twenty-first embodiment, the cell proliferation disorder is cancer.

Other embodiments of the present disclosure include the following:

(a) A pharmaceutical composition comprising an effective amount of a compound of general formula (I), or a pharmaceutically acceptable salt thereof, and a pharmaceutically acceptable carrier.

(b) The pharmaceutical composition of (a), further comprising an active agent selected from the group consisting of STING agonist compounds, anti-viral compounds, antigens, adjuvants, CTLA-4 and PD-1 pathway antagonists and other immunomodulatory agents, lipids, liposomes, peptides, anti-cancer and chemotherapeutic agents.

(c) A pharmaceutical combination that is (i) a compound of general formula (I), or a pharmaceutically acceptable salt thereof, and (ii) an active agent selected from the group consisting of STING agonist compounds, anti-viral compounds, antigens, adjuvants, CTLA-4 and PD-1 pathway antagonists and other immunomodulatory agents, lipids, liposomes, peptides, anti-cancer and chemotherapeutic agents; wherein the compound of general formula (I), or pharmaceutically acceptable salt thereof, and the active agent are each employed in an amount that renders the combination effective for inducing an immune response in a patient.

(d) A method of inducing an immune response in a patient in need of therapy, which comprises administering to the patient a therapeutically effective amount of a compound of general formula (I), or a pharmaceutically acceptable salt thereof.

(e) A method of inducing an immune response in a patient in need of therapy, which comprises administering to the patient a therapeutically effective amount of a composition of (a), a composition of (b), or a combination of (c).

(f) A method of inducing STING-dependent type I interferon production in a patient in need of therapy, which comprises administering to the patient a therapeutically effective amount of a compound of general formula (I), or a pharmaceutically acceptable salt thereof.

(g) A method of inducing STING-dependent type I interferon production in a patient in need of therapy, which comprises administering to the patient a therapeutically effective amount of a composition of (a), a composition of (b), or a combination of (c).

(h) A method of inducing STING-dependent cytokine production in a patient in need of therapy, which comprises administering to the patient a therapeutically effective amount of a compound of general formula (I), or a pharmaceutically acceptable salt thereof.

(i) A method of inducing STING-dependent cytokine production in a patient in need of therapy, which comprises administering to the patient a therapeutically effective amount of a composition of (a), a composition of (b), or a combination of (c).

(j) A method of treating a cell proliferation disorder in a patient in need of therapy, said method comprising administering a therapeutically effective amount of a compound of general formula (I), or a pharmaceutically acceptable salt thereof to the patient;

(k) The method of (j), wherein the cell proliferation disorder is cancer.

(l) A method of treating a cell proliferation disorder in a patient in need of therapy, said method comprising administering a therapeutically effective amount of a composition of (a), a composition of (b), or a combination of (c) to the patient.

(m) The method of (l), wherein the cell proliferation disorder is cancer.

The present disclosure also includes a compound of the present disclosure for use (i) in, (ii) as a medicament for, or (iii) in the preparation of a medicament for: (a) inducing an immune response in a patient in need of therapy, or (b) inducing STING-dependent cytokine production in a patient in need of therapy. In these uses, the compounds of the present disclosure can optionally be employed in combination with one or more active agents selected from STING agonist compounds, anti-viral compounds, antigens, adjuvants, CTLA-4 and PD-1 pathway antagonists and other immunomodulatory agents, lipids, liposomes, peptides, anti-cancer agents, and chemotherapeutic agents.

Additional embodiments of the disclosure include the pharmaceutical compositions, combinations and methods set forth in (a) through (m) above and the uses set forth in the preceding paragraph, wherein the compound of the present disclosure employed therein is a compound of one of the embodiments, aspects, instances, occurrences, or features of the compounds described above. In all of these embodiments, the compound may optionally be used in the form of a pharmaceutically acceptable salt, as appropriate.

In the embodiments of the compound provided above, it is to be understood that each embodiment may be combined with one or more other embodiments, to the extent that such a combination provides a stable compound and is consistent with the description of the embodiments. It is further to be understood that the embodiments of compositions and methods provided as (a) through (m) above are understood to include all embodiments of the compounds, including such embodiments as result from combinations of embodiments.

The terms "subject" or alternatively "patient" as used herein refers to a mammal that has been the object of treatment, observation, or experiment. The mammal may be male or female. The mammal may be one or more selected from the group consisting of humans, bovine (e.g., cows), porcine (e.g., pigs), ovine (e.g., sheep), capra (e.g., goats), equine (e.g., horses), canine (e.g., domestic dogs), feline (e.g., house cats), Lagomorpha (rabbits), rodents (e.g., rats or mice), *Procyon lotor* (e.g., raccoons). In particular embodiments, the subject is human.

As used herein, the term "immune response" relates to any one or more of the following: specific immune response, non-specific immune response, both specific and non-specific response, innate response, primary immune response, adaptive immunity, secondary immune response, memory immune response, immune cell activation, immune cell proliferation, immune cell differentiation, and cytokine expression. In certain embodiments, a compound of general formula (I), or a pharmaceutically acceptable salt of the foregoing, is administered in conjunction with one or more additional therapeutic agents including anti-viral compounds, vaccines intended to stimulate an immune response to one or more predetermined antigens, adjuvants, CTLA-4 and PD-1 pathway antagonists and other immunomodulatory agents, lipids, liposomes, peptides, anti-cancer agents, and chemotherapeutic agents, etc. In certain embodiments, a compound of general formula (I), or a pharmaceutically acceptable salt of the foregoing, is administered in conjunction with one or more additional compositions including anti-viral compounds, vaccines intended to stimulate an immune response to one or more predetermined antigens, adjuvants, CTLA-4 and PD-1 pathway antagonists and other immunomodulatory agents, lipids, liposomes, peptides, anti-cancer agents, and chemotherapeutic agents, etc.

Compounds

The term "alkyl" refers to a straight or branched chain, saturated aliphatic hydrocarbon radical having a number of carbon atoms in the specified range. Thus, for example, "$C_{1-6}$ alkyl" (or "$C_1$-$C_6$ alkyl") refers to any of the hexyl alkyl and pentyl alkyl isomers as well as n-, iso-, sec- and tert-butyl, n- and iso-propyl, ethyl, and methyl. As another example, "$C_{1-4}$ alkyl" refers to n-, iso-, sec- and tert-butyl, n- and isopropyl, ethyl, and methyl.

As used herein, the term "alkenyl" refers to a straight or branched chain, unsaturated aliphatic hydrocarbon radical having a number of carbon atoms in the specified range and including one or more double bonds.

As used herein, the term "alkynyl" refers to a straight or branched chain, unsaturated aliphatic hydrocarbon radical having a number of carbon atoms in the specified range and including one or more triple bonds.

The term "halogen" (or "halo") refers to fluorine, chlorine, bromine, and iodine (alternatively referred to as fluoro, chloro, bromo, and iodo or F, Cl, Br, and I).

The term "haloalkyl" refers to an alkyl group as defined above in which one or more of the hydrogen atoms have been replaced with a halogen. Thus, for example, "$C_{1-6}$ haloalkyl" (or "$C_1$-$C_6$ haloalkyl") refers to a $C_1$ to $C_6$ linear or branched alkyl group as defined above with one or more halogen substituents. The term "fluoroalkyl" has an analogous meaning except the halogen substituents are restricted to fluoro. Suitable fluoroalkyls include the series $(CH_2)_{0-4}CF_3$ (i.e., trifluoromethyl, 2,2,2-trifluoroethyl, 3,3,3-trifluoro-n-propyl, etc.).

As used herein, the term "haloalkenyl" refers to an alkenyl group as defined above in which one or more of the hydrogen atoms have been replaced with a halogen.

As used herein, the term "haloalkynyl" refers to an alkynyl group as defined above in which one or more of the hydrogen atoms have been replaced with a halogen.

As used herein, the term "alkoxy" as used herein, alone or in combination, includes an alkyl group connected to the oxy connecting atom. The term "alkoxy" also includes alkyl ether groups, where the term "alkyl" is defined above, and "ether" means two alkyl groups with an oxygen atom between them. Examples of suitable alkoxy groups include methoxy, ethoxy, n-propoxy, i-propoxy, n-butoxy, s-butoxy, t-butoxy, methoxymethane (also referred to as "dimethyl ether"), and methoxyethane (also referred to as "ethyl methyl ether").

As used herein, the term "cycloalkyl" refers to a saturated hydrocarbon containing one ring having a specified number of carbon atoms. Examples of cycloalkyl include cyclopropyl, cyclobutyl, cyclopentyl, and cyclohexyl.

As used herein, the term "heterocycle", "heterocyclyl", or "heterocyclic", as used herein, represents a stable 3- to 6-membered monocyclic that is either saturated or unsaturated, and that consists of carbon atoms and from one to two heteroatoms selected from the group consisting of N, O, and S. The heterocyclic ring may be attached at any heteroatom or carbon atom which results in the creation of a stable structure. The term includes heteroaryl moieties. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, triazolyl and thienyl.

As used herein, the term "fused ring" refers to a cyclic group formed by substituents on separate atoms in a straight or branched alkane, or to a cyclic group formed by substituents on separate atoms in another ring.

As used herein, the term "spirocycle" or "spirocyclic ring" refers to a pendant cyclic group formed by substituents on a single atom.

Unless expressly stated to the contrary, all ranges cited herein are inclusive; i.e., the range includes the values for the upper and lower limits of the range as well as all values in between. As an example, temperature ranges, percentages, ranges of equivalents, and the like described herein include the upper and lower limits of the range and any value in the continuum there between. Numerical values provided herein, and the use of the term "about", may include variations of ±1%, ±2%, ±3%, ±4%, ±5%, ±10%, ±15%, and ±20% and their numerical equivalents.

As used herein, the term "one or more" item includes a single item selected from the list as well as mixtures of two or more items selected from the list.

In the compounds of general formula (I), and pharmaceutically acceptable salts of the foregoing, the atoms may exhibit their natural isotopic abundances, or one or more of the atoms may be artificially enriched in a particular isotope having the same atomic number, but an atomic mass or mass number different from the atomic mass or mass number predominantly found in nature. The present disclosure is meant to include all suitable isotopic variations of the the compounds of general formula (I), and pharmaceutically acceptable salts of the foregoing. For example, different isotopic forms of hydrogen (H) include protium ($^1H$), deuterium ($^2H$), and tritium ($^3H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched the compounds of general formula (I), and pharmaceutically acceptable salts of the foregoing, can be prepared without undue experimentation by conventional techniques well known to those skilled in the art or by processes analogous to those described in the Schemes and Examples herein using appropriate isotopically-enriched reagents and/or intermediates.

In particular embodiments of the compounds of general formula (I), and pharmaceutically acceptable salts of the foregoing, the compounds are isotopically enriched with deuterium. In aspects of these embodiments, one or more of $R^1$, $R^2$, $R^3$, $R^6$, $R^8$, and $R^9$ may include deuterium.

As shown in the general structural formulas and the structures of specific compounds as provided herein, a straight line at a chiral center includes both (R) and (S) stereoisomers and mixtures thereof. Also, unless otherwise specified (e.g., 100% purified compound), reference to a particular stereochemistry at a position provides a compound having the indicated stereochemistry but does not exclude the presence of stereoisomers having different stereochemistry at the indicated position.

Recitation or depiction of a specific compound in the claims (i.e., a species) without a specific stereoconfiguration designation, or with such a designation for less than all chiral centers, is intended to encompass, for such undesignated chiral centers, the racemate, racemic mixtures, each individual enantiomer, a diastereoisomeric mixture and each individual diastereomer of the compound where such forms are possible due to the presence of one or more asymmetric centers. The separation of a mixture of stereoisomers can be carried out at an intermediate step during the synthesis of a compound of general formula (I), or a pharmaceutically acceptable salt of the foregoing, or it can be done on a final racemic product. Absolute stereochemistry may be determined by X-ray crystallography of crystalline products or crystalline intermediates, which are derivatized, if necessary, with a reagent containing a stereogenic center of known configuration. Alternatively, absolute stereochemistry may be determined by Vibrational Circular Dichroism (VCD) spectroscopy analysis. The present invention includes all such isomers, as well as salts, solvates (including hydrates), and solvated salts of such racemates, enantiomers, diastereomers, tautomers, and mixtures thereof.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism, the invention includes both the cis form and the trans form, as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of general formula (I), or a pharmaceutically acceptable salt of the foregoing, or it can be done on a final racemic product. Absolute stereochemistry may be determined by X-ray crystallography of crystalline products or crystalline intermediates that are derivatized, if necessary, with a reagent containing a stereogenic center of known configuration. Unless a particular isomer, salt, solvate (including hydrates) or solvated salt of such racemate, enantiomer, or diastereomer is indicated, the present invention includes all such isomers, as well as salts, solvates (including hydrates), and solvated salts of such racemates, enantiomers, diastereomers, and mixtures thereof.

The term "compound" refers to the compound and, in certain embodiments, to the extent they are stable, any hydrate or solvate thereof. A hydrate is the compound complexed with water, and a solvate is the compound complexed with a solvent, which may be an organic solvent or an inorganic solvent.

A "stable" compound is a compound that can be prepared and isolated and whose structure and properties remain or can be caused to remain essentially unchanged for a period of time sufficient to allow use of the compound for the purposes described herein (e.g., therapeutic administration to a subject). The compounds of the present invention are limited to stable compounds embraced by general formula (I), or pharmaceutically acceptable salts thereof.

Salts

As indicated above, the compounds of the present invention can be employed in the form of pharmaceutically acceptable salts. Those skilled in the art will recognize those instances in which the compounds of the invention may form salts. Examples of such compounds are described herein by reference to possible salts. Such reference is for illustration only. Pharmaceutically acceptable salts can be used with compounds for treating patients. Non-pharmaceutical salts may, however, be useful in the preparation of intermediate compounds.

The term "pharmaceutically acceptable salt" refers to a salt (including an inner salt such as a zwitterion) that possesses effectiveness similar to the parent compound and that is not biologically or otherwise undesirable (e.g., is neither toxic nor otherwise deleterious to the recipient thereof). Thus, an embodiment of the invention provides pharmaceutically acceptable salts of the compounds of the invention. The term "salt(s)", as employed herein, denotes any of the following: acidic salts formed with inorganic and/or organic acids, as well as basic salts formed with inorganic and/or organic bases. Salts of compounds of the invention may be formed by methods known to those of ordinary skill in the art, for example, by reacting a compound of the invention with an amount of acid or base, such as an equivalent amount, in a medium such as one in which the salt precipitates or in aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates ("mesylates"), naphthalenesulfonates, nitrates, oxalates, phosphates, propionates, salicylates, succinates, sulfates, tartarates, thiocyanates, toluenesulfonates (also known as tosylates) and the like. Suitable salts include acid addition salts that may, for example, be formed by mixing a solution of a compound with a solution of a pharmaceutically acceptable acid such as hydrochloric acid, sulfuric acid, acetic acid, trifluoroacetic acid, or benzoic acid. Additionally, acids that are generally considered suitable for the formation of pharmaceutically useful salts from basic pharmaceutical compounds are discussed, for example, by P. Stahl et al, Camille G. (eds.), *Handbook of Pharmaceutical Salts. Properties, Selection and Use*. (2002) Zurich: Wiley-VCH; S. Berge et al, Journal of Pharmaceutical Sciences (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quaternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others. Compounds carrying an acidic moiety can be mixed with suitable pharmaceutically acceptable salts to provide, for example, alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

All such acid salts and base salts are intended to be pharmaceutically acceptable salts within the scope of the invention and all acid and base salts are considered equivalent to the free forms of the corresponding compounds for purposes of the invention.

In addition, when a compound of the invention contains both a basic moiety, such as, but not limited to an aliphatic primary, secondary, tertiary or cyclic amine, an aromatic or heteroaryl amine, pyridine or imidazole, and an acidic moiety, such as, but not limited to tetrazole or carboxylic acid, zwitterions ("inner salts") may be formed and are included within the terms "salt(s)" as used herein. It is understood that certain compounds of the invention may exist in zwitterionic form, having both anionic and cationic centers within the same compound and a net neutral charge. Such zwitterions are included within the invention.

Methods of Preparing Compounds

Several methods for preparing the compounds of general formula (I), and pharmaceutically acceptable salts of the foregoing, are described in the following Schemes and Examples. Starting materials and intermediates are purchased from commercial sources, made from known procedures, or are otherwise illustrated. In some cases the order of carrying out the steps of the reaction schemes may be varied to facilitate the reaction or to avoid unwanted reaction products.

In the following Methods and Schemes, LG represents a leaving group, which may be a halide or triflate group. The variables A, $R^1$, $R^2$, $R^3$, $R^6$, $R^8$, $X^1$, $X^2$, and $X^3$ have the same meaning as provided above.

Method 1

Benzo[b]thiophene-2-carboxylic acids or aza-benzo[b]thiophene-2-carboxylic acids, and pharmaceutically acceptable salts thereof, are typically prepared from ortho-halo benzaldehydes 1A as shown in Scheme 1. The sequence starts with treatment with an alpha-thioacetic acid ester under basic conditions. The ester in the resulting compound 1B is cleaved to the carboxylic acid under either acidic or basic conditions to provide the desired substituted benzo[b]thiophene-2-carboxylic acid or aza-benzo[b]thiophene-2-carboxylic acid 1C.

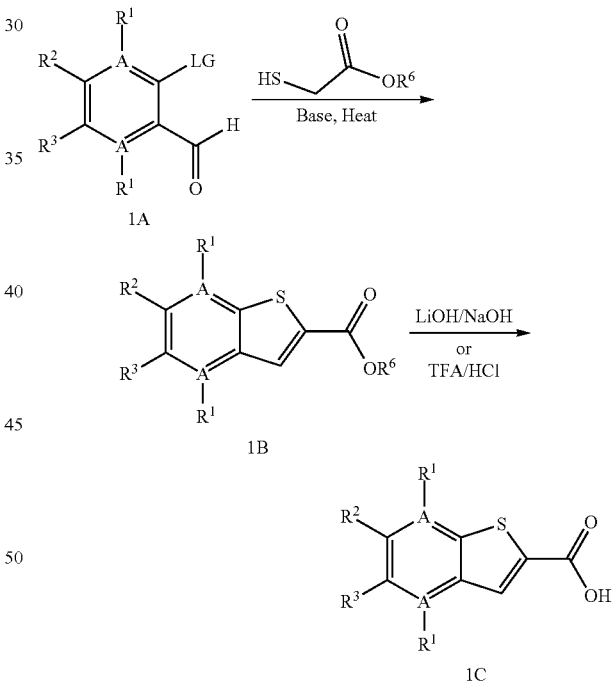

Method 2

Benzothiazole-2-carboxylic acids or aza-benzothiazole-2-carboxylic acids, and pharmaceutically acceptable salts thereof, can be prepared from substituted aminoarenes 2A as shown in Scheme 2. The sequence starts with acylation with a 2-chloro-2-oxoacetate ester under basic conditions. Reaction of 2B with Lawesson's reagent affords the thioamide 2C, which in turn is cyclized by reaction with potassium ferricyanide to afford the desired substituted benzothiazole-2-carboxylic acid or aza-benzothiazole-2-carboxylic acid 2D.

SCHEME 2

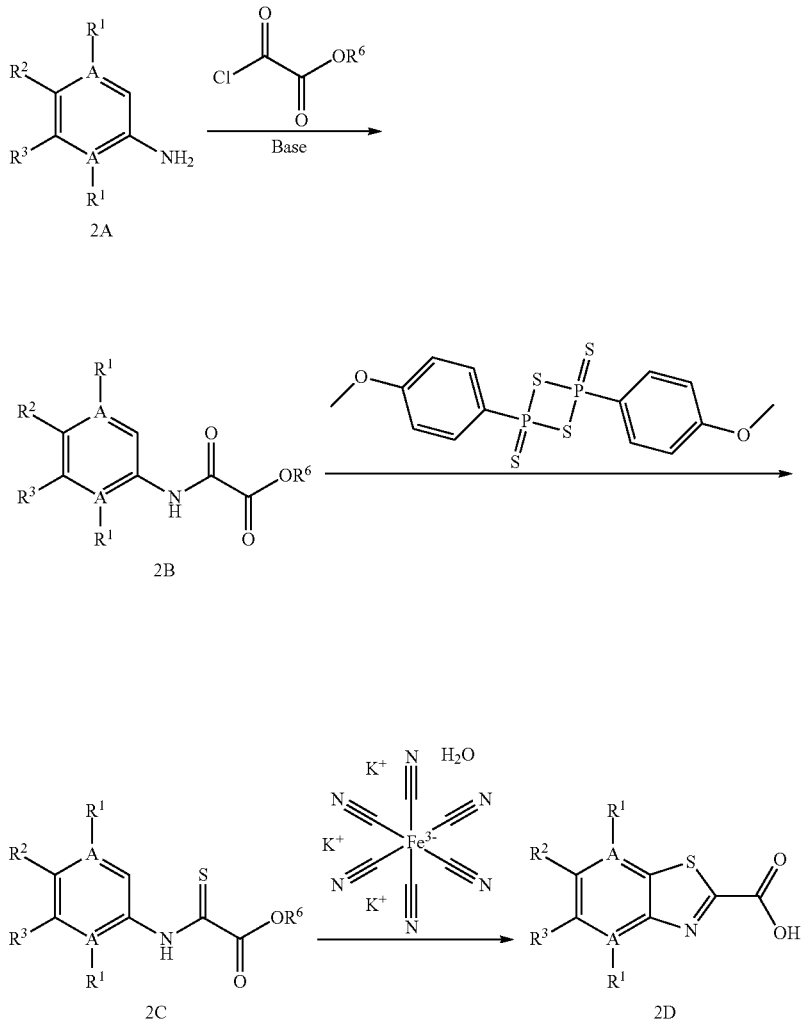

Method 3

Another method for the preparation of benzo[b]thiophene-2-carboxylic acids, aza-benzo[b]thiophene-2-carboxylic acids, benzothiazole-2-carboxylic acids, or aza-benzothiazole-2-carboxylic acids, and pharmaceutically acceptable salts thereof, is detailed in Scheme 3. The sequence starts with the appropriate [5.6] heterobicycle 3A unsubstituted at the 2 position. Treatment with n-butyllithium or LDA, followed by treatment with a cyclic anhydride affords the desired product 3B.

SCHEME 3

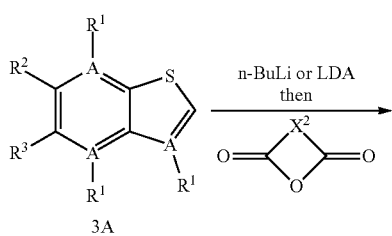

-continued

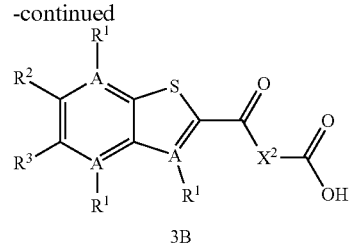

Method 4

Another method for the preparation of benzo[b]thiophene-2-carboxylic acids, aza-benzo[b]thiophene-2-carboxylic acids, benzothiazole-2-carboxylic acids, or aza-benzothiazole-2-carboxylic acids, and pharmaceutically acceptable salts thereof, is detailed in Scheme 4. The sequence starts with the appropriate [5.6] heterobicycle-2-carboxylic acid 4A, which is reacted with a metal 3-alkoxy-3-oxopropanoate to afford the beta-ketoester 4B. Alkylation with an alpha-haloester affords substitution at the 2-position of the alkyl side chain 4C. Both esters are hydrolyzed under acidic, basic, or a combination of acidic and basic conditions to afford the desired product 4D.

SCHEME 4

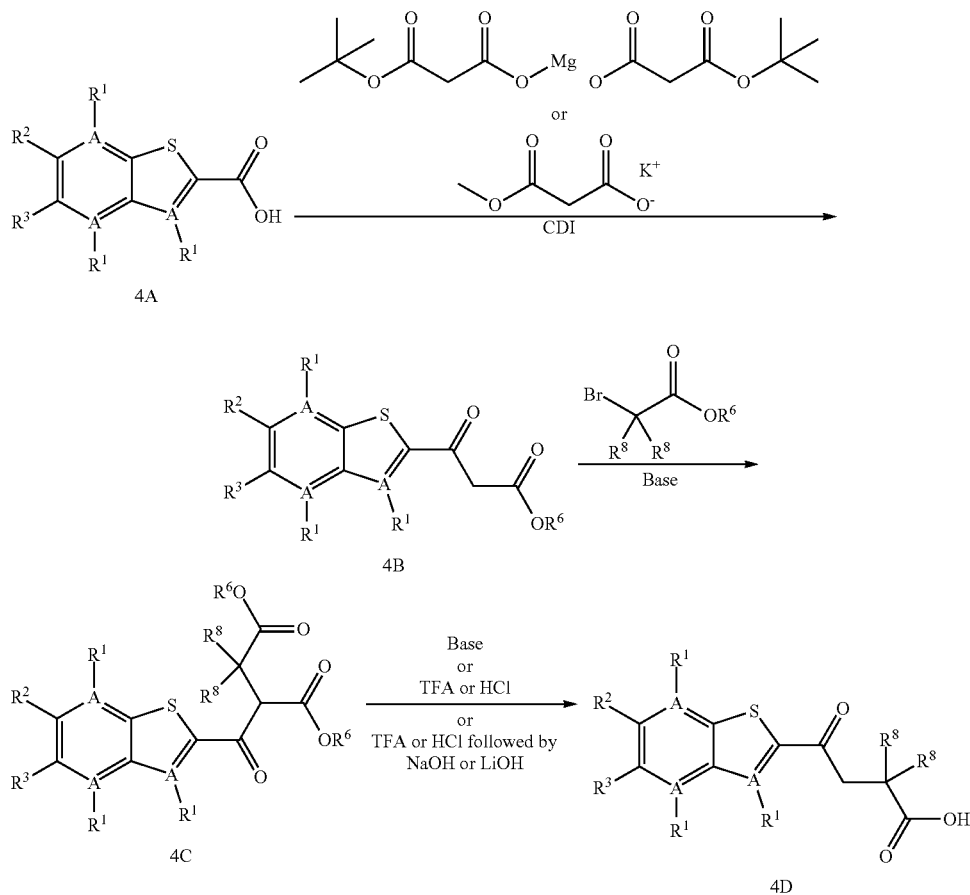

Method 5

Another method for the preparation of benzo[b]thiophene-2-carboxylic acids, aza-benzo[b]thiophene-2-carboxylic acids, benzothiazole-2-carboxylic acids, or aza-benzothiazole-2-carboxylic acids, and pharmaceutically acceptable salts thereof, is detailed in Scheme 5. The sequence starts with the appropriate [5.6] heterobicycle-2-carboxylic acid 5A which is converted to the acyl chloride 5B by treatment with either oxalyl chloride or phosphorus (V) oxychloride. The acid chloride 5B is reacted with an alkyl zinc reagent, typically containing an ester, using a transition metal such as copper or palladium to afford 4-ketoester 5C. The ester is cleaved by reaction with either acid or base to afford the desired product 5D.

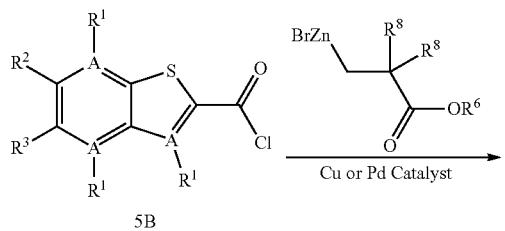

SCHEME 5

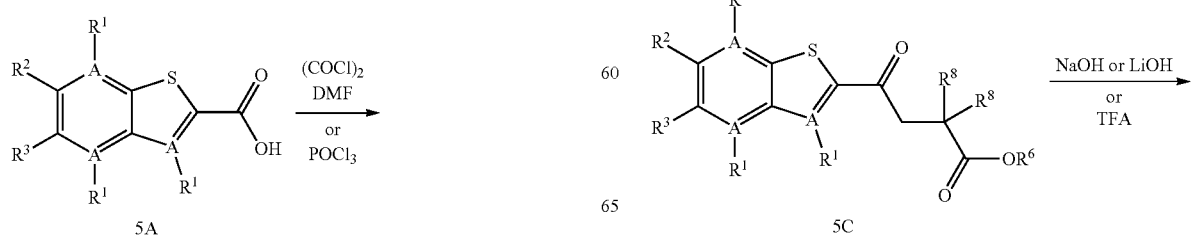

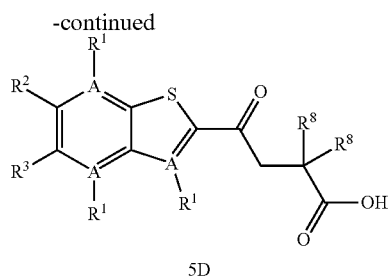

5D

Methods of Use

Compounds described herein having therapeutic applications, such as the compounds of general formula (I), the compounds of the Examples 1 through 19, and pharmaceutically acceptable salts of the foregoing, may be administered to a patient for the purpose of inducing an immune response, inducing STING-dependent cytokine production and/or inducing anti-tumor activity. The term "administration" and variants thereof (e.g., "administering" a compound) means providing the compound to the individual in need of treatment. When a compound is provided in combination with one or more additional active agents (e.g., antiviral agents useful for treating HCV infection or anti-tumor agents for treating cancers), "administration" and its variants are each understood to include concurrent and sequential provision of the compound or salt and other agents.

The compounds disclosed herein may be STING agonists. These compounds are potentially useful in treating diseases or disorders including, but not limited to, cell proliferation disorders. Cell-proliferation disorders include, but are not limited to, cancers, benign papillomatosis, gestational trophoblastic diseases, and benign neoplastic diseases, such as skin papilloma (warts) and genital papilloma.

In specific embodiments, the disease or disorder to be treated is a cell proliferation disorder. In certain embodiments, the cell proliferation disorder is cancer. In particular embodiments, the cancer is selected from brain and spinal cancers, cancers of the head and neck, leukemia and cancers of the blood, skin cancers, cancers of the reproductive system, cancers of the gastrointestinal system, liver and bile duct cancers, kidney and bladder cancers, bone cancers, lung cancers, malignant mesothelioma, sarcomas, lymphomas, glandular cancers, thyroid cancers, heart tumors, germ cell tumors, malignant neuroendocrine (carcinoid) tumors, midline tract cancers, and cancers of unknown primary (i.e., cancers in which a metastasized cancer is found but the original cancer site is not known). In particular embodiments, the cancer is present in an adult patient; in additional embodiments, the cancer is present in a pediatric patient. In particular embodiments, the cancer is AIDS-related.

In specific embodiments, the cancer is selected from brain and spinal cancers. In particular embodiments, the cancer is selected from the group consisting of anaplastic astrocytomas, glioblastomas, astrocytomas, and estheosioneuroblastomas (also known as olfactory blastomas). In particular embodiments, the brain cancer is selected from the group consisting of astrocytic tumor (e.g., pilocytic astrocytoma, subependymal giant-cell astrocytoma, diffuse astrocytoma, pleomorphic xanthoastrocytoma, anaplastic astrocytoma, astrocytoma, giant cell glioblastoma, glioblastoma, secondary glioblastoma, primary adult glioblastoma, and primary pediatric glioblastoma), oligodendroglial tumor (e.g., oligodendroglioma, and anaplastic oligodendroglioma), oligoastrocytic tumor (e.g., oligoastrocytoma, and anaplastic oligoastrocytoma), ependymoma (e.g., myxopapillary ependymoma, and anaplastic ependymoma); medulloblastoma, primitive neuroectodermal tumor, schwannoma, meningioma, atypical meningioma, anaplastic meningioma, pituitary adenoma, brain stem glioma, cerebellar astrocytoma, cerebral astorcytoma/malignant glioma, visual pathway and hypothalmic glioma, and primary central nervous system lymphoma. In specific instances of these embodiments, the brain cancer is selected from the group consisting of glioma, glioblastoma multiforme, paraganglioma, and suprantentorial primordial neuroectodermal tumors (sP-NET).

In specific embodiments, the cancer is selected from cancers of the head and neck, including nasopharyngeal cancers, nasal cavity and paranasal sinus cancers, hypopharyngeal cancers, oral cavity cancers (e.g., squamous cell carcinomas, lymphomas, and sarcomas), lip cancers, oropharyngeal cancers, salivary gland tumors, cancers of the larynx (e.g., laryngeal squamous cell carcinomas, rhabdomyosarcomas), and cancers of the eye or ocular cancers. In particular embodiments, the ocular cancer is selected from the group consisting of intraocular melanoma and retinoblastoma.

In specific embodiments, the cancer is selected from leukemia and cancers of the blood. In particular embodiments, the cancer is selected from the group consisting of myeloproliferative neoplasms, myelodysplastic syndromes, myelodysplastic/myeloproliferative neoplasms, acute myeloid leukemia (AML), myelodysplastic syndrome (MDS), chronic myelogenous leukemia (CML), myeloproliferative neoplasm (MPN), post-MPN AML, post-MDS AML, del(5q)-associated high risk MDS or AML, blast-phase chronic myelogenous leukemia, angioimmunoblastic lymphoma, acute lymphoblastic leukemia, Langerans cell histiocytosis, hairy cell leukemia, and plasma cell neoplasms including plasmacytomas and multiple myelomas. Leukemias referenced herein may be acute or chronic.

In specific embodiments, the cancer is selected from skin cancers. In particular embodiments, the skin cancer is selected from the group consisting of melanoma, squamous cell cancers, and basal cell cancers.

In specific embodiments, the cancer is selected from cancers of the reproductive system. In particular embodiments, the cancer is selected from the group consisting of breast cancers, cervical cancers, vaginal cancers, ovarian cancers, prostate cancers, penile cancers, and testicular cancers. In specific instances of these embodiments, the cancer is a breast cancer selected from the group consisting of ductal carcinomas and phyllodes tumors. In specific instances of these embodiments, the breast cancer may be male breast cancer or female breast cancer. In specific instances of these embodiments, the cancer is a cervical cancer selected from the group consisting of squamous cell carcinomas and adenocarcinomas. In specific instances of these embodiments, the cancer is an ovarian cancer selected from the group consisting of epithelial cancers.

In specific embodiments, the cancer is selected from cancers of the gastrointestinal system. In particular embodiments, the cancer is selected from the group consisting of esophageal cancers, gastric cancers (also known as stomach cancers), gastrointestinal carcinoid tumors, pancreatic cancers, gallbladder cancers, colorectal cancers, and anal cancer. In instances of these embodiments, the cancer is selected from the group consisting of esophageal squamous cell carcinomas, esophageal adenocarcinomas, gastric adenocarcinomas, gastrointestinal carcinoid tumors, gastrointestinal stromal tumors, gastric lymphomas, gastrointestinal lymphomas, solid pseudopapillary tumors of the pancreas, pancreatoblastoma, islet cell tumors, pancreatic carcinomas including acinar cell carcinomas and ductal adenocarcinomas, gallbladder adenocarcinomas, colorectal adenocarcinomas, and anal squamous cell carcinomas.

In specific embodiments, the cancer is selected from liver and bile duct cancers. In particular embodiments, the cancer is liver cancer (also known as hepatocellular carcinoma). In particular embodiments, the cancer is bile duct cancer (also known as cholangiocarcinoma); in instances of these embodiments, the bile duct cancer is selected from the group consisting of intrahepatic cholangiocarcinoma and extrahepatic cholangiocarcinoma.

In specific embodiments, the cancer is selected from kidney and bladder cancers. In particular embodiments, the cancer is a kidney cancer selected from the group consisting of renal cell cancer, Wilms tumors, and transitional cell cancers. In particular embodiments, the cancer is a bladder cancer selected from the group consisting of urethelial carcinoma (a transitional cell carcinoma), squamous cell carcinomas, and adenocarcinomas.

In specific embodiments, the cancer is selected from bone cancers. In particular embodiments, the bone cancer is selected from the group consisting of osteosarcoma, malignant fibrous histiocytoma of bone, Ewing sarcoma, chordoma (cancer of the bone along the spine).

In specific embodiments, the cancer is selected from lung cancers. In particular embodiments, the lung cancer is selected from the group consisting of non-small cell lung cancer, small cell lung cancers, bronchial tumors, and pleuropulmonary blastomas.

In specific embodiments, the cancer is selected from malignant mesothelioma. In particular embodiments, the cancer is selected from the group consisting of epithelial mesothelioma and sarcomatoids.

In specific embodiments, the cancer is selected from sarcomas. In particular embodiments, the sarcoma is selected from the group consisting of central chondrosarcoma, central and periosteal chondroma, fibrosarcoma, clear cell sarcoma of tendon sheaths, and Kaposi's sarcoma.

In specific embodiments, the cancer is selected from lymphomas. In particular embodiments, the cancer is selected from the group consisting of Hodgkin lymphoma (e.g., Reed-Sternberg cells), non-Hodgkin lymphoma (e.g., diffuse large B-cell lymphoma, follicular lymphoma, mycosis fungoides, Sezary syndrome, primary central nervous system lymphoma), cutaneous T-cell lymphomas, primary central nervous system lymphomas.

In specific embodiments, the cancer is selected from glandular cancers. In particular embodiments, the cancer is selected from the group consisting of adrenocortical cancer (also known as adrenocortical carcinoma or adrenal cortical carcinoma), pheochromocytomas, paragangliomas, pituitary tumors, thymoma, and thymic carcinomas.

In specific embodiments, the cancer is selected from thyroid cancers. In particular embodiments, the thyroid cancer is selected from the group consisting of medullary thyroid carcinomas, papillary thyroid carcinomas, and follicular thyroid carcinomas.

In specific embodiments, the cancer is selected from germ cell tumors. In particular embodiments, the cancer is selected from the group consisting of malignant extracranial germ cell tumors and malignant extragonadal germ cell tumors. In specific instances of these embodiments, the malignant extragonadal germ cell tumors are selected from the group consisting of nonseminomas and seminomas.

In specific embodiments, the cancer is selected from heart tumors. In particular embodiments, the heart tumor is selected from the group consisting of malignant teratoma, lymphoma, rhabdomyosarcoma, angiosarcoma, chondrosarcoma, infantile fibrosarcoma, and synovial sarcoma.

In specific embodiments, the cell-proliferation disorder is selected from benign papillomatosis, benign neoplastic diseases and gestational trophoblastic diseases. In particular embodiments, the benign neoplastic disease is selected from skin papilloma (warts) and genital papilloma. In particular embodiments, the gestational trophoblastic disease is selected from the group consisting of hydatidiform moles, and gestational trophoblastic neoplasia (e.g., invasive moles, choriocarcinomas, placental-site trophoblastic tumors, and epithelioid trophoblastic tumors).

As used herein, the terms "treatment" and "treating" refer to all processes in which there may be a slowing, interrupting, arresting, controlling, or stopping of the progression of a disease or disorder described herein. The terms do not necessarily indicate a total elimination of all disease or disorder symptoms.

The terms "administration of" and or "administering" a compound should be understood to include providing a compound described herein, or a pharmaceutically acceptable salt thereof, and compositions of the foregoing to a subject.

The amount of a compound administered to a subject is an amount sufficient to induce an immune response and/or to induce STING-dependent type I interferon production in the subject. In an embodiment, the amount of a compound can be an "effective amount" or "therapeutically effective amount," such that the subject compound is administered in an amount that will elicit, respectively, a biological or medical (i.e., intended to treat) response of a tissue, system, animal, or human that is being sought by a researcher, veterinarian, medical doctor, or other clinician. An effective amount does not necessarily include considerations of toxicity and safety related to the administration of a compound.

An effective amount of a compound will vary with the particular compound chosen (e.g., considering the potency, efficacy, and/or half-life of the compound); the route of administration chosen; the condition being treated; the severity of the condition being treated; the age, size, weight, and physical condition of the subject being treated; the medical history of the subject being treated; the duration of the treatment; the nature of a concurrent therapy; the desired therapeutic effect; and like factors and can be routinely determined by the skilled artisan.

The compounds disclosed herein may be administered by any suitable route including oral and parenteral administration. Parenteral administration is typically by injection or infusion and includes intravenous, intramuscular, and subcutaneous injection or infusion.

The compounds disclosed herein may be administered once or according to a dosing regimen where a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound disclosed herein depend on the pharmacokinetic properties of that compound, such as absorption, distribution and half-life, that can be determined by a skilled artisan. In addition, suitable dosing regimens, including the duration such regimens are administered, for a compound disclosed herein depend on the disease or condition being treated, the severity of the disease or condition, the age and physical condition of the subject being treated, the medical history of the subject being treated, the nature of concurrent therapy, the desired therapeutic effect, and like factors within the knowledge and expertise of the skilled artisan. It will be further understood by such skilled artisans that suitable dosing regimens may require adjustment given an individual subject's response to the dosing regimen or over time as the individual subject needs change. Typical daily dosages may vary depending upon the particular route of administration chosen.

One embodiment of the present disclosure provides for a method of treating a cell proliferation disorder comprising administration of a therapeutically effective amount of a compound of general formula (I), and pharmaceutically acceptable salts of the foregoing, to a subject in need of treatment thereof. In embodiments, the disease or disorder to be treated is a cell proliferation disorder. In aspects of these embodiments, the cell proliferation disorder is cancer. In further aspects of these embodiments, the cancer is selected from brain and spinal cancers, cancers of the head and neck, leukemia and cancers of the blood, skin cancers, cancers of the reproductive system, cancers of the gastrointestinal system, liver and bile duct cancers, kidney and bladder cancers, bone cancers, lung cancers, malignant mesothelioma, sarcomas, lymphomas, glandular cancers, thyroid cancers, heart tumors, germ cell tumors, malignant neuroendocrine (carcinoid) tumors, midline tract cancers, and cancers of unknown primary.

In one embodiment, disclosed herein is the use of a compound of general formula (I), or a pharmaceutically acceptable salt of the foregoing, in a therapy. The compound may be useful in a method of inducing an immune response and/or inducing STING-dependent type I interferon production in a subject, such as a mammal in need of such inhibition, comprising administering an effective amount of the compound to the subject.

In one embodiment, disclosed herein is a pharmaceutical composition comprising at least one compound of general formula (I), or at least one pharmaceutically acceptable salt of the foregoing, for use in potential treatment to induce an immune response and/or to induce STING-dependent type I interferon production.

One embodiment disclosed herein is the use of a compound of general formula (I), or a pharmaceutically acceptable salt of the foregoing, in the manufacture of a medicament to induce an immune response and/or to induce STING-dependent type I interferon production. In embodiments, the disease or disorder to be treated is a cell proliferation disorder. In aspects of these embodiments, the cell proliferation disorder is cancer. In further aspects of these embodiments, the cancer is selected from brain and spinal cancers, cancers of the head and neck, leukemia and cancers of the blood, skin cancers, cancers of the reproductive system, cancers of the gastrointestinal system, liver and bile duct cancers, kidney and bladder cancers, bone cancers, lung cancers, malignant mesothelioma, sarcomas, lymphomas, glandular cancers, thyroid cancers, heart tumors, germ cell tumors, malignant neuroendocrine (carcinoid) tumors, midline tract cancers, and cancers of unknown primary.

Compositions

The term "composition" as used herein is intended to encompass a dosage form comprising a specified compound in a specified amount, as well as any dosage form that results, directly or indirectly, from combination of a specified compound in a specified amount. Such term is intended to encompass a dosage form comprising a compound of general formula (I), or a pharmaceutically acceptable salt of the foregoing, and one or more pharmaceutically acceptable carriers or excipients. Accordingly, the compositions of the present disclosure encompass any composition made by admixing a compound of the present disclosure and one or more pharmaceutically acceptable carrier or excipients. By "pharmaceutically acceptable", it is meant the carriers or excipients are compatible with the compound disclosed herein and with other ingredients of the composition.

For the purpose of inducing an immune response and/or inducing STING-dependent type I interferon production, the compounds of general formula (I), or pharmaceutically acceptable salts of the foregoing, can be administered by means that produces contact of the active agent with the agent's site of action. The compounds can be administered by conventional means available for use in conjunction with pharmaceuticals, either as individual therapeutic agents or in a combination of therapeutic agents. The compounds can be administered alone, but typically are administered with a pharmaceutical carrier selected on the basis of the chosen route of administration and standard pharmaceutical practice.

In one embodiment, disclosed herein is a composition comprising a compound of general formula (I), or a pharmaceutically acceptable salt of the foregoing, and one or more pharmaceutically acceptable carriers or excipients. The composition may be prepared and packaged in bulk form in which a therapeutically effective amount of a compound of the disclosure can be extracted and then given to a subject, such as with powders or syrups. Alternatively, the composition may be prepared and packaged in unit dosage form in which each physically discrete unit contains a therapeutically effective amount of a compound of general formula (I), or a pharmaceutically acceptable salt of the foregoing.

The compounds disclosed herein and a pharmaceutically acceptable carrier or excipient(s) will typically be formulated into a dosage form adapted for administration to a subject by a desired route of administration. For example, dosage forms include those adapted for (1) oral administration, such as tablets, capsules, caplets, pills, troches, powders, syrups, elixirs, suspensions, solutions, emulsions, sachets, and cachets; and (2) parenteral administration, such as sterile solutions, suspensions, and powders for reconstitution. Suitable pharmaceutically acceptable carriers or excipients will vary depending upon the particular dosage form chosen. In addition, suitable pharmaceutically acceptable carriers or excipients may be chosen for a particular function that they may serve in the composition. For example, certain pharmaceutically acceptable carriers or excipients may be chosen for their ability to facilitate the production of uniform dosage forms. Certain pharmaceutically acceptable carriers or excipients may be chosen for their ability to facilitate the production of stable dosage forms. Certain pharmaceutically acceptable carriers or excipients may be chosen for their ability to facilitate the carrying or transporting of a compound disclosed herein, once administered to the subject, from one organ or portion of the body to another organ or another portion of the body. Certain pharmaceutically acceptable carriers or excipients may be chosen for their ability to enhance patient compliance.

Suitable pharmaceutically acceptable excipients include the following types of excipients: diluents, lubricants, binders, disintegrants, fillers, glidants, granulating agents, coating agents, wetting agents, solvents, co-solvents, suspending agents, emulsifiers, sweeteners, flavoring agents, flavor masking agents, coloring agents, anti-caking agents, hemectants, chelating agents, plasticizers, viscosity increasing agents, antioxidants, preservatives, stabilizers, surfactants, and buffering agents.

A skilled artisan possesses the knowledge and skill in the art to select suitable pharmaceutically acceptable carriers and excipients in appropriate amounts for the use in the compositions of the disclosure. In addition, there are a number of resources available to the skilled artisan, which describe pharmaceutically acceptable carriers and excipients and may be useful in selecting suitable pharmaceutically acceptable carriers and excipients. Examples include REMINGTON'S PHARMACEUTICAL SCIENCES (Mack Publishing Company), THE HANDBOOK OF PHARMACEUTICAL ADDITIVES (Gower Publishing Limited), and THE HANDBOOK OF PHARMACEUTICAL EXCIPIENTS (the American Pharmaceutical Association and the Pharmaceutical Press).

The compositions of the disclosure are prepared using techniques and methods known to those skilled in the art. Some methods commonly used in the art are described in REMINGTON'S PHARMACEUTICAL SCIENCES (Mack Publishing Company).

In one embodiment, the disclosure is directed to a solid oral dosage form such as a tablet or capsule comprising a therapeutically effective amount of a compound of general formula (I), or a pharmaceutically acceptable salt of the foregoing, and a diluent or filler. Suitable diluents and fillers include lactose, sucrose, dextrose, mannitol, sorbitol, starch (e.g., corn starch, potato starch, and pre-gelatinized starch), cellulose and its derivatives, (e.g., microcrystalline cellulose), calcium sulfate, and dibasic calcium phosphate. The solid oral dosage form may further comprise a binder. Suitable binders include starch (e.g., corn starch, potato starch, and pre-gelatinized starch) gelatin, acacia, sodium alginate, alginic acid, tragacanth, guar gum, povidone, and cellulose and its derivatives (e.g., microcrystalline cellulose). The solid oral dosage form may further comprise a disintegrant. Suitable disintegrants include crospovidone, sodium starch glycolate, croscarmelose, alginic acid, and sodium carboxymethyl cellulose. The solid oral dosage form may further comprise a lubricant. Suitable lubricants include stearic acid, magnesium stearate, calcium stearate, and talc.

Where appropriate, dosage unit formulations for oral administration can be microencapsulated. The composition can also be prepared to prolong or sustain the release as, for example, by coating or embedding particulate material in polymers, wax, or the like.

The compounds disclosed herein may also be coupled with soluble polymers as targetable drug carriers. Such polymers can include polyvinylpyrrolidone, pyrancopolymer, polyhydroxypropylmethacrylamidephenol, polyhydroxyethylaspartamidephenol, or polyethyleneoxidepolylysine substituted with palmitoyl residues. Furthermore, the compounds of the disclosure may be coupled to a class of biodegradable polymers useful in achieving controlled release of a drug, for example polylactic acid, polyepsilon caprolactone, polyhydroxy butyric acid, polyorthoesters, polyacetals, polydihydropyrans, polycyanacrylates, and cross-linked or amphipathic block copolymers of hydrogels.

In one embodiment, the disclosure is directed to a liquid oral dosage form. Oral liquids such as solutions, syrups, and elixirs can be prepared in dosage unit form so that a given quantity contains a predetermined amount of a compound or a pharmaceutically acceptable salt thereof disclosed herein. Syrups can be prepared by dissolving the compound of the disclosure in a suitably flavored aqueous solution; elixirs are prepared through the use of a non-toxic alcoholic vehicle. Suspensions can be formulated by dispersing a compound disclosed herein in a non-toxic vehicle. Solubilizers and emulsifiers such as ethoxylated isostearyl alcohols and polyoxy ethylene sorbitol ethers, preservatives, flavor additives such as peppermint oil, or other natural sweeteners or saccharin or other artificial sweeteners and the like can also be added.

In one embodiment, the disclosure is directed to compositions for parenteral administration. Compositions adapted for parenteral administration include aqueous and non-aqueous sterile injection solutions that may contain antioxidants, buffers, bacteriostats, and solutes that render the formulation isotonic with the blood of the intended recipient; and aqueous and non-aqueous sterile suspensions that may include suspending agents and thickening agents. The compositions may be presented in unit-dose or multi-dose containers, for example sealed ampoules and vials, and may be stored in a freeze-dried (lyophilized) condition, requiring only the addition of the sterile liquid carrier, for example water for injections, immediately prior to use. Extemporaneous injection solutions and suspensions may be prepared from sterile powders, granules, and tablets.

Combinations

The compounds of general formula (I), and/or pharmaceutically acceptable salts of the foregoing, may be administered in combination with one or more additional active agents. In embodiments, one or more compounds of general formula (I), or one or more pharmaceutically acceptable salts of the foregoing, and the one or more additional active agents may be co-administered. The additional active agent(s) may be administered in a single dosage form with the compound of general formula (I), or pharmaceutically acceptable salt of the foregoing, or the additional active agent(s) may be administered in separate dosage form(s) from the dosage form containing the compound of general formula (I), or pharmaceutically acceptable salt of the foregoing.

The additional active agent(s) may be provided as a pharmaceutically acceptable salt, where appropriate.

The additional active agent(s) may be one or more agents selected from the group consisting of STING agonist compounds, anti-viral compounds, antigens, adjuvants, anti-cancer agents, CTLA-4, LAG-3 and PD-1 pathway antagonists, lipids, liposomes, peptides, cytotoxic agents, chemotherapeutic agents, immunomodulatory cell lines, checkpoint inhibitors, vascular endothelial growth factor (VEGF) receptor inhibitors, topoisomerase II inhibitors, smoothen inhibitors, alkylating agents, anti-tumor antibiotics, anti-metabolites, retinoids, and immunomodulatory agents including but not limited to anti-cancer vaccines. It will be understood that such additional active agent(s) may be provided as a pharmaceutically acceptable salt. It will be understood the descriptions of the above additional active agents may be overlapping. It will also be understood that the treatment combinations are subject to optimization, and it is understood that the best combination to use of the compounds of general formula (I), or pharmaceutically acceptable salts of the foregoing, and one or more additional active agents will be determined based on the individual patient needs.

A compound disclosed herein may be used in combination with one or more other active agents, including but not limited to, other anti-cancer agents that are used in the prevention, treatment, control, amelioration, or reduction of risk of a particular disease or condition (e.g., cell proliferation disorders). In one embodiment, a compound disclosed herein is combined with one or more other anti-cancer agents for use in the prevention, treatment, control amelioration, or reduction of risk of a particular disease or condition for which the compounds disclosed herein are useful. Such other active agents may be administered, by a route and in an amount commonly used therefor, contemporaneously or sequentially with a compound of the present disclosure.

When a compound disclosed herein is used contemporaneously with one or more other active agents, a composition containing such other active agents in addition to the compound disclosed herein is contemplated. Accordingly, the compositions of the present disclosure include those that also contain one or more other active ingredients, in addition to a compound disclosed herein. A compound disclosed herein may be administered either simultaneously with, or before or after, one or more other active agent(s). A compound disclosed herein may be administered separately, by the same or different route of administration, or together in the same pharmaceutical composition as the other agent(s).

Products provided as combinations may include a composition comprising a compound of general formula (I), or a pharmaceutically acceptable salt of the foregoing, and one or more other active agent(s) together in the same pharmaceutical composition, or may include a composition comprising a compound of general formula (I), or a pharmaceutically acceptable salt of the foregoing, and a composition comprising one or more other active agent(s) in separate form, e.g. in the form of a kit or in any form designed to enable separate administration either concurrently or on separate dosing schedules.

The weight ratio of a compound of general formula (I), or a pharmaceutically acceptable salt of the foregoing, to a second active agent may be varied and will depend upon the therapeutically effective dose of each agent. Generally, a therapeutically effective dose of each will be used. Combinations of a compound disclosed herein and other active agents will generally also be within the aforementioned range, but in each case, a therapeutically effective dose of each active agent should be used. In such combinations, the compound disclosed herein and other active agents may be administered separately or in conjunction. In addition, the administration of one element may be prior to, concurrent to, or subsequent to the administration of other agent(s).

In one embodiment, this disclosure provides a composition comprising a compound of general formula (I), or a pharmaceutically acceptable salt of the foregoing, and at least one other active agent as a combined preparation for simultaneous, separate or sequential use in therapy. In one embodiment, the therapy is the treatment of a cell proliferation disorder, such as cancer.

In one embodiment, the disclosure provides a kit comprising two or more separate pharmaceutical compositions, at least one of which contains a compound of general formula (I), or a pharmaceutically acceptable salt of the foregoing. In one embodiment, the kit comprises means for separately retaining said compositions, such as a container, divided bottle, or divided foil packet. An example of such a kit is a blister pack, as typically used for the packaging of tablets, capsules, and the like.

A kit of this disclosure may be used for administration of different dosage forms, for example, oral and parenteral, for administration of the separate compositions at different dosage intervals, or for titration of the separate compositions against one another. To assist with compliance, a kit of the disclosure typically comprises directions for administration.

Disclosed herein is a use of a compound of general formula (I), or a pharmaceutically acceptable salt of the foregoing, for treating a cell proliferation disorder, where the medicament is prepared for administration with another active agent. The disclosure also provides the use of another active agent for treating a cell proliferation disorder, where the medicament is administered with a compound of general formula (I), or a pharmaceutically acceptable salt of the foregoing.

The disclosure also provides the use of a compound of general formula (I), or a pharmaceutically acceptable salt of the foregoing, for treating a cell proliferation disorder, where the patient has previously (e.g., within 24 hours) been treated with another active agent. The disclosure also provides the use of another active agent for treating a cell proliferation disorder, where the patient has previously (e.g., within 24 hours) been treated with a compound of general formula (I), or a pharmaceutically acceptable salt of the foregoing. The second agent may be administered a week, several weeks, a month, or several months after the administration of a compound disclosed herein.

STING agonist compounds that may be used in combination with the compounds of general formula (I), or pharmaceutically acceptable salts of the foregoing, disclosed herein include but are not limited to cyclic di-nucleotide compounds, such as those disclosed, for example, in International Patent Application Publication Nos. WO2014093936, WO2014189805, WO2014189806, WO2015185565, WO2016120305, WO2016096174, WO2016096577, WO2017027645, WO2017027646, WO2017075477, WO2017093933, and WO2018009466.

Anti-viral compounds that may be used in combination with the compounds of general formula (I), or pharmaceutically acceptable salts of the foregoing, disclosed herein include hepatitis B virus (HBV) inhibitors, hepatitis C virus (HCV) protease inhibitors, HCV polymerase inhibitors, HCV NS4A inhibitors, HCV NSSA inhibitors, HCV NS5b inhibitors, and human immunodeficiency virus (HIV) inhibitors. Such anti-viral compounds may be provided as a pharmaceutically acceptable salt, where appropriate.

Antigens and adjuvants that may be used in combination with the compounds of general formula (I), or the pharmaceutically acceptable salts of the foregoing, include B7 costimulatory molecule, interleukin-2, interferon-y, GM-CSF, CTLA-4 antagonists, OX-40/OX-40 ligand, CD40/CD40 ligand, sargramostim, levamisol, vaccinia virus, Bacille Calmette-Guerin (BCG), liposomes, alum, Freund's complete or incomplete adjuvant, detoxified endotoxins, mineral oils, surface active substances such as lipolecithin, pluronic polyols, polyanions, peptides, and oil or hydrocarbon emulsions. Adjuvants, such as aluminum hydroxide or aluminum phosphate, can be added to increase the ability of the vaccine to trigger, enhance, or prolong an immune response. Additional materials, such as cytokines, chemokines, and bacterial nucleic acid sequences, like CpG, a toll-like receptor (TLR) 9 agonist as well as additional agonists for TLR 2, TLR 4, TLR 5, TLR 7, TLR 8, TLR9, including lipoprotein, LPS, monophosphoryllipid A, lipoteichoic acid, imiquimod, resiquimod, and in addition retinoic acid-inducible gene I (RIG-I) agonists such as poly I:C, used separately or in combination with the described compositions are also potential adjuvants. Such antigens and adjuvants may be provided as a pharmaceutically acceptable salt, where appropriate.

CTLA-4 and PD-1 pathways are important negative regulators of immune response. Activated T-cells up-regulate CTLA-4, which binds on antigen-presenting cells and inhibits T-cell stimulation, IL-2 gene expression, and T-cell proliferation; these anti-tumor effects have been observed in mouse models of colon carcinoma, metastatic prostate cancer, and metastatic melanoma. PD-1 binds to active T-cells and suppresses T-cell activation; PD-1 antagonists have demonstrated anti-tumor effects as well. CTLA-4 and PD-1 pathway antagonists that may be used in combination with the compounds of general formula (Ia), the compounds of general formula (I), or the pharmaceutically acceptable salts of the foregoing, disclosed herein, include ipilimumab, tremelimumab, nivolumab, pembrolizumab, CT-011, AMP-224, and MDX-1106.

"PD-1 antagonist" or "PD-1 pathway antagonist" means any chemical compound or biological molecule that blocks binding of PD-L1 expressed on a cancer cell to PD-1 expressed on an immune cell (T-cell, B-cell, or NKT-cell) and preferably also blocks binding of PD-L2 expressed on a cancer cell to the immune-cell expressed PD-1. Alternative names or synonyms for PD-1 and its ligands include: PDCD1, PD1, CD279, and SLEB2 for PD-1; PDCD1L1, PDL1, B7H1, B7-4, CD274, and B7-H for PD-L1; and PDCD1L2, PDL2, B7-DC, Btdc, and CD273 for PD-L2. In any of the treatment method, medicaments and uses of the present disclosure in which a human individual is being treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP_005009. Human PD-L1 and PD-L2 amino acid sequences can be found in NCBI Locus No.: NP_054862 and NP_079515, respectively.

PD-1 antagonists useful in any of the treatment method, medicaments and uses of the present disclosure include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody, or a chimeric antibody and may include a human constant region. In some embodiments, the human constant region is selected from the group consisting of IgG1, IgG2, IgG3, and IgG4 constant regions, and in preferred embodiments, the human constant region is an IgG1 or IgG4 constant region. In some embodiments, the antigen binding fragment is selected from the group consisting of Fab, Fab'-SH, F(ab')$_2$, scFv, and Fv fragments.

Examples of mAbs that bind to human PD-1, and useful in the treatment method, medicaments and uses of the present disclosure, are described in U.S. Pat. Nos. 7,488, 802, 7,521,051, 8,008,449, 8,354,509, and 8,168,757, PCT International Patent Application Publication Nos. WO2004/004771, WO2004/072286, and WO2004/056875, and U.S. Patent Application Publication No. US2011/0271358.

Examples of mAbs that bind to human PD-L1, and useful in the treatment method, medicaments and uses of the present disclosure, are described in PCT International Patent Application Nos. WO2013/019906 and WO2010/077634 A1 and in U.S. Pat. No. 8,383,796. Specific anti-human PD-L1 mAbs useful as the PD-1 antagonist in the treatment method, medicaments and uses of the present disclosure include MPDL3280A, BMS-936559, MEDI4736, MSB0010718C, and an antibody that comprises the heavy chain and light chain variable regions of SEQ ID NO:24 and SEQ ID NO:21, respectively, of WO2013/019906.

Other PD-1 antagonists useful in any of the treatment method, medicaments, and uses of the present disclosure include an immune-adhesion that specifically binds to PD-1 or PD-L1, and preferably specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immune-adhesion molecules that specifically bind to PD-1 are described in PCT International Patent Application Publication Nos. WO2010/027827 and WO2011/066342. Specific fusion proteins useful as the PD-1 antagonist in the treatment method, medicaments, and uses of the present disclosure include AMP-224 (also known as B7-DCIg), which is a PD-L2-FC fusion protein and binds to human PD-1.

Examples of cytotoxic agents that may be used in combination with the compounds of general formula (I), or pharmaceutically acceptable salts of the foregoing, include, but are not limited to, arsenic trioxide (sold under the tradename TRISENOX®), asparaginase (also known as L-asparaginase, and *Erwinia* L-asparaginase, sold under the tradenames ELSPAR® and KIDROLASE®).

Chemotherapeutic agents that may be used in combination with the compounds of general formula (I), or pharmaceutically acceptable salts of the foregoing, disclosed herein include abiraterone acetate, altretamine, anhydrovinblastine, auristatin, bexarotene, bicalutamide, BMS 184476, 2,3,4,5,6-pentafluoro-N-(3-fluoro-4-methoxyphenyl) benzene sulfonamide, bleomycin, N,N-dimethyl-L-valyl-L-valyl-N-methyl-L-valyl-L-prolyl-1-Lproline-t-butylamide, cachectin, cemadotin, chlorambucil, cyclophosphamide, 3',4'-didehydro-4'deoxy-8'-norvin-caleukoblastine, docetaxol, doxetaxel, cyclophosphamide, carboplatin, carmustine, cisplatin, cryptophycin, cyclophosphamide, cytarabine, dacarbazine (DTIC), dactinomycin, daunorubicin, decitabine dolastatin, doxorubicin (adriamycin), etoposide, 5-fluorouracil, finasteride, flutamide, hydroxyurea and hydroxyurea andtaxanes, ifosfamide, liarozole, lonidamine, lomustine (CCNU), MDV3100, mechlorethamine (nitrogen mustard), melphalan, mivobulin isethionate, rhizoxin, sertenef, streptozocin, mitomycin, methotrexate, taxanes, nilutamide, nivolumab, onapristone, paclitaxel, pembrolizumab, prednimustine, procarbazine, RPR109881, stramustine phosphate, tamoxifen, tasonermin, taxol, tretinoin, vinblastine, vincristine, vindesine sulfate, and vinflunine. Such chemotherapeutic agents may be provided as a pharmaceutically acceptable salt, where appropriate.

Examples of vascular endothelial growth factor (VEGF) receptor inhibitors include, but are not limited to, bevacizumab (sold under the trademark AVASTIN), axitinib (described in PCT International Patent Publication No. WO01/002369), Brivanib Alaninate ((S)—((R)-1-(4-(4-Fluoro-2-methyl-1H-indol-5-yloxy)-5-methylpyrrolo[2,1-f][1,2,4]triazin-6-yloxy)propan-2-yl)2-aminopropanoate, also known as BMS-582664), motesanib (N-(2,3-dihydro-3,3-dimethyl-1H-indol-6-yl)-2-[(4-pyridinylmethyl)amino]-3-pyridinecarboxamide. and described in PCT International Patent Application Publication No. WO02/068470), pasireotide (also known as SO 230, and described in PCT International Patent Publication No. WO02/010192), and sorafenib (sold under the tradename NEXAVAR). Such inhibitors may be provided as a pharmaceutically acceptable salt, where appropriate.

Examples of topoisomerase II inhibitors, include but are not limited to, etoposide (also known as VP-16 and Etoposide phosphate, sold under the tradenames TOPOSAR, VEPESID, and ETOPOPHOS), and teniposide (also known as VM-26, sold under the tradename VUMON). Such inhibitors may be provided as a pharmaceutically acceptable salt, where appropriate.

Examples of alkylating agents, include but are not limited to, 5-azacytidine (sold under the trade name VIDAZA), decitabine (sold under the trade name of DECOGEN), temozolomide (sold under the trade names TEMCAD, TEMODAR, and TEMODAL), dactinomycin (also known as actinomycin-D and sold under the tradename COSMEGEN), melphalan (also known as L-PAM, L-sarcolysin, and phenylalanine mustard, sold under the tradename ALKERAN), altretamine (also known as hexamethylmelamine (HMM), sold under the tradename HEXALEN), carmustine (sold under the tradename BCNU), bendamustine (sold under the tradename TREANDA), busulfan (sold under the tradenames BUSULFEX® and MYLERAN®), carboplatin (sold under the tradename PARAPLATIN®), lomustine (also known as CCNU, sold under the tradename CEENU®), cisplatin (also known as CDDP, sold under the tradenames PLATINOL® and PLATINOL®-AQ), chlorambucil (sold under the tradename LEUKERAN®), cyclophosphamide (sold under the tradenames CYTOXAN® and NEOSAR®), dacarbazine (also known as DTIC, DIC and imidazole carboxamide, sold under the tradename DTIC-DOME®), altretamine (also known as hexamethylmelamine (HMM) sold under the tradename HEXALEN®), ifosfamide (sold under the tradename IFEX®), procarbazine (sold under the tradename MATULANE®), mechlorethamine (also known as nitrogen mustard, mustine and mechloroethamine hydrochloride, sold under the tradename MUSTARGEN®), streptozocin (sold under the tradename ZANOSAR®), thiotepa (also known as thiophosphoamide, TESPA and TSPA, and sold under the tradename THIOPLEX®. Such alkylating agents may be provided as a pharmaceutically acceptable salt, where appropriate.

Examples of anti-tumor antibiotics include, but are not limited to, doxorubicin (sold under the tradenames ADRIAMYCIN® and RUBEX®), bleomycin (sold under the tradename LENOXANE®), daunorubicin (also known as dauorubicin hydrochloride, daunomycin, and rubidomycin hydrochloride, sold under the tradename CERUBIDINE®), daunorubicin liposomal (daunorubicin citrate liposome, sold under the tradename DAUNOXOME®), mitoxantrone (also known as DHAD, sold under the tradename NOVANTRONE®), epirubicin (sold under the tradename ELLENCE™), idarubicin (sold under the tradenames IDAMYCIN®, IDAMYCIN PFS®), and mitomycin C (sold under the tradename MUTAMYCIN®). Such anti-tumor antibiotics may be provided as a pharmaceutically acceptable salt, where appropriate.

Examples of anti-metabolites include, but are not limited to, claribine (2-chlorodeoxyadenosine, sold under the tradename LEUSTATIN®), 5-fluorouracil (sold under the tradename ADRUCIL®), 6-thioguanine (sold under the tradename PURINETHOL®), pemetrexed (sold under the tradename ALIMTA®), cytarabine (also known as arabinosylcytosine (Ara-C), sold under the tradename CYTOSAR-U®), cytarabine liposomal (also known as Liposomal Ara-C, sold under the tradename DEPOCYT™), decitabine (sold under the tradename DACOGEN®), hydroxyurea and (sold under the tradenames HYDREA®, DROXIA™ and MYLOCEL™) fludarabine (sold under the tradename FLUDARA®), floxuridine (sold under the tradename FUDR®), cladribine (also known as 2-chlorodeoxyadenosine (2-CdA) sold under the tradename LEUSTATIN™), methotrexate (also known as amethopterin, methotrexate sodium (MTX), sold under the tradenames RHEUMATREX® and TREXALL™), and pentostatin (sold under the tradename NIPENT®). Such anti-metabolites may be provided as a pharmaceutically acceptable salt, where appropriate.

Examples of retinoids include, but are not limited to, alitretinoin (sold under the tradename PANRETIN®), tretinoin (all-trans retinoic acid, also known as ATRA, sold under the tradename VESANOID®), Isotretinoin (13-c/s-retinoic acid, sold under the tradenames ACCUTANE®, AMNESTEEM®, CLARAVIS®, CLARUS®, DECUTAN®, ISOTANE®, IZOTECH®, ORATANE®, ISOTRET®, and SOTRET®), and bexarotene (sold under the tradename TARGRETIN®). Such compounds may be provided as a pharmaceutically acceptable salt, where appropriate.

Activity: STING Biochemical [3H]cGAMP Competition Assay

The individual compounds described in the Examples herein are defined as STING agonists by (i) binding to the STING protein as evidenced by a reduction in binding of tritiated cGAMP ligand to the STING protein by at least 20% at 200 µM (concentration of compound being tested) in a STING Biochemical [3H]cGAMP Competition Assay, and/(ii) demonstrating interferon production with a 6% or greater induction of IFN-β secretion at 30 µM in the THP1 cell assay (where induction caused by cGAMP at 30 uM was set at 100%).

The ability of compounds to bind STING is quantified by the ability to compete with tritiated cGAMP ligand for human STING receptor membrane using a radioactive filter-binding assay. The binding assay employs STING receptor obtained from Hi-Five cell membranes overexpressing full-length HAQ STING prepared in-house and tritiated cGAMP ligand also purified in-house.

The following experimental procedures detail the preparation of specific examples of the instant disclosure. The compounds of the examples are drawn in their neutral forms in the procedures and tables below. In some cases, the compounds were isolated as salts depending on the method used for their final purification and/or intrinsic molecular properties. The examples are for illustrative purposes only and are not intended to limit the scope of the instant disclosure in any way.

EXAMPLES

Abbreviations

2',3'cGAMP, cGAMP 2',3'-cyclic guanosine monophosphate-adenosine monophosphate
Ac Acetyl, $CH_3C(O)$
ACN, MeCN, $CH_3CN$ Acetonitrile
AcOH, HOAc Acetic acid
AMP Adenosine monophosphate
aq Aqueous
ATP Adenosine 5'-triphosphate
BIIC Baculovirus Infected Insect Cell
br Broad
Bu Butyl, $C_4H_9$
cat Catalog number
$CD_3OD$ Deuterium-enriched methyl alcohol, deuterium-enriched methanol
$CDCl_3$ Deuterated trichloromethane
CDI Carbonyl diimidazole
cGAMP Cyclic GMP-AMP synthase
Ci Curie, a non-standard unit of radioactivity; 1 Ci=$3.7 \times 10^{10}$ Bq, where Bq is Becquerel, the SI unit of radioactivity, equivalent to 1 disintegration per second (dps)
CPhos Pd G4 2-Aminobiphenylpalladium methanesulfonate palladium CPhos precatalyst ($4^{th}$ generation precatalyst)
Cy Cyclohexyl
d Doublet
DCE 1,2-Dichloroethane
DCM, $CH_2Cl_2$ Dichloromethane
ddd Doublet of doublet of doublet
ddt Doublet of doublet of triplet
DMAP 4-dimethylaminopyridine
DMEA N,N-dimethyl ethyl amine
DMF N,N-dimethylformamide DMO Dimethyl oxalate
DMSO Dimethylsulfoxide
DMTr 4,4'-dimethoxytrityl
DMTrCl 4,4'-dimethoxytrityl chloride
dq Doublet of quartet
$EC_{50}$ half maximal effective concentration; concentration of a drug, antibody, or toxicant that induces a response halfway between the baseline and maximum after a specified exposure time
EDC (1-Ethyl-3-(3-dimethylaminopropyl)carbodiimide
eq Equivalents
ES Electron spray
Et Ethyl, $CH_3CH_2$
GMP Guanosine 5'-monophosphate
GTP Guanosine 5'-triphosphate
h Hour
HAQ STING Common STING variant containing the three mutations R71H-G230A-R293Q (DNA construct used herein: STING(1-379)R71H,G230A, H232R,R293Q-GG-AviTag-GS-HRV3C-HIS8/pBAC1)
HEPES 2-[4-(2-hydroxyethyl)piperazin-1-yl]ethanesulfonic acid, a zwitterionic organic chemical buffering agent
hept Heptet
Hex Hexanes
HPLC High performance liquid chromatography
$IC_{50}$ half maximal inhibitory concentration; concentration of a drug, antibody, or toxicant required for 50% inhibition of response or binding
Inh Inhibition
LCMS Liquid chromatography-mass spectroscopy
LDA Lithium di-isopropyl amide
m Multiplet
M Molar, moles per liter
m/z Mass-to-charge ratio
M+H Protonated mass, mass measurement produced by mass spectrometry
mCPBA meta-Chloroperoxybenzoic acid
Me Methyl, $CH_3$
min Minute(s)
mM Millimole per liter
mmol Millimole
MOI Multiplicity of infection
NBS N-Bromosuccinimide
nm Nanometer
nM Nanomolar
NMO N-Methylmorpholine N-oxide
NMP N-methyl-2-pyrrolidone
$Pd(Ph_3P)_4$ Tetrakis(triphenyl phosphine) palladium(0)
$Pd_2(dba)_3$ Tris(dibenzylidene acetone) dipalladium(0)
PE Petroleum ether
pfu Plaque-forming unit
prep-HPLC Preparative high performance liquid chromatography
prep-TLC Preparative thin layer liquid chromatography
PSI Pounds per square inch
q Quartet
RPM, rpm Revolutions per minute
RT, rt Room temperature, approximately 25° C.
s Singlet
sat Saturated
SFC Supercritical fluid chromatography
t Triplet
TFA Trifluoroacetic acid
THF Tetrahydrofuran
TLC Thin layer chromatography
TMS Trimethylsilyl
$T_R$ Retention time
TrisCl Tris(hydroxymethyl)aminomethane hydrochloride
v/v Volume/volume
WT STING The wild type (most abundant) variant of STING in humans (DNA construct used herein: STING (1-379)H232R-gg-AviTag-gs-HRV3C-HIS8/pBAC1)
X-Phos 2-Dicyclohexylphosphino-2',4',6'-triisopropylbiphenyl
$\lambda_{em}$ Emission wavelength
$\lambda_{ex}$ Excitation wavelength Preparation 1: Magnesium 3-(tert-butoxy)-3-oxopropanoate

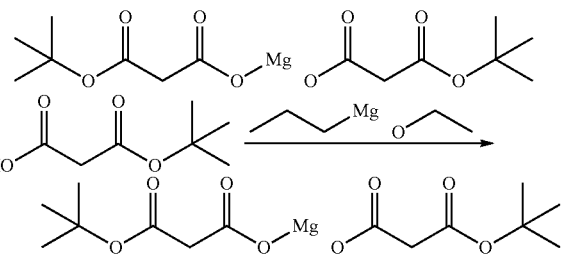

Magnesium ethanolate (3.57 g, 31.2 mmol) was added to a mixture of 3-(tert-butoxy)-3-oxopropanoic acid (10.0 g, 62.4 mmol) in THF (100 mL) at 20° C. The reaction mixture was stirred at 20° C. for 18 hours under Ar. The reaction mixture was then concentrated under reduced pressure. The residue was dried under reduced pressure to afford magnesium 3-(tert-butoxy)-3-oxopropanoate. $^1$H NMR (499 MHz, DMSO-$d_6$) δ 2.96 (s, 4H), 1.39 (s, 18H).

Preparation 2: tert-Butyl 3-(2,3-dimethoxythieno[2,3-b]pyrazin-6-yl)-3-oxopropanoate

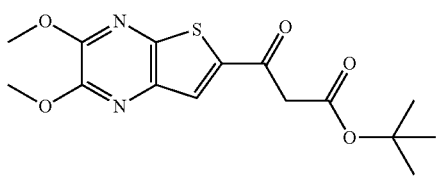 [SMILES: COc1nc2cc(C(=O)CC(=O)OC(C)(C)C)sc2nc1OC]

Step 1:
3-Bromo-5,6-dimethoxypyrazine-2-carbaldehyde

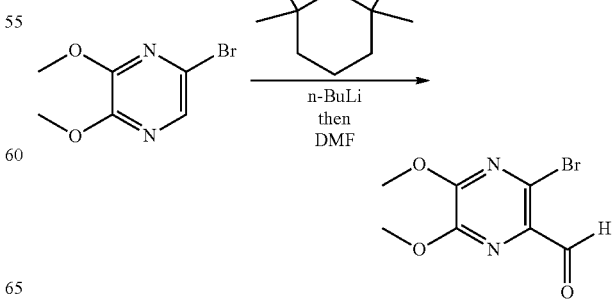

To a solution of 2,2,6,6-tetramethylpiperidine (5.12 mL, 30.1 mmol) in THF (40 mL) at −78° C. was added dropwise a solution of n-BuLi (2.5M in Hex, 11.5 mL, 28.8 mmol). The reaction mixture was stirred for 10 min. at −78° C. and then warmed to 0° C. and stirred for an additional 20 min. The reaction mixture was then cooled back to −78° C., and a solution of 5-bromo-2,3-dimethoxypyrazine (3.00 g, 13.7 mmol) in THF (10 mL) was added over a period of 5 min. The reaction mixture was stirred at −78° C. for 1 hour and then quenched with DMF (1.06 mL, 13.7 mmol). The reaction mixture was warmed to 0° C. and stirred for an additional 20 min. AcOH (3.0 mL) was added at 0° C., and the reaction mixture was warmed to RT and stirred overnight. The mixture was diluted with EtOAc (300 mL) and then washed with $H_2O$ (2×150 mL) and brine. The organic layer was separated, dried over $Na_2SO_4$, filtered, and concentrated under reduced pressure. The residue was purified by silica gel chromatography (eluting EtOAc in Hex) to afford 3-bromo-5,6-dimethoxypyrazine-2-carbaldehyde. LCMS ($C_7H_8BrN_2O_3$) (ES, m/z): 247, 249 [M+H]$^+$. $^1$H NMR (500 MHz, CDCl$_3$) δ 10.19 (s, 1H), 4.17 (s, 3H), 4.14 (s, 3H).

Step 2: tert-Butyl 2,3-dimethoxythieno[2,3-b]pyrazine-6-carboxylate

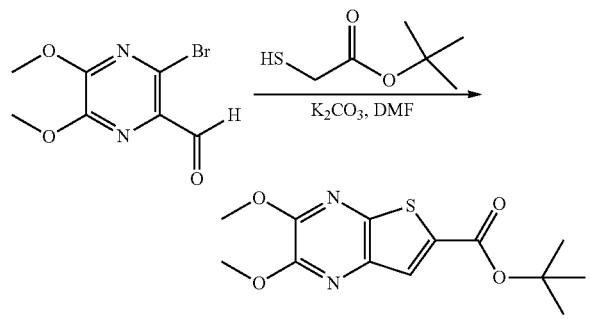

tert-Butyl 2-sulfanylacetate (42 μL, 2.92 mmol) and DMF (2.9 mL) were added to 3-bromo-5,6-dimethoxypyrazine-2-carbaldehyde (650 mg, 2.63 mmol) at RT. $K_2CO_3$ (1090 mg, 7.89 mmol) was then added portion-wise to the reaction mixture at RT. The reaction mixture was heated to 80° C. and stirred overnight. The reaction mixture was then cooled to RT, diluted with Et$_2$O, and quenched with $H_2O$. The reaction mixture was extracted with Et$_2$O, and the combined organics were washed with brine, dried over $Na_2SO_4$, filtered, and concentrated under reduced pressure. The residue was purified by silica gel chromatography (eluting EtOAc in Hex) to yield tert-butyl 2,3-dimethoxythieno[2,3-b]pyrazine-6-carboxylate. LCMS ($C_{13}H_{17}N_2O_4S$) (ES, m/z): 297 [M+H]$^+$. $^1$H NMR (500 MHz, DMSO-d$_6$) δ 7.89 (s, 1H), 4.02 (s, 3H), 3.99 (s, 3H), 1.55 (s, 9H).

Step 3: 2,3-Dimethoxythieno[2,3-b]pyrazine-6-carboxylic Acid

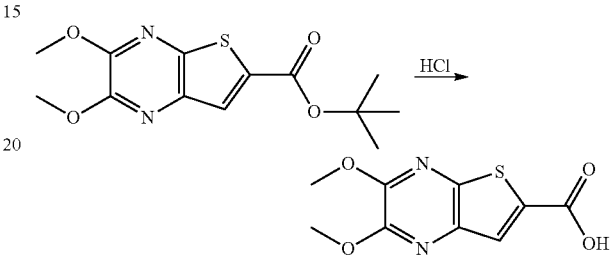

To a stirred solution of tert-butyl 2,3-dimethoxythieno[2,3-b]pyrazine-6-carboxylate (400 mg, 1.35 mmol) in DCM (6.0 mL) was added HCl (4.0M in dioxane, 1.7 mL, 6.8 mmol) at RT. The reaction mixture was stirred overnight at RT, and then diluted by the dropwise addition of Hex (50 mL) and stirred for an additional 1 hour at RT. The reaction mixture was filtered, and the collected material were washed with Hex (2×10 mL) and dried under reduced pressure to afford 2,3-dimethoxythieno[2,3-b]pyrazine-6-carboxylic acid. LCMS ($C_9H_9N_2O_4S$) (ES, m/z): 241 [M+H]$^+$. $^1$H NMR (500 MHz, DMSO-d$_6$) δ 12.71 (br s, 1H), 7.90 (s, 1H), 4.03 (s, 3H), 3.99 (s, 3H).

Step 4: tert-Butyl 3-(2,3-dimethoxythieno[2,3-b]pyrazin-6-yl)-3-oxopropanoate

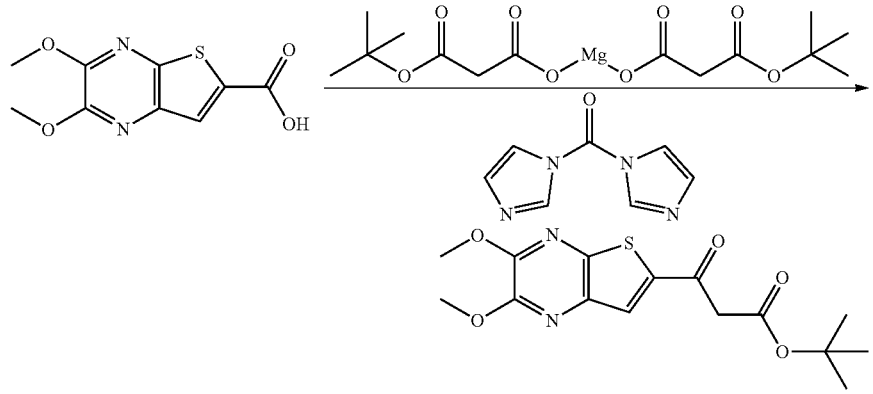

A mixture of 2,3-dimethoxythieno[2,3-b]pyrazine-6-carboxylic acid (80 mg, 0.33 mmol) and CDI (324 mg, 2.00 mmol) in THF (5.5 mL) was stirred at RT for 3 hours. Magnesium bis(3-tert-butoxy-3-oxopropanoate) (628 mg, 1.83 mmol) was added, and the resulting mixture was stirred overnight at RT. The reaction mixture was concentrated under reduced pressure. The residue was purified by silica gel chromatography (eluting (25% EtOH in EtOAc) in Hex) to afford tert-butyl 3-(2,3-dimethoxythieno[2,3-b]pyrazin-6-yl)-3-oxopropanoate. LCMS ($C_{15}H_{19}N_2O_5S$) (ES, m/z): 339 [M+H]$^+$. $^1$H NMR (500 MHz, DMSO-d$_6$) δ 8.32 (s, 1H), 4.13 (s, 2H), 4.04 (s, 3H), 4.00 (s, 3H), 1.41 (s, 9H).

Preparation 3: 5,6-Dimethoxythieno[3,2-b]pyridine-2-carboxylic Acid

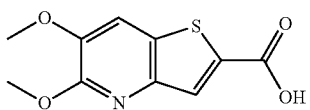 [SMILES: COc1cc2sc(C(=O)O)cc2nc1OC]

Step 1: tert-Butyl 5,6-dimethoxythieno[3,2-b]pyridine-2-carboxylate

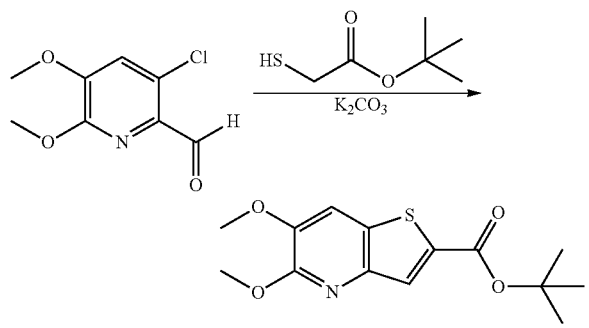

K$_2$CO$_3$ (1180 mg, 8.56 mmol) was added to a mixture of 3-chloro-5,6-dimethoxypicolinaldehyde (575 mg, 2.86 mmol) and tert-butyl 2-sulfanylacetate (0.456 mL, 3.14 mmol) in DMF (8.3 mL) at RT. The reaction mixture was stirred and heated to 60° C. for 3 days. The reaction mixture was cooled to RT, and then diluted with Et$_2$O and H$_2$O. The organic layer was separated, washed with brine, dried over Na$_2$SO$_4$, filtered, and concentrated under reduced pressure. The residue was purified by silica gel chromatography (eluting EtOAc in Hex) to afford tert-butyl 5,6-dimethoxythieno[3,2-b]pyridine-2-carboxylate. $^1$H NMR (499 MHz, DMSO-d$_6$) δ 7.95 (s, 1H), 7.84 (s, 1H), 3.93 (s, 3H), 3.87 (s, 3H), 1.54 (s, 9H).

Step 2: 5,6-dimethoxythieno[3,2-b]pyridine-2-carboxylic Acid

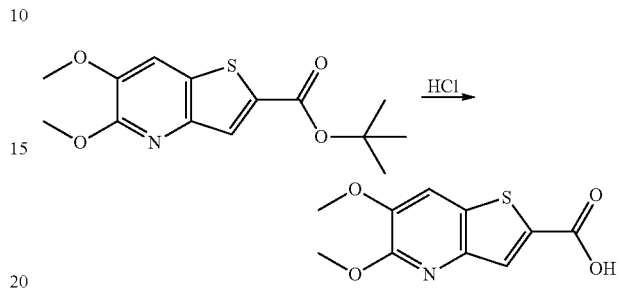

HCl (4.0M in dioxane, 2.1 mL, 8.4 mmol) was added to a solution of tert-butyl 5,6-dimethoxythieno[3,2-b]pyridine-2-carboxylate (493 mg, 1.67 mmol) in DCM (7.4 mL) at RT. The reaction mixture was stirred overnight at RT, and then diluted by the dropwise addition of Hex (50 mL). The mixture was stirred for 1 hour and filtered. The collected materials were washed with Hex (2×10 mL) and then dried under reduced pressure to afford 5,6-dimethoxythieno[3,2-b]pyridine-2-carboxylic acid. LCMS ($C_{10}H_{10}NO_4S$) (ES, m/z): 240 [M+H]$^+$. $^1$H NMR (499 MHz, DMSO-d$_6$) δ 7.97 (s, 1H), 7.85 (s, 1H), 3.95 (s, 3H), 3.88 (s, 3H).

Preparation 4: tert-Butyl 3-(5,6-dimethoxythieno[3,2-b]pyridin-2-yl)-3-oxopropanoate

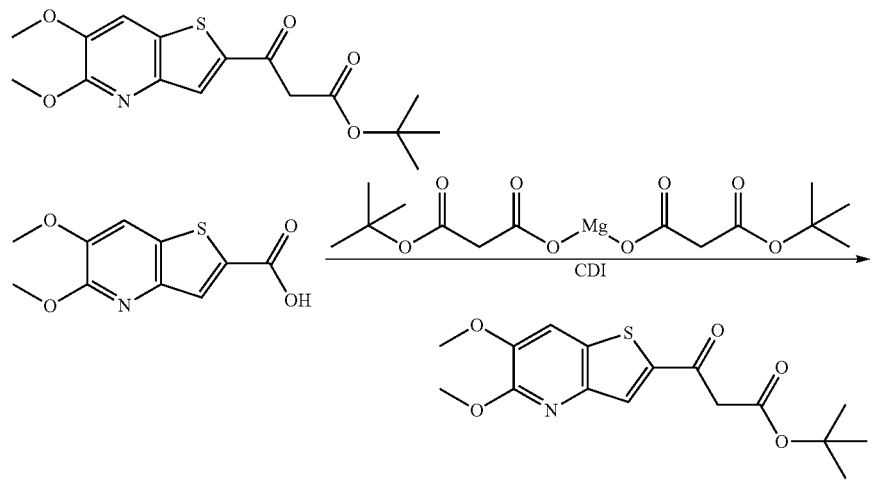

CDI (508 mg, 3.13 mmol) was added to a mixture of 5,6-dimethoxythieno[3,2-b]pyridine-2-carboxylic acid (500 mg, 2.09 mmol) in THF (5 mL). The reaction mixture was stirred at RT for 3 hours. The reaction mixture was added to a separate flask containing magnesium 3-(tert-butoxy)-3-oxopropanoate (1220 mg, 3.55 mmol). The reaction mixture was diluted with additional THF (4 mL) and was stirred overnight at RT. The reaction mixture was then heated to 50° C. for 1 hour. The reaction mixture was cooled to RT and diluted with H₂O (20 mL). Sodium citrate tribasic dihydrate (2 g) and EtOAc (50 mL) were added. The organic layer was separated, and the aqueous layer was extracted with additional EtOAc. The organic layers were combined, washed with brine, dried over anhydrous Na$_2$SO$_4$, filtered, and concentrated under reduced pressure. The residue was purified via silica gel chromatography (eluting EtOAc in Hex) to afford tert-butyl 3-(5,6-dimethoxythieno[3,2-b]pyridin-2-yl)-3-oxopropanoate. LCMS (C$_{16}$H$_{20}$NO$_5$S) (ES, m/z): 338 [M+H]$^+$. $^1$H NMR (500 MHz, CDCl$_3$) δ 7.97 (s, 1H), 7.44 (s, 1H), 4.13 (s, 3H), 3.99 (s, 3H), 3.92 (s, 2H), 1.48 (s, 9H).

Example 1: 4-(5,6-Dimethoxybenzo[d]thiazol-2-yl)-4-oxobutanoic Acid

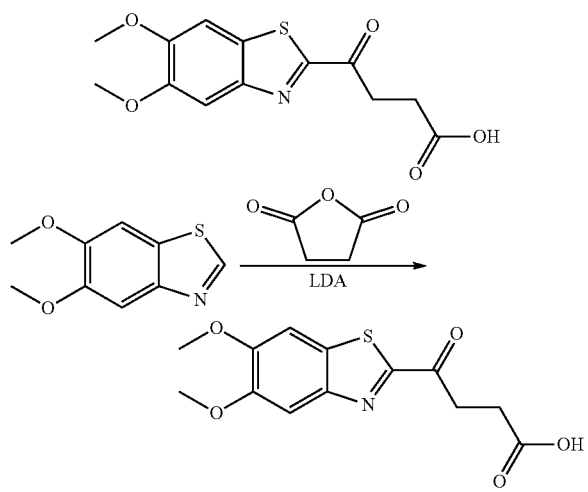

LDA (2.0M in THF, 0.61 mL, 1.22 mmol) was added dropwise to a mixture of 5,6-dimethoxybenzo[d]thiazole (200 mg, 1.02 mmol) in THF (5.0 mL) at −78° C. under N$_2$. The reaction mixture was stirred at −78° C. for 1 hour. A mixture of succinic anhydride (123 mg, 1.22 mmol) in THF (2.0 mL) was then added dropwise to the reaction mixture at −78° C. The reaction mixture was warmed to RT and stirred for 2 hours. A solution of sat aq NH$_4$Cl (1.0 mL) and H$_2$O (5.0 mL) were then added to the reaction mixture. The reaction mixture was extracted with EtOAc (3×30 mL). The organic layers were combined, washed with brine (20 mL), dried over MgSO$_4$, filtered, and concentrated under reduced pressure. The residue was purified by reverse phase HPLC (eluting ACN in H$_2$O with 0.1% TFA) to afford 4-(5,6-dimethoxybenzo[d] thiazol-2-yl)-4-oxobutanoic acid. LCMS (C$_{13}$H$_{14}$NO$_5$S) (ES, m/z): 296 [M+H]$^+$. $^1$H NMR (400 MHz, DMSO-d$_6$) δ 7.76 (s, 1H), 7.75 (s, 1H), 3.89 (s, 3H), 3.88 (s, 3H), 3.40-3.34 (m, 2H), 2.67-2.63 (m, 2H).

Example 2: 4-(5,6-Dimethoxy-1,3-benzothiazol-2-yl)-2-methyl-4-oxobutanoic Acid

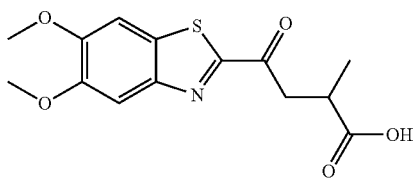

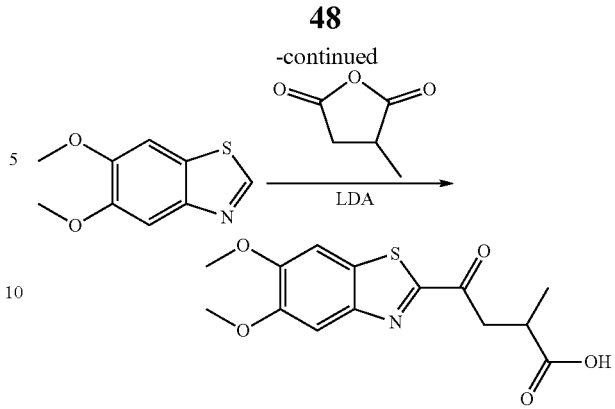

5,6-dimethoxybenzo[d]thiazole (1.58 g, 8.09 mmol) was added to a sealed tube and back evacuated with N$_2$ (2×). THF (40 mL) was added, and the reaction mixture was cooled to −78° C. n-BuLi (1.5M in Hex, 5.6 mL, 8.9 mmol) was added, and the reaction mixture was stirred at −78° C. for 30 min. 3-methyldihydrofuran-2,5-dione (1.02 g, 8.90 mmol) was added, and the reaction mixture was allowed to warm to RT over a period of 4 hours. HCl (1N) was added until the aqueous layer was pH~4. The aqueous layer was then extracted with EtOAc (3×). The organic layers were combined, dried over MgSO$_4$, filtered, and concentrated under reduced pressure. The residue was purified by reverse phase chromatography (eluting ACN/H$_2$O with 0.05% TFA). The fractions containing all product isomers were combined, diluted with H$_2$O, and extracted with EtOAc (3×). The organics were combined, dried over MgSO$_4$, filtered, and concentrated under reduced pressure. The racemic mixture was resolved by Chiral-SFC (CHIRACEL OJ-H (250 mm×21 mm), 25% MeOH in CO$_2$) to afford four peaks. Concentration of the third eluting peak afforded 4-(5,6-dimethoxy-1,3-benzothiazol-2-yl)-2-methyl-4-oxobutanoic acid. LCMS (C$_{14}$H$_{16}$NO$_5$S) (ES, m/z): 310 [M+H]$^+$. $^1$H NMR (500 MHz, MeOD-d$_4$) δ 7.65 (s, 1H), 7.59 (s, 1H), 3.96 (s, 3H), 3.97 (s, 3H), 3.69 (dd, J=18 Hz, 8.8 Hz, 1H), 3.28 (dd, J=18 Hz, 5.5 Hz, 1H), 3.15-3.08 (m, 1H), 1.33 (d, J=7.3 Hz, 3H).

Example 3: (S)-4-(5-Bromo-6-methoxybenzo[d]thiazol-2-yl)-2-methyl-4-oxobutanoic Acid

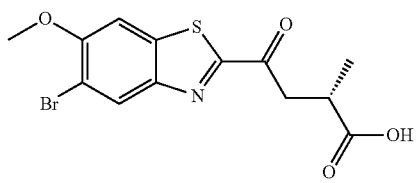 [SMILES: COc1cc2sc(C(=O)C[C@H](C)C(=O)O)nc2cc1Br]

Step 1: Methyl 2-((3-bromo-4-methoxyphenyl)amino)-2-oxoacetate

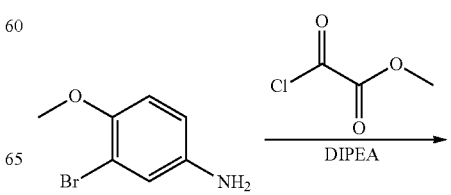

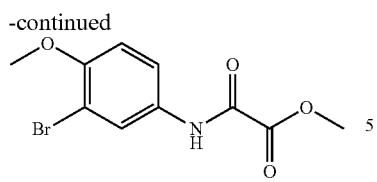

Methyl 2-chloro-2-oxoacetate (1.93 mL, 20.8 mmol) was added dropwise over a period of 5 min to a stirring mixture of 3-bromo-4-methoxyaniline (4.00 g, 19.8 mmol), N-ethyl-N-isopropylpropan-2-amine (4.03 mL, 22.8 mmol), and $CH_2Cl_2$ (100 mL) at 0° C. The reaction mixture was stirred for an additional 30 min. The reaction mixture was diluted with $H_2O$ (150 mL) and then extracted with DCM (2×100 mL). The organic layers were combined, dried over $MgSO_4$, filtered, and concentrated under reduced pressure to afford methyl 2-((3-bromo-4-methoxyphenyl)amino)-2-oxoacetate that was used without purification. $^1$H NMR (499 MHz, $CDCl_3$) δ 8.77 (s, 1H), 7.85 (d, J=2.2 Hz, 1H), 7.63 (dd, J=8.8 Hz, 2.2 Hz, 1H), 6.92 (d, J=8.9 Hz, 1H), 3.99 (s, 3H), 3.91 (s, 3H).

Step 2: Methyl 2-((3-bromo-4-methoxyphenyl)amino)-2-thioxoacetate

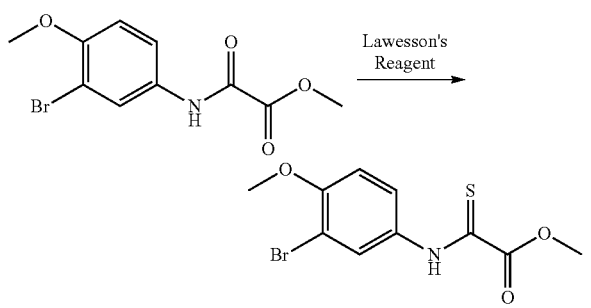

Lawesson's reagent (1.21 g, 2.98 mmol) was added to a mixture of methyl 2-((3-bromo-4-methoxyphenyl)amino)-2-oxoacetate (1.56 g, 5.41 mmol) in toluene (50 mL). The reaction mixture was stirred and heated at 85° C. for 17 hours. The reaction mixture was cooled, filtered, and washed with DCM. The filtrate was concentrated under reduced pressure. The residue was purified by silica gel chromatography (eluting EtOAC in DCM) to afford methyl 2-((3-bromo-4-methoxyphenyl)amino)-2-thioxoacetate. LCMS ($C_{10}H_{11}BrNO_3S$) (ES, m/z): 304, 306 [M+H]$^+$. $^1$H NMR (499 MHz, $CDCl_3$) δ 10.48 (s, 1H), 8.38-8.12 (m, 1H), 8.04-7.85 (m, 1H), 6.96 (d, J=8.9 Hz, 1H), 4.01 (s, 3H), 3.94 (s, 3H).

Step 3: 5-Bromo-6-methoxybenzo[d]thiazole-2-carboxylic Acid

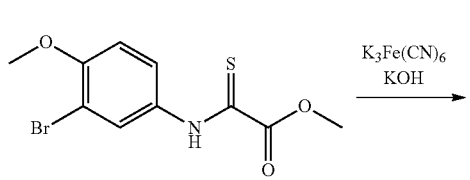

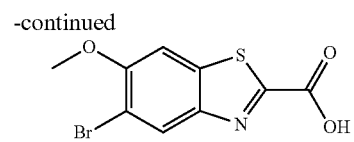

KOH (2N, 20 mL, 40 mmol) was added to a mixture of methyl 2-((3-bromo-4-methoxyphenyl)amino)-2-thioxoacetate (1.01 g, 3.32 mmol) in $CH_2Cl_2$ (10 mL). The reaction mixture was stirred for 10 min. at RT. The reaction mixture was partially concentrated under reduced pressure, and the resulting mixture was then stirred vigorously. A solution of potassium ferricyanide(III) hydrate (3.46 g, 9.96 mmol) in $H_2O$ (20 mL) was added to the reaction mixture. The reaction mixture was stirred for 10 min. The reaction mixture was acidified to pH~2 with HCl (2N). The reaction mixture was diluted with $H_2O$ (50 mL). The reaction mixture was stirred vigorously for 16 hours. The reaction mixture was filtered, and the collected materials were washed with $H_2O$ (2×20 mL), ACN (2×10 mL), and $Et_2O$ (10 mL). The washed materials were dried under reduced pressure to afford 5-bromo-6-methoxybenzo[d]thiazole-2-carboxylic acid that was used without purification. $^1$H NMR (499 MHz, DMSO-$d_6$) δ 8.42 (s, 1H), 7.94 (s, 1H), 3.95 (s, 3H).

Step 4: 5-Bromo-6-methoxybenzo[d]thiazole-2-carbonyl Chloride

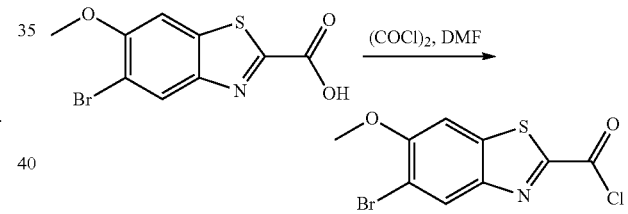

A mixture of 5-bromo-6-methoxybenzo[d]thiazole-2-carboxylic acid (100 mg, 0.35 mmol) in $CH_2Cl_2$ (2 mL) was stirred and cooled to 0° C. DMF (0.005 mL, 0.07 mmol) and $(COCl)_2$ (0.064 mL, 0.73 mmol) were added to the reaction mixture in that order at 0° C. The reaction mixture was warmed to RT and stirred for an additional 20 min. The reaction mixture was concentrated under reduced pressure to afford 5-bromo-6-methoxybenzo[d]thiazole-2-carbonyl chloride, which was used without purification.

Step 5: Methyl (S)-4-(5-bromo-6-methoxybenzo[d]thiazol-2-yl)-2-methyl-4-oxobutanoate

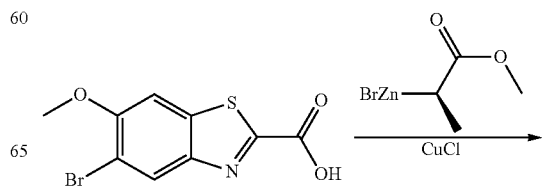

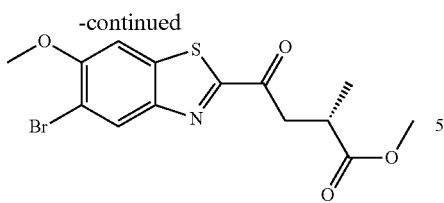

A mixture of CuCl (38 mg, 0.38 mmol) in THF (0.25 mL) was sparged with $N_2$. The reaction mixture was stirred and cooled to 0° C. (R)-(3-methoxy-2-methyl-3-oxopropyl) zinc (II) bromide (0.50M in THF, 2.2 mL, 1.1 mmol) was added dropwise to the reaction mixture over a period of 2 min. The reaction mixture was stirred for 10 min. A solution of 5-bromo-6-methoxybenzo[d]thiazole-2-carbonyl chloride (106 mg, 0.232 mmol) in degassed NMP (2 mL) was added to the reaction mixture over a period of 10 min. The reaction mixture was stirred for an additional 10 min. The reaction mixture was quenched by the dropwise addition of concentrated aqueous $NH_3$ (2 mL). The reaction mixture was diluted with EtOAc (30 mL) and washed with $H_2O$ (3×40 mL). The organic layers were separated, dried over $Na_2SO_4$, filtered, and concentrated under reduced pressure. The residue was purified by silica gel chromatography (eluting EtOAc in Hex) to afford (S)-methyl 4-(5-bromo-6-methoxybenzo[d] thiazol-2-yl)-2-methyl-4-oxobutanoate. LCMS ($C_{14}H_{15}BrNO_4S$) (ES, m/z): 372, 374 [M+H]$^+$. $^1$H NMR (499 MHz, CDCl$_3$) δ 8.37 (s, 1H), 7.39 (s, 1H), 4.02 (s, 3H), 3.78-3.73 (m, 1H), 3.72 (s, 3H), 3.31 (dd, J=18.1 Hz, 5.1 Hz, 1H), 3.23-3.15 (m, 1H), 1.34 (d, J=7.1 Hz, 3H).

Step 6: (S)-4-(5-Bromo-6-methoxybenzo[d]thiazol-2-yl)-2-methyl-4-oxobutanoic Acid

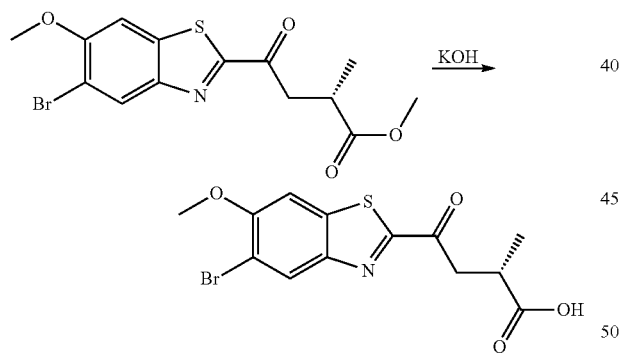

KOH (0.50M in $H_2O$, 0.27 mL, 0.13 mmol) was added dropwise to a stirred mixture of (S)-methyl 4-(5-bromo-6-methoxybenzo[d]thiazol-2-yl)-2-methyl-4-oxobutanoate (24.8 mg, 0.0670 mmol) in 2-propanol (0.5 mL). The reaction mixture was stirred for an additional 15 min at RT. The reaction mixture was acidified with HCl (1.0N) to pH~2. The reaction mixture was stirred for 5 min. The reaction mixture was filtered, and the collected materials were washed with $H_2O$ (3×2 mL). The washed materials were dissolved in ~2 mL of DMSO and then purified prep-HPLC (eluting ACN/$H_2O$ with 0.1% TFA) to afford (S)-4-(5-bromo-6-methoxybenzo[d]thiazol-2-yl)-2-methyl-4-oxobutanoic acid. LCMS ($C_{13}H_{13}BrNO_4S$) (ES, m/z): 358, 360 [M+H]$^+$. $^1$H NMR (499 MHz, DMSO-d$_6$) δ 12.31 (s, 1H), 8.53 (s, 1H), 7.99 (s, 1H), 3.97 (s, 3H), 3.59 (dd, J=18.1 Hz, 8.9 Hz, 1H), 3.22 (dd, J=18.1 Hz, 5.0 Hz, 1H), 3.01-2.93 (m, 1H), 1.22 (d, J=7.2 Hz, 3H).

Example 4: 4-(4-Fluoro-5,6-dimethoxybenzo[d]thiazol-2-yl)-2-methyl-4-oxobutanoic Acid

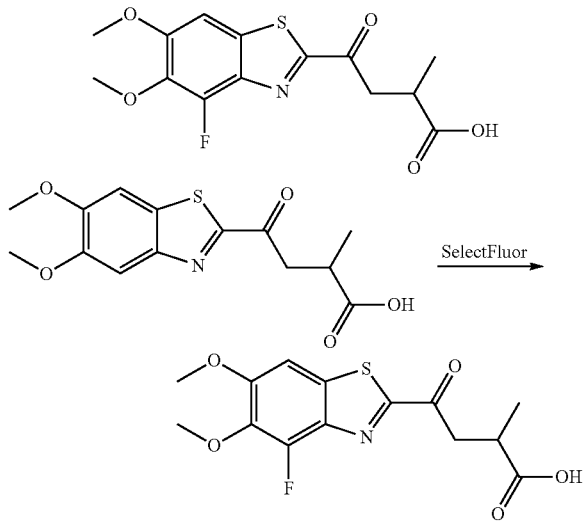

SelectFluor (82 mg, 0.23 mmol) was added to a mixture of 4-(5,6-dimethoxybenzo[d]thiazol-2-yl)-2-methyl-4-oxobutanoic acid (Example 2) (34 mg, 0.11 mmol) in ACN (1 mL). The mixture was stirred at 85° C. for 16 hours. The reaction mixture was cooled to RT and then concentrated under reduced pressure. The residue was purified by reverse phase HPLC (eluting ACN in $H_2O$ with 0.1% TFA) to afford 4-(4-fluoro-5,6-dimethoxybenzo[d]thiazol-2-yl)-2-methyl-4-oxobutanoic acid. LCMS ($C_{14}H_{15}FNO_5S$) (ES, m/z) 328 [M+H]$^+$. $^1$H NMR (499 MHz, DMSO-d$_6$) δ 12.32 (s, 1H), 7.76 (s, 1H), 3.96 (s, 3H), 3.92 (s, 3H), 3.62 (dd, J=18.1 Hz, 8.8 Hz, 1H), 3.24 (dd, J=18.1 Hz, 4.5 Hz, 1H), 3.03-2.92 (m, 1H), 1.24 (d, J=7.0 Hz, 3H).

Example 5: 4-(5,6-Dimethoxythieno[2,3-b]pyridin-2-yl)-4-oxobutanoic Acid

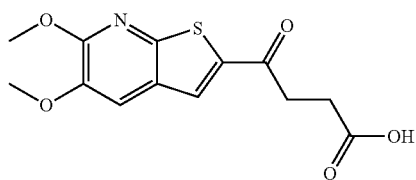 [SMILES: COc1cc2cc(C(=O)CCC(=O)O)sc2nc1OC]

Step 1: 2,3-Dimethoxy-5-vinylpyridine

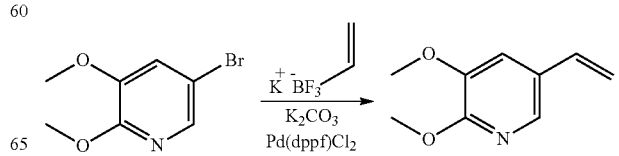

A mixture of 5-bromo-2,3-dimethoxypyridine (1.50 g, 6.88 mmol), potassium trifluoro(vinyl)borate (1.84 g, 13.8 mmol), [1,1'-bis (diphenylphosphino) ferrocene] dichloropalladium (II) (0.503 g, 0.688 mmol), and K$_2$CO$_3$ (2.85 g, 20.6 mmol) in dioxane (15 mL) and H$_2$O (1.5 mL) was degassed and backfilled with N$_2$ three times at 25° C. The reaction mixture was stirred and heated to 80° C. for 12 hours. The reaction mixture was diluted with H$_2$O (20 mL) and EtOAc (20 mL). The reaction mixture was then extracted with EtOAc (3×20 mL). The organic layers were combined, washed with brine (20 mL), dried over MgSO$_4$, filtered, and concentrated under reduced pressure. The residue was purified by silica gel chromatography (eluting EtOAc in PE) to afford 2,3-dimethoxy-5-vinylpyridine. LCMS (C$_9$H$_{12}$NO$_2$) (ES, m/z): 166 [M+H]$^+$. $^1$H NMR (400 MHz, MeOD-d$_4$) δ 7.63 (d, J=1.6 Hz, 1H), 7.36 (d, J=1.8 Hz, 1H), 6.73-6.63 (m, 1H), 5.73 (d, J=17.6 Hz, 1H), 5.22 (d, J=11.0 Hz, 1H), 3.93 (s, 3H), 3.86 (s, 3H).

Step 2: 5,6-Dimethoxynicotinaldehyde

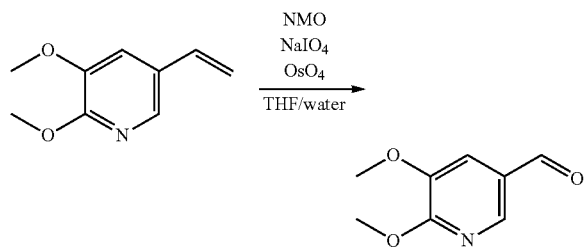

NMO (3.83 g, 32.7 mmol) and OSO$_4$ (0.040M in H$_2$O, 42 mL, 1.7 mmol) were added to a mixture of 2,3-dimethoxy-5-vinylpyridine (2.70 g, 16.3 mmol) in THF (60 mL) and H$_2$O (15 mL). The reaction mixture was stirred at RT for 30 min. NaIO$_4$ (6.99 g, 32.7 mmol) was added, and the reaction mixture was stirred at RT for 12 hours. The reaction mixture was diluted with H$_2$O (50 mL) and EtOAc (50 mL). The reaction mixture was extracted with EtOAc (3×50 mL). The organic layers were combined, washed with brine (50 mL), dried over MgSO$_4$, filtered, and concentrated under reduced pressure. The residue was purified by silica gel chromatography (eluting EtOAc in PE) to afford 5,6-dimethoxynicotinaldehyde. LCMS (C$_8$H$_{10}$NO$_3$) (ES, m/z): 168 [M+H]$^+$. $^1$H NMR (400 MHz, CDCl$_3$-d) δ=9.94 (s, 1H), 8.21 (d, J=1.8 Hz, 1H), 7.48 (d, J=1.8 Hz, 1H), 4.12 (s, 3H), 3.94 (s, 3H).

Step 3: (5,6-Dimethoxypyridin-3-yl)methanol

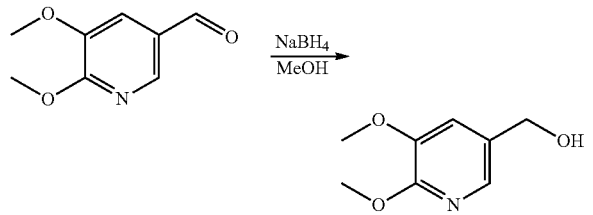

NaBH$_4$ (267 mg, 7.02 mmol) was added to a mixture of 5,6-dimethoxynicotinaldehyde (490 mg, 2.93 mmol) in MeOH (13 mL) and was stirred at RT for 1 hour. The reaction mixture was concentrated under reduced pressure and then diluted with H$_2$O (5.0 mL). The mixture was extracted with EtOAc (3×3 mL). The organic layers were combined, dried over MgSO$_4$, filtered, and concentrated under reduced pressure to afford (5,6-dimethoxypyridin-3-yl)methanol that was used without purification.

Step 4: (2-Bromo-5,6-dimethoxypyridin-3-yl)methanol

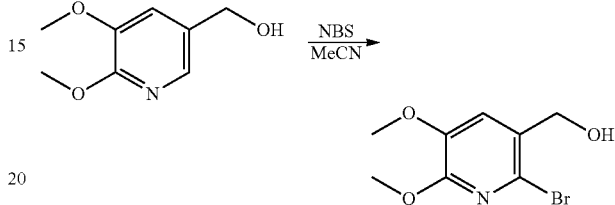

NBS (968 mg, 5.44 mmol) was added to a mixture of (5,6-dimethoxypyridin-3-yl)methanol (610 mg, 3.61 mmol) in AcOH (0.05 mL) and ACN (20 mL). The reaction mixture was stirred at RT for 7 hours. The reaction mixture was quenched with H$_2$O (25 mL) and extracted with EtOAc (3×26 mL). The organic layers were combined, dried over MgSO$_4$, filtered, and concentrated under reduced pressure. The residue was purified by silica gel chromatography (eluting EtOAc in PE) to afford (2-bromo-5,6-dimethoxypyridin-3-yl)methanol. LCMS (C$_8$H$_{11}$BrNO$_3$) (ES, m/z): 248, 250 [M+H]$^+$.

Step 5: 2-Bromo-5,6-dimethoxynicotinaldehyde

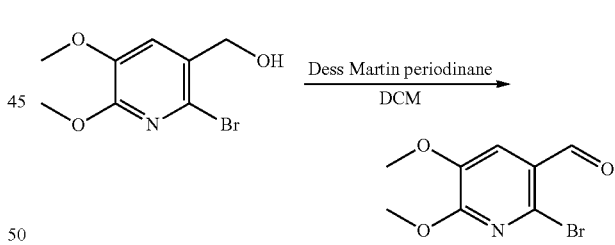

Dess-Martin periodinane (539 mg, 1.27 mmol) was added to a mixture of (2-bromo-5,6-dimethoxypyridin-3-yl)methanol (210 mg, 0.847 mmol) in DCM (10.0 mL). The reaction mixture was stirred at RT for 2 hours. H$_2$O (20.0 mL), aq Na$_2$SO$_4$ (15.0 mL), aq NaHCO$_3$ (25.0 mL), and EtOAc (15.0 mL) were added to the reaction mixture. The reaction mixture was extracted with EtOAc (3×15 mL). The organic layers were combined, dried over MgSO$_4$, filtered, and concentrated under reduced pressure. The residue was purified by prep-TLC (eluting EtOAc in PE) to afford 2-bromo-5,6-dimethoxynicotinaldehyde. LCMS (C$_8$H$_9$BrNO$_3$) (ES, m/z): 246, 248 [M+H]$^+$. $^1$H NMR (400 MHz, CDCl$_3$-d) δ 10.17 (s, 1H), 7.51 (s, 1H), 4.13 (s, 3H), 3.93 (s, 3H).

Step 6: 5,6-Dimethoxythieno[2,3-b]pyridine-2-carboxylic Acid

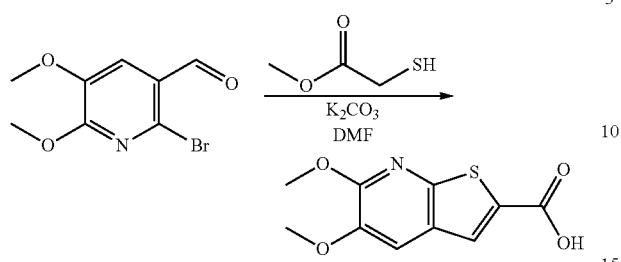

A mixture of 2-bromo-5,6-dimethoxynicotinaldehyde (215 mg, 0.874 mmol), $K_2CO_3$ (362 mg, 2.62 mmol) and methyl 2-mercaptoacetate (0.10 mL, 1.1 mmol) in DMF (5.0 mL) was degassed and backfilled with $N_2$ three times. The reaction mixture was stirred at 60° C. for 12 hours. The reaction mixture was cooled to RT and then concentrated under reduced pressure. The residue was diluted with $H_2O$ (10 mL) and EtOAc (10 mL), and the mixture was then extracted with additional EtOAc (3×10 mL). The combined organic layers were discarded. The aqueous layer was then acidified to pH~5-6 with HCl (1N). The aqueous layer was then extracted with EtOAc (3×5 mL). The organic layers were combined, washed with brine (10 mL), dried over $MgSO_4$, filtered, and concentrated under reduced pressure. The residue was purified by prep-TLC (eluting EtOAc in PE) to afford 5,6-dimethoxythieno[2,3-b]pyridine-2-carboxylic acid that was used without purification. LCMS ($C_{10}H_{10}NO_4S$) (ES, m/z): 240 [M+H]$^+$. $^1$H NMR (400 MHz, DMSO-$d_6$) δ 7.93 (s, 1H), 7.81 (s, 1H), 3.98 (s, 3H), 3.85 (s, 3H).

Step 7: Methyl 3-(5,6-dimethoxythieno[2,3-b]pyridin-2-yl)-3-oxopropanoate

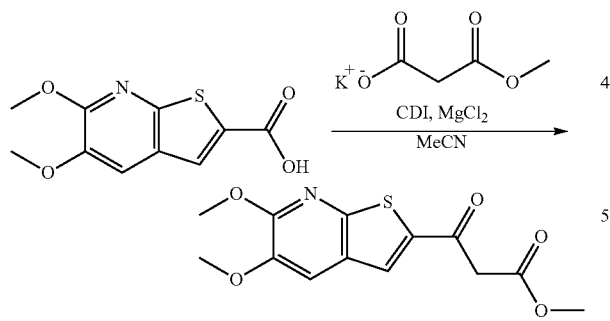

CDI (132 mg, 0.815 mmol) was added to a mixture of 5,6-dimethoxythieno[2,3-b]pyridine-2-carboxylic acid (130 mg, 0.543 mmol) in ACN (5.0 mL). The reaction mixture was stirred at RT under $N_2$ for 1 hour. A mixture of potassium 3-methoxy-3-oxopropanoate (127 mg, 0.815 mmol) and $MgCl_2$ (78 mg, 0.82 mmol) was added to the reaction mixture. The reaction mixture was stirred at RT for 12 hours. The reaction mixture was concentrated under reduced pressure, and the residue was diluted with $H_2O$ (10 mL), acidified to pH~5-6 with HCl (10% in $H_2O$), and extracted with EtOAc (3×10 mL). The organic layers were combined, washed with brine (10 mL), dried over $MgSO_4$, filtered, and concentrated under reduced pressure. The residue was purified by prep-TLC (eluting EtOAc in PE) to afford methyl 3-(5,6-dimethoxythieno[2,3-b]pyridin-2-yl)-3-oxopropanoate. LCMS ($C_{13}H_{14}NO_5S$) (ES, m/z): 296 [M+H]$^+$. $^1$H NMR (400 MHz, CDCl$_3$-d) δ 7.82 (s, 1H), 7.38 (s, 1H), 4.13 (s, 3H), 3.99 (s, 2H), 3.94 (s, 3H), 3.77 (s, 3H).

Step 8: Dimethyl 2-(5,6-dimethoxythieno[2,3-b]pyridine-2-carbonyl)succinate

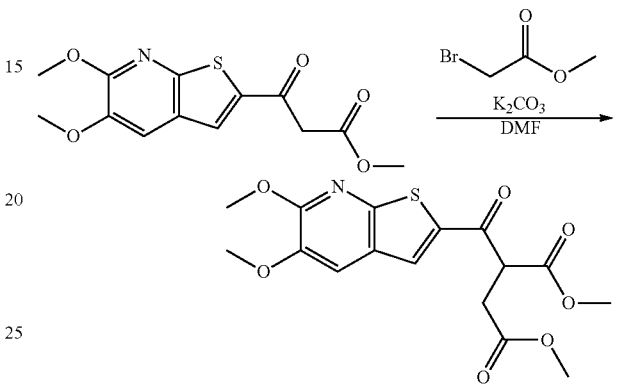

Methyl 2-bromoacetate (0.02 mL, 0.2 mmol) and $K_2CO_3$ (32 mg, 0.24 mmol) were added to a mixture of methyl 3-(5,6-dimethoxythieno[2,3-b]pyridin-2-yl)-3-oxopropanoate (63 mg, 0.21 mmol) in DMF (5.0 mL). The reaction mixture was stirred at RT for 12 hours. $H_2O$ (5 mL) and EtOAc (5 mL) were added to the reaction mixture, and the mixture was extracted with EtOAc (3×5 mL). The organic layers were combined, washed with brine (10 mL), dried over $MgSO_4$, filtered, and concentrated under reduced pressure. The residue was purified by prep-TLC (eluting EtOAc in PE) to afford dimethyl 2-(5,6-dimethoxythieno[2,3-b]pyridine-2-carbonyl)succinate. LCMS ($C_{16}H_{18}NO_7S$) (ES, m/z): 368 [M+H]$^+$.

Step 9: 4-(5,6-Dimethoxythieno[2,3-b]pyridin-2-yl)-4-oxobutanoic Acid

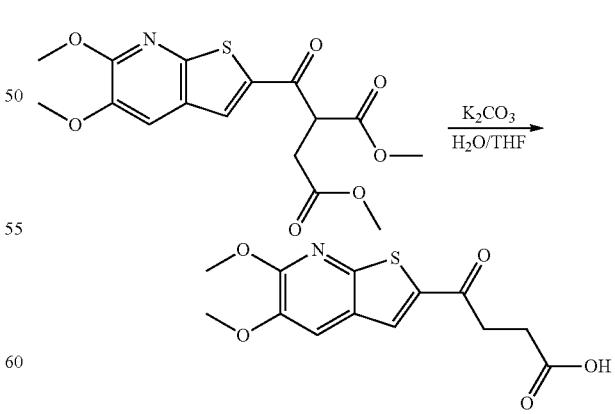

$K_2CO_3$ (75 mg, 0.54 mmol) was added to a mixture of dimethyl dimethoxythieno[2,3-b]pyridine-2-carbonyl)succinate (40 mg, 0.11 mmol) in THF (1.0 mL) and $H_2O$ (1.0 mL). The reaction mixture was stirred at RT for 1 hour, and then the mixture was heated to 80° C. and stirred for an additional 12 hours. The reaction mixture was acidified with HCl (1M in H₂O) to pH~6. The reaction mixture was purified directly by prep-HPLC (eluting ACN in H₂O, with 0.1% TFA) to afford 4-(5,6-dimethoxythieno[2,3-b]pyridin-2-yl)-4-oxobutanoic acid. LCMS (C₁₃H₁₄NO₅S) (ES, m/z): 296 [M+H]⁺. ¹H NMR (400 MHz, MeOD-d₄) δ=8.06 (s, 1H), 7.68 (s, 1H), 4.06 (s, 3H), 3.92 (s, 3H), 3.34 (t, J=6.3 Hz, 2H), 2.73 (t, J=6.5 Hz, 2H).

Example 6: 4-(5,6-Dimethoxythieno[2,3-b]pyridin-2-yl)-4-oxobutanoic Acid

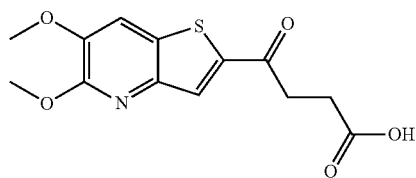 [SMILES: COc1cc2sc(C(=O)CCC(=O)O)cc2nc1OC]

Step 1: Methyl 3-(5,6-dimethoxythieno[3,2-b]pyridin-2-yl)-3-oxopropanoate

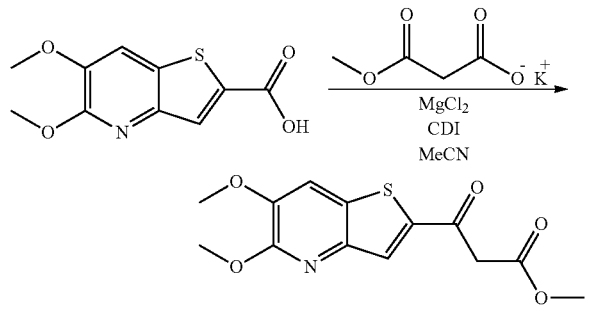

CDI (102 mg, 0.627 mmol) was added to a mixture of 5,6-dimethoxythieno[3,2-b] pyridine-2-carboxylic acid (100 mg, 0.418 mmol) in ACN (5 mL). The reaction mixture was stirred at RT under N₂ for 2 hours. A mixture of potassium 3-methoxy-3-oxopropanoate (98 mg, 0.63 mmol) and MgCl₂ (60 mg, 0.63 mmol) was added to the solution. The mixture was stirred at RT for 12 hours. The reaction mixture was concentrated under reduced pressure and and then diluted with H₂O (10 mL). The mixture was extracted with EtOAc (3×20 mL). The organic layers were combined, washed with brine (20 mL), dried over MgSO₄, filtered, and concentrated under reduced pressure. The residue was purified by prep-TLC (eluting EtOAc in PE) to afford methyl 3-(5,6-dimethoxythieno[3,2-b]pyridin-2-yl)-3-oxopropanoate. LCMS (C₁₃H₁₄NO₅S) (ES, m/z): 296 [M+H]⁺. ¹H NMR (400 MHz, CDCl₃) δ 7.96 (s, 1H), 7.42 (s, 1H), 4.11 (s, 3H), 4.02 (s, 2H), 3.99 (s, 3H), 3.78 (s, 3H).

Step 2: Dimethyl 2-(5,6-dimethoxythieno[3,2-b]pyridine-2-carbonyl)succinate

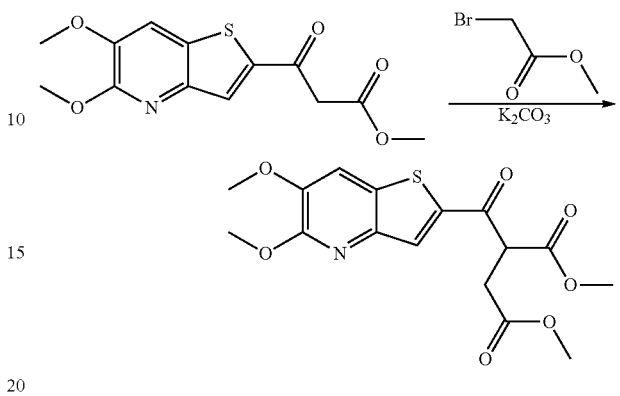

K₂CO₃ (19 mg, 0.14 mmol) and methyl 2-bromoacetate (21 mg, 0.14 mmol) were added to a mixture of methyl 3-(5,6-dimethoxythieno[3,2-b]pyridin-2-yl)-3-oxopropanoate (40 mg, 0.14 mmol) in DMF (1 mL). The reaction mixture was stirred at RT for 12 hours. The reaction mixture was diluted with EtOAc (50 mL), washed with brine (3×5 mL), dried over MgSO₄, filtered, and concentrated under reduced pressure to afford dimethyl 2-(5,6-dimethoxythieno[3,2-b]pyridine-2-carbonyl)succinate that was used without purification. LCMS (C₁₆H₁₈NO₇S) (ES, m/z): 368 [M+H]⁺.

Step 3: 4-(5,6-Dimethoxythieno[2,3-b]pyridin-2-yl)-4-oxobutanoic Acid

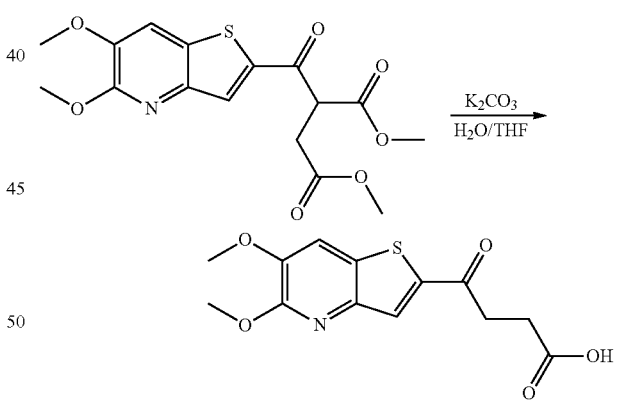

K₂CO₃ (37 mg, 0.27 mmol) was added to a mixture of dimethyl dimethoxythieno[2,3-b]pyridine-2-carbonyl)succinate (25 mg, 0.054 mmol) in THF (1.0 mL) and H₂O (1.0 mL). The reaction mixture was stirred and heated to 80° C. for 12 hours. The reaction mixture was cooled to RT, acidified with HCl (1.0M in H₂O) to pH~6, and then was directly purified by reverse phase HPLC (eluting ACN in H₂O, with 0.1% TFA) to afford 4-(5,6-dimethoxythieno[3,2-b]pyridin-2-yl)-4-oxobutanoic acid. LCMS (C₁₃H₁₄NO₅S) (ES, m/z): 296 [M+H]⁺. ¹H NMR (400 MHz, MeOD-d₄) δ 8.07 (s, 1H), 7.74 (s, 1H), 4.04 (s, 3H), 3.94 (s, 3H), 3.35 (t, J=6.4 Hz, 2H), 2.74 (t, J=6.4 Hz, 2H).

Example 7 and Example 8: (R or S)-4-(5,6-Dimethoxythieno[3,2-b]pyridin-2-yl)-2-methyl-4-oxobutanoic Acid and (R or S)-4-(5,6-dimethoxythieno[3,2-b]pyridin-2-yl)-2-methyl-4-oxobutanoic Acid

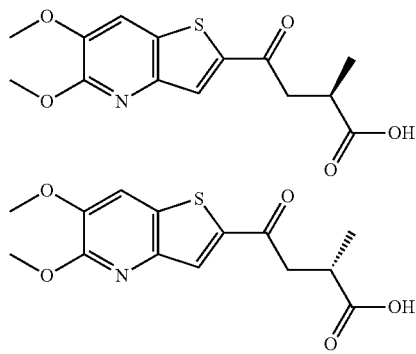

Step 1: di-tert-Butyl 2-(5,6-dimethoxythieno[3,2-b]pyridine-2-carbonyl)-3-methylsuccinate

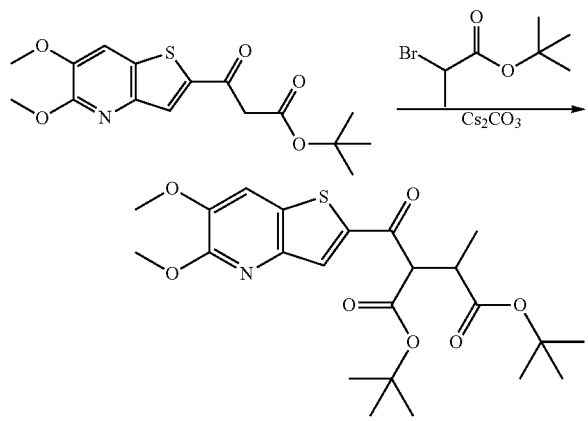

Cs$_2$CO$_3$ (622 mg, 1.91 mmol) was added to a stirred mixture of tert-butyl dimethoxythieno[3,2-b]pyridin-2-yl)-3-oxopropanoate (322 mg, 0.954 mmol) in DMF (3 mL) at 25° C. A mixture of tert-butyl 2-bromopropanoate (210 mg, 1.00 mmol) in DMF (1 mL) was added dropwise to the reaction mixture. The reaction mixture was stirred at RT for 5 hours. Additional tert-butyl 2-bromopropanoate (63 mg, 0.030 mmol) was added, and the reaction mixture was stirred for 1 hour. Additional tert-butyl 2-bromopropanoate (63 mg, 0.030 mmol) was added, and the reaction mixture was stirred overnight. The reaction mixture was diluted with isopropyl acetate (75 mL) and sodium citrate (10% w/v in H$_2$O, 40 mL). The layers were separated, and the aqueous layer was extracted with additional isopropyl acetate (40 mL). The organic layers were combined, washed with brine, dried over anhydrous Na$_2$SO$_4$, filtered, and concentrated under reduced pressure. The residue was purified by silica gel chromatography (eluting EtOAC in Hex) to afford di-tert-butyl 2-(5,6-dimethoxythieno[3,2-b]pyridine-2-carbonyl)-3-methylsuccinate. LCMS (C$_{23}$H$_{32}$NO$_7$S) (ES, m/z): 466 [M+H]$^+$.

Step 2: (R or S)-4-(5,6-Dimethoxythieno[3,2-b]pyridin-2-yl)-2-methyl-4-oxobutanoic Acid and (R or S)-4-(5,6-dimethoxythieno[3,2-b]pyridin-2-yl)-2-methyl-4-oxobutanoic Acid

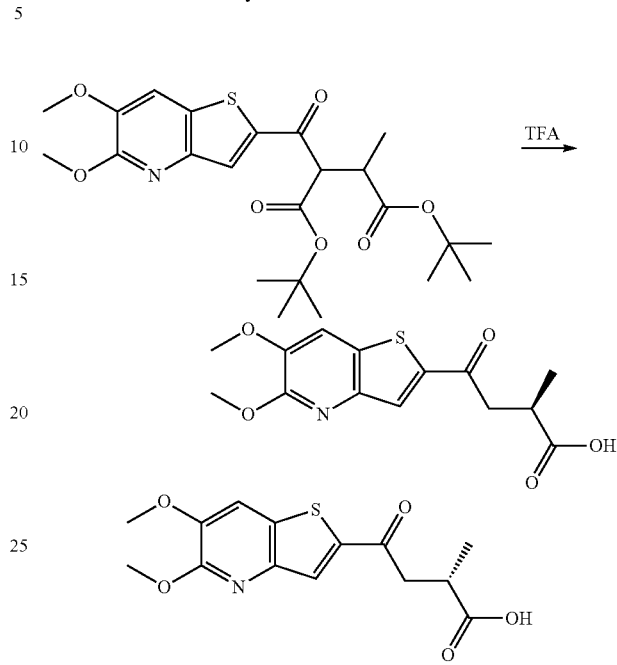

TFA (7 mL) was added to di-tert-butyl 2-(5,6-dimethoxythieno[3,2-b]pyridine-2-carbonyl)-3-methylsuccinate (411 mg, 0.883 mmol), and the mixture was then stirred and heated to 50° C. for 5 hours. The reaction mixture was cooled to RT and concentrated under reduced pressure. The residue was purified by silica gel chromatography (eluting EtOAc in Hex) to afford 4-(5,6-dimethoxythieno[3,2-b]pyridin-2-yl)-2-methyl-4-oxobutanoic acid as a racemate. LCMS (C$_{14}$H$_{16}$NO$_5$S) (ES, m/z): 310 [M+H]$^+$. $^1$H NMR (500 MHz, CDCl$_3$) δ 7.99 (s, 1H), 7.43 (s, 1H), 4.11 (s, 3H), 3.99 (s, 3H), 3.49 (dd, J=17.2 Hz, 7.7 Hz, 1H), 3.22 (dt, J=13.6 Hz, 7.0 Hz, 1H), 3.11 (dd, J=17.2 Hz, 5.5 Hz, 1H), 1.36 (d, J=7.1 Hz, 3H). The racemic mixture was resolved by Chiral-SFC (Column CHIRALPAK AD-H, 21×250 mm, with 40% MeOH (+0.25% DMEA) in CO$_2$) affording two peaks with retention times of 3.57 min. and 5.48 min. Concentration of the two peaks afforded the two enantiomers of 4-(5,6-dimethoxythieno[3,2-b]pyridin-2-yl)-2-methyl-4-oxobutanoic acid.

Peak 1 (R or S)-4-(5,6-Dimethoxythieno[3,2-b]pyridin-2-yl)-2-methyl-4-oxobutanoic acid (Example 7): LCMS (C$_{14}$H$_{16}$NO$_5$S) (ES, m/z): 310 [M+H]$^+$. $^1$H NMR (500 MHz, CDCl$_3$) δ 7.98 (s, 1H), 7.43 (s, 1H), 4.11 (s, 3H), 3.99 (s, 3H), 3.49 (dd, J=17.1 Hz, 7.5 Hz, 1H), 3.44-3.15 (m, 1H), 3.11 (dd, J=17.1 Hz, 5.3 Hz, 1H), 1.36 (d, J=7.0 Hz, 3H).

Peak 2 (R or S)-4-(5,6-Dimethoxythieno[3,2-b]pyridin-2-yl)-2-methyl-4-oxobutanoic acid (Example 8): LCMS (C$_{14}$H$_{16}$NO$_5$S) (ES, m/z): 310 [M+H]$^+$. $^1$H NMR (500 MHz, CDCl$_3$) δ 7.98 (s, 1H), 7.43 (s, 1H), 4.11 (s, 3H), 3.99 (s, 3H), 3.49 (dd, J=17.2 Hz, 7.6 Hz, 1H), 3.20 (dt, J=14.2 Hz, 6.9 Hz, 1H), 3.11 (dd, J=17.2 Hz, 5.6 Hz, 1H), 1.36 (d, J=7.1 Hz, 3H).

Example 9: Cis-2-(5,6-dimethoxythieno[3,2-b]pyridine-2-carbonyl)cyclopropane-1-carboxylic Acid

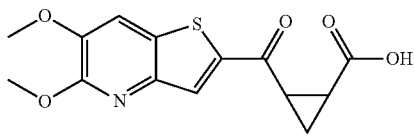 [SMILES: COc1cc2sc(C(=O)C3CC3C(=O)O)cc2nc1OC]

Step 1: 5,6-Dimethoxythieno[3,2-b]pyridine

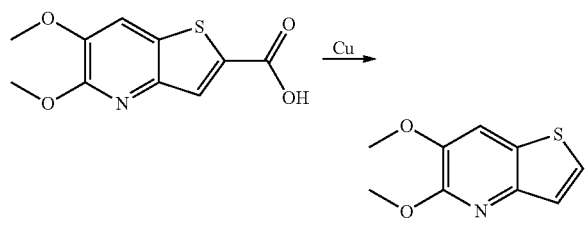

Cu (0.27 g, 4.3 mmol) was added to a mixture of 5,6-dimethoxythieno[3,2-b]pyridine-2-carboxylic acid (0.60 g, 2.5 mmol) in quinoline (5.9 mL, 50 mmol), and the reaction mixture was heated to 190° C. for 2 hours. Upon cooling to RT, the reaction mixture was diluted with EtOAc and aq HCl (2N). The mixture was filtered through CELITE, and the filtrate was washed with $H_2O$, aq sat $NaHCO_3$, and brine. The organics were separated, dried over $MgSO_4$, filtered, and concentrated under reduced pressure. The residue was purified by silica gel chromatography to afford 5,6-dimethoxythieno[3,2-b]pyridine. LCMS ($C_9H_{10}NO_2S$) (ES, m/z): 196 [M+H]$^+$. $^1$H NMR (500 MHz, DMSO-d$_6$) δ 7.93 (s, 1H), 7.76 (d, J=5.4 Hz, 1H), 7.32 (d, J=5.4 Hz, 1H), 3.92 (s, 3H), 3.84 (s, 3H).

Step 2: Cis-2-(5,6-dimethoxythieno[3,2-b]pyridine-2-carbonyl)cyclopropane-1-carboxylic Acid

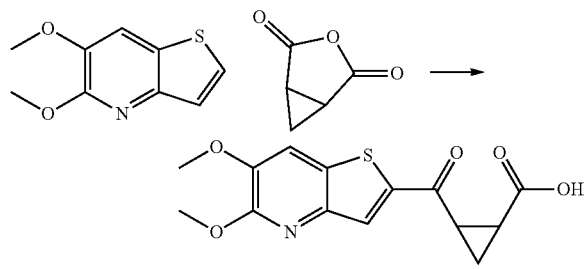

5,6-dimethoxythieno[3,2-b]pyridine (0.15 g, 0.77 mmol) was added to a sealed tube, and the tube was evacuated and then back-filled with $N_2$. THF (3.8 mL) was added, and the mixture was cooled to −78° C. n-BuLi (1.6M in Hex, 0.53 mL, 0.85 mmol) was added, and the mixture was stirred at −78° C. for 30 min. The reaction mixture was then added to a mixture of 3-oxabicyclo[3.1.0]hexane-2,4-dione (0.43 g, 3.8 mmol) in THF (3.0 mL) that had been pre-cooled to −78° C. The reaction mixture was stirred at −78° C. for 30 min. The reaction mixture was allowed to warm to RT and stirred for an additional 30 min. The reaction mixture was diluted with $H_2O$ and EtOAc. The aqueous layer was separated and then acidified to a pH~4 with aqueous HCl (1.0N). The aqueous layer was then extracted with EtOAc (2×). The organic layers were combined, dried over $MgSO_4$, filtered, and concentrated under reduced pressure. The residue was purified by silica gel chromatography (eluting EtOAc in Hex) to afford the desired product as a mixture of isomers. The cis racemate was then resolved by CHIRAL-SFC (Column AD-H (21×250 mm) eluting 30% MeOH with 0.25% DMEA in $CO_2$) to afford cis-2-(5,6-dimethoxythieno[3,2-b]pyridine-2-carbonyl)cyclopropane-1-carboxylic acid (retention time 7.23 min). LCMS ($C_{14}H_{14}NO_5S$) (ES, m/z): 308 [M+H]$^+$. $^1$H NMR (600 MHz, DMSO-d6) δ 8.22 (s, 1H), 7.93 (s, 1H), 3.92 (s, 3H), 3.84 (s, 3H), 3.09-2.96 (m, 1H), 2.28-2.19 (m, 1H), 1.55-1.45 (m, 1H), 1.28-1.21 (m, 1H).

Example 10: (S)-4-(5-Chloro-6-methoxythieno[3,2-b]pyridin-2-yl)-2-methyl-4-oxobutanoic Acid

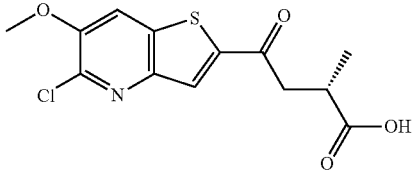 [SMILES: COc1cc2sc(C(=O)C[C@H](C)C(=O)O)cc2nc1Cl]

Step 1: 5-Chloro-6-methoxythieno[3,2-b]pyridine-2-carbonyl Chloride

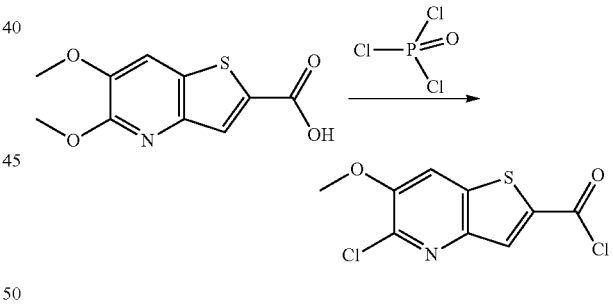

Phosphorous oxychloride (1.17 mL, 12.5 mmol) was added dropwise to a stirred mixture of 5,6-dimethoxythieno[3,2-b]pyridine-2-carboxylic acid (1.00 g, 4.1 mmol) in DMF (10.45 ml) at 0° C. under $N_2$. After 10 min, the reaction mixture was allowed to warm to RT. The reaction mixture was then heated to 100° C. and stirred for 45 min. The reaction mixture was added to ice water (100 mL) and stirred. The mixture was filtered, and the collected materials were washed with $H_2O$ (2×30 mL) and Hex (50 mL). The washed materials were diluted with $Et_2O$ (50 mL) and again filtered. The filtered materials were dissolved in $CH_2Cl_2$ (60 mL), and the mixture was dried over anhydrous $Na_2SO_4$, filtered, and concentrated under reduced pressure to afford 5-chloro-6-methoxythieno[3,2-b]pyridine-2-carbonyl chloride. $^1$H NMR (500 MHz, CDCl$_3$) δ 8.32 (s, 1H), 7.60 (s, 1H), 4.06 (s, 3H).

Step 2: Methyl (S)-4-(5-chloro-6-methoxythieno[3,2-b]pyridin-2-yl)-2-methyl-4-oxobutanoate

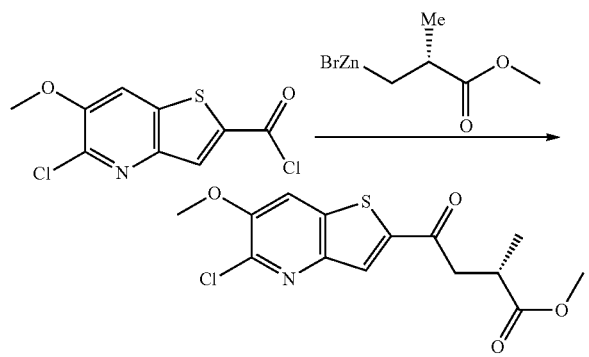

CuI (0.073 g, 0.38 mmol) was placed under a vacuum and heated for 1 min. The flask was allowed to cool to RT and was then opened to $N_2$. Twice more the flask was evacuated, then backfilled with $N_2$. The flask remained under $N_2$. THF (2 mL) was added, and the reaction mixture was cooled in an ice water bath. A solution of (R)-(3-methoxy-2-methyl-3-oxopropyl)zinc(II) bromide in THF (0.50M, 1.68 mL, 0.84 mmol) was added dropwise to the reaction mixture over a period of 5 min. The reaction mixture was stirred for 105 min. at 0° C. A mixture of 5-chloro-6-methoxythieno[3,2-b]pyridine-2-carbonyl chloride (0.200 g, 0.763 mmol) in NMP (3 mL) was then added dropwise over 5 min. The reaction mixture was then stirred for 3 hours at 0° C. The reaction mixture was then added to a stirred mixture of isopropyl acetate (50 mL) and sodium citrate (20% w/v in $H_2O$, 50 mL). After stirring for 20 min, the layers were separated, and the aqueous layer was extracted with additional isopropyl acetate (30 mL). The organic layers were combined, washed with brine (2×50 mL), dried over anhydrous $Na_2SO_4$, filtered, and concentrated under reduced pressure. The residue was purified by silica gel chromatography (eluting EtOAc in Hex) to afford (S)-methyl 4-(5-chloro-6-methoxythieno [3,2-b]pyridin-2-yl)-2-methyl-4-oxobutanoate. LCMS ($C_{14}H_{15}ClNO_4S$) (ES, m/z): 328 [M+H]+. $^1$H NMR (500 MHz, $CDCl_3$) δ 7.99 (s, 1H), 7.60 (s, 1H), 4.03 (s, 3H), 3.72 (s, 3H), 3.51 (dd, J=17.2 Hz, 7.9 Hz, 1H), 3.21-3.12 (m, 1H), 3.06 (dd, J=17.2 Hz, 5.2 Hz, 1H), 1.32 (d, J=7.1 Hz, 3H).

Step 3: (S)-4-(5-Chloro-6-methoxythieno[3,2-b]pyridin-2-yl)-2-methyl-4-oxobutanoic Acid

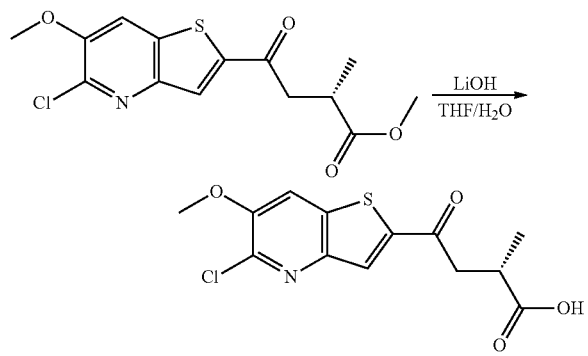

LiOH·$H_2O$ (0.055 g, 1.31 mmol) was added to a mixture of (S)-methyl 4-(5-chloro-6-methoxythieno[3,2-b]pyridin-2-yl)-2-methyl-4-oxobutanoate (0.107 g, 0.326 mmol) in $H_2O$ (0.5 mL) and THF (0.5 mL). The reaction mixture was heated to 45° C. and stirred for 1 hour. Additional THF (0.5 mL) and $H_2O$ (0.5 mL) were added to the reaction mixture. After stirring for an additional 4 hours, the reaction mixture was cooled to RT and partitioned between EtOAc (5 mL) and $H_2O$ (5 mL). AcOH was added until pH~4. The layers were separated, and the aqueous layer was extracted with additional EtOAc (5 mL). The organic layers were combined, washed with brine (5 mL), dried over anhydrous $Na_2SO_4$, filtered, and concentrated under reduced pressure. The residue was purified by silica gel chromatography (eluting [25% EtOH in EtOAc] in Hex) to afford (S)-4-(5-chloro-6-methoxythieno[3,2-b]pyridin-2-yl)-2-methyl-4-oxobutanoic acid. LCMS ($C_{13}H_{13}ClNO_4S$) (ES, m/z): 314 [M+H]+. $^1$H NMR (500 MHz, $CDCl_3$) δ 8.02 (s, 1H), 7.62 (s, 1H), 4.04 (s, 3H), 3.52 (dd, J=17.4 Hz, 7.9 Hz, 1H), 3.27-3.17 (m, 1H), 3.11 (dd, J=17.4 Hz, 5.3 Hz, 1H), 1.38 (d, J=7.2 Hz, 3H).

Example 11 and Example 12: (R or S)-4-(5,6-Dimethoxythieno[3,2-b]pyridin-2-yl)-2-ethyl-4-oxobutanoic Acid and (R or S)-4-(5,6-dimethoxythieno[3,2-b]pyridin-2-yl)-2-ethyl-4-oxobutanoic Acid

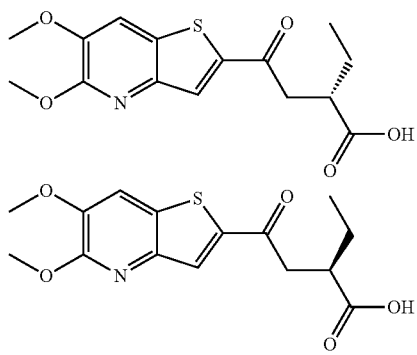

Step 1: 1-(tert-Butyl) 4-methyl 2-(5,6-dimethoxythieno[3,2-b]pyridine-2-carbonyl)-3-ethylsuccinate

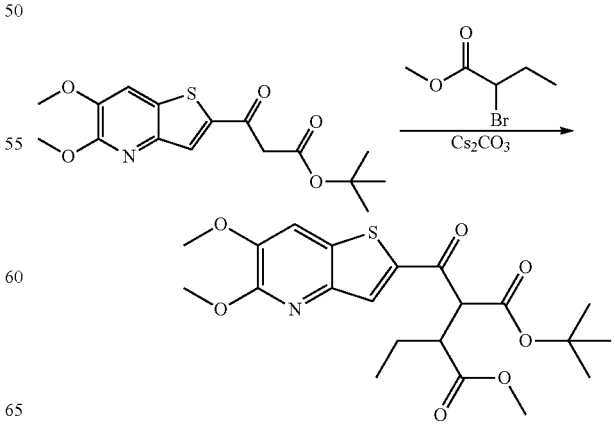

A mixture of tert-butyl 3-(5,6-dimethoxythieno[3,2-b]pyridin-2-yl)-3-oxopropanoate (50 mg, 0.15 mmol) and Cs$_2$CO$_3$ (97 mg, 0.30 mmol) in NMP (0.5 mL) was stirred at RT for 15 min. Methyl 2-bromobutanoate (0.026 mL, 0.22 mmol) was added to the reaction mixture, which was then stirred at RT for 40 hours. The reaction mixture was diluted with EtOAc (30 mL) and washed with H$_2$O (30 mL). The organic layer was separated, dried over Na$_2$SO$_4$, filtered, and concentrated under reduced pressure. The residue was purified by silica gel chromatography (eluting EtOAc in Hex) to afford 1-tert-butyl 4-methyl 2-(5,6-dimethoxythieno[3,2-b]pyridine-2-carbonyl)-3-ethylsuccinate as a mixture of diastereomers. LCMS (C$_{21}$H$_{28}$NO$_7$S) (ES, m/z): 438 [M+H]$^+$.

Step 2: Methyl 4-(5,6-dimethoxythieno[3,2-b]pyridin-2-yl)-2-ethyl-4-oxobutanoate

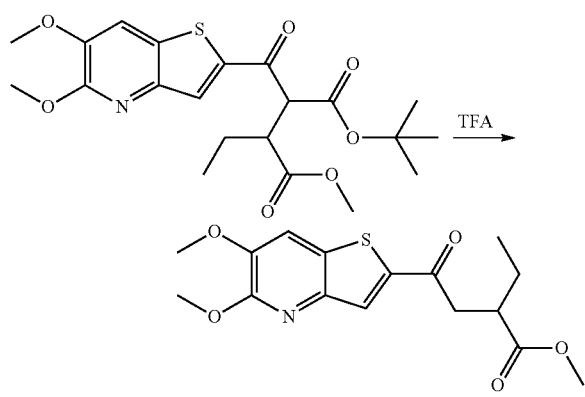

A mixture of TFA (1 mL) and 1-tert-butyl 4-methyl 2-(5,6-dimethoxythieno[3,2-b]pyridine-2-carbonyl)-3-ethylsuccinate (110 mg, 0.251 mmol) was stirred and heated to 70° C. for 1 hour. The reaction mixture was cooled to RT and diluted with DCM (10 mL). The reaction mixture was basified with KOH (10N) to pH~6. The reaction mixture was extracted with DCM (2×20 mL). The organic layers were combined, dried over Na$_2$SO$_4$, filtered, and concentrated under reduced pressure. The residue was purified by silica gel chromatography (eluting EtOAc in Hex) to afford methyl 4-(5,6-dimethoxythieno[3,2-b]pyridin-2-yl)-2-ethyl-4-oxobutanoate. LCMS (C$_{16}$H$_{20}$NO$_5$S) (ES, m/z): 338 [M+H]$^+$. $^1$H NMR (499 MHz, CDCl$_3$) δ 7.99 (s, 1H), 7.43 (s, 1H), 4.11 (s, 3H), 3.99 (s, 3H), 3.72 (s, 3H), 3.47 (dd, J=16.7 Hz, 8.6 Hz, 1H), 3.13-3.01 (m, 2H), 1.74-1.66 (m, 2H), 0.99 (t, J=7.4 Hz, 3H).

Step 3: (R or S)-4-(5,6-Dimethoxythieno[3,2-b]pyridin-2-yl)-2-ethyl-4-oxobutanoic Acid and (R or S)-4-(5,6-dimethoxythieno[3,2-b]pyridin-2-yl)-2-ethyl-4-oxobutanoic Acid

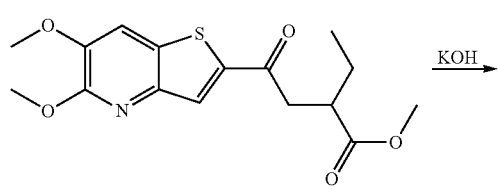

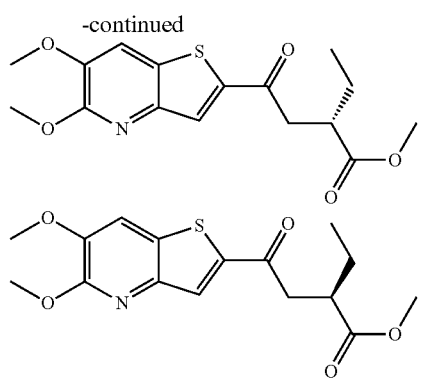

KOH (0.5M in H$_2$O, 1.2 mL, 0.6 mmol) was added dropwise to a mixture of methyl 4-(5,6-dimethoxythieno[3,2-b]pyridin-2-yl)-2-ethyl-4-oxobutanoate (66.4 mg, 0.197 mmol) in 2-propanol (1 mL). The reaction mixture was stirred for 30 min at RT. The reaction mixture was then heated to 70° C. for 15 min. The reaction mixture was cooled to RT and acidified to pH~2 with HCl (1N). The reaction mixture was extracted with DCM (2×20 mL). The organic layers were combined, dried over Na$_2$SO$_4$, filtered, and concentrated under reduced pressure. The residue was purified by silica gel chromatography (eluting EtOAc in Hex) to afford the racemic product. The racemate was resolved by CHIRAL-SFC (Column AD-H (250 mm*21 mm) eluting 40% MeOH (+0.25% DMEA) in CO$_2$) to afford two peaks with retention times of 3.7 min and 5.9 min. Concentration of the two peaks afforded the two enantiomers of 4-(5,6-dimethoxythieno[3,2-b]pyridin-2-yl)-2-ethyl-4-oxobutanoic acid.

Peak 1 (R or S)-4-(5,6-Dimethoxythieno[3,2-b]pyridin-2-yl)-2-ethyl-4-oxobutanoic acid (Example 11): LCMS (C$_{15}$H$_{18}$NO$_5$S) (ES, m/z) 324 [M+H]$^+$. $^1$H NMR (499 MHz, DMSO-d$_6$) δ 11.94 (br s, 1H), 8.30 (s, 1H), 7.98 (s, 1H), 3.96 (s, 3H), 3.89 (s, 3H), 3.44 (dd, J=17.4 Hz, 9.6 Hz, 1H), 3.10 (dd, J=17.4 Hz, 3.6 Hz, 1H), 2.82-2.73 (m, 1H), 1.68-1.55 (m, 2H), 0.93 (t, J=7.3 Hz, 3H).

Peak 2 (R or S)-4-(5,6-Dimethoxythieno[3,2-b]pyridin-2-yl)-2-ethyl-4-oxobutanoic acid (Example 12): LCMS (C$_{15}$H$_{18}$NO$_5$S) (ES, m/z) 324 [M+H]$^+$. $^1$H NMR (499 MHz, DMSO-d$_6$) δ 11.94 (br s, 1H), 8.30 (s, 1H), 7.98 (s, 1H), 3.96 (s, 3H), 3.89 (s, 3H), 3.44 (dd, J=17.4 Hz, 9.6 Hz, 1H), 3.10 (dd, J=17.4 Hz, 3.6 Hz, 1H), 2.81-2.73 (m, 1H), 1.68-1.55 (m, 2H), 0.93 (t, J=7.3 Hz, 3H).

Example 13 and Example 14: (R or S)-2-(2-(5,6-Dimethoxythieno[3,2-b]pyridin-2-yl)-2-oxoethyl) pentanoic Acid and (R or S)-2-(2-(5,6-dimethoxythieno[3,2-b]pyridin-2-yl)-2-oxoethyl) pentanoic Acid

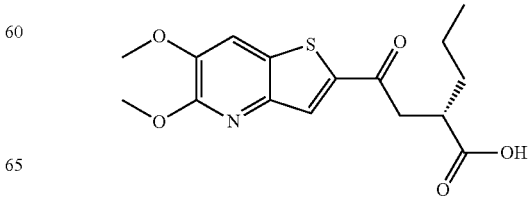

-continued

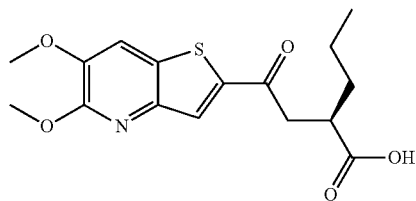

Step 1: 1-(tert-Butyl) 4-methyl 2-(5,6-dimethoxythieno[3,2-b]pyridine-2-carbonyl)-3-propylsuccinate

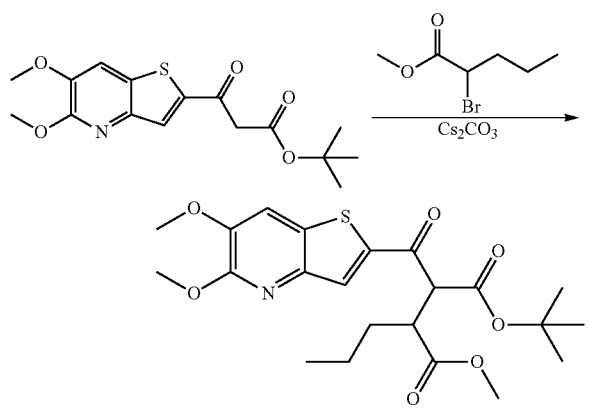

Methyl 2-bromopentanoate (0.042 mL, 0.28 mmol) was added to a mixture of tert-butyl 3-(5,6-dimethoxythieno[3,2-b]pyridin-2-yl)-3-oxopropanoate (63 mg, 0.19 mmol) and $Cs_2Co_3$ (122 mg, 0.375 mmol) in NMP (0.5 mL). The reaction mixture was stirred at RT for 3 hours. The reaction mixture was diluted with EtOAc (30 mL) and washed with $H_2O$ (2×30 mL). The organic layer was separated, dried over $Na_2SO_4$, filtered, and concentrated under reduced pressure. The residue was purified by silica gel chromatography (eluting EtOAc in Hex) to afford 1-tert-butyl 4-methyl 2-(5,6-dimethoxythieno[3,2-b]pyridine-2-carbonyl)-3-propylsuccinate as a mixture of diastereomers. LCMS ($C_{22}H_{30}NO_7S$) (ES, m/z): 452 $[M+H]^+$.

Step 2: Methyl 2-(2-(5,6-dimethoxythieno[3,2-b]pyridin-2-yl)-2-oxoethyl)pentanoate

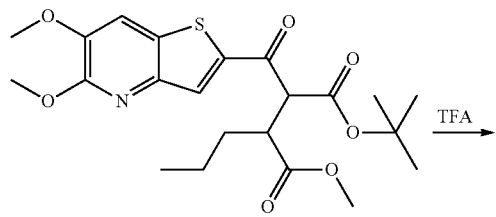

-continued

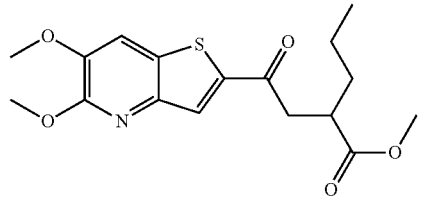

A mixture of 1-tert-butyl 4-methyl 2-(5,6-dimethoxythieno[3,2-b]pyridine-2-carbonyl)-3-ethylsuccinate (65 mg, 0.14 mmol) and TFA (1 mL) was stirred and heated to 70° C. for 1 hour. The reaction mixture was cooled to RT and then concentrated under reduced pressure to afford methyl 4-(5,6-dimethoxythieno[3,2-b]pyridin-2-yl)-2-ethyl-4-oxopentanoate, which was used without purification. LCMS ($C_{17}H_{22}NO_5S$) (ES, m/z): 352 $[M+H]^+$.

Step 3: (R or S)-2-(2-(5,6-Dimethoxythieno[3,2-b]pyridin-2-yl)-2-oxoethyl)pentanoic Acid and (R or S)-2-(2-(5,6-dimethoxythieno[3,2-b]pyridin-2-yl)-2-oxoethyl)pentanoic Acid

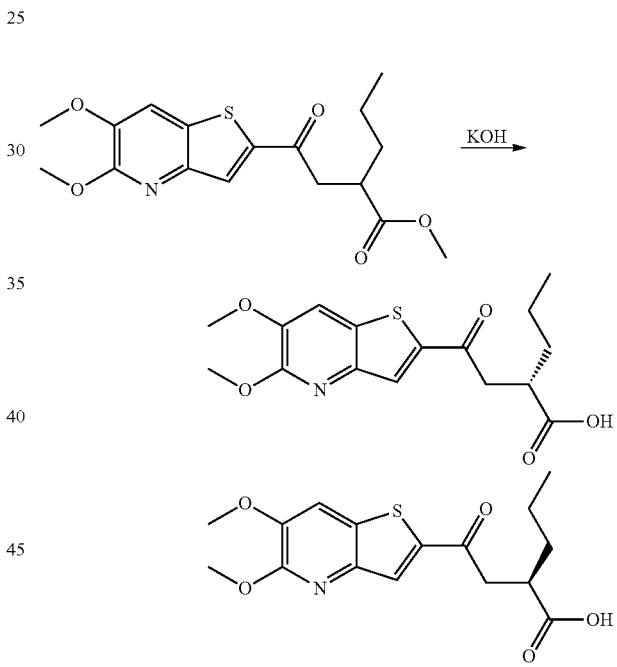

KOH (0.50N, 1.7 mL, 0.85 mmol) was added to a mixture of methyl 4-(5,6-dimethoxythieno[3,2-b]pyridin-2-yl)-2-ethyl-4-oxopentanoate (50.0 mg, 0.142 mmol) and 2-propanol (1 mL). The reaction mixture was stirred and heated to 70° C. for 40 min. The reaction mixture was cooled to RT, acidified to pH~3 with HCl (1N), and then was extracted with DCM (2×30 mL). The organic layers were combined, dried over $Na_2SO_4$, filtered, and concentrated under reduced pressure. The residue was purified by silica gel chromatography (eluting EtOAc in Hex) to afford the racemic product. The racemic mixture was resolved by CHIRAL-SFC (Column AD-H (250 mm*21 mm), with 25% MeOH (+0.25% DMEA) in $CO_2$) affording two peaks with retention times of 4.7 min and 6.0 min. Concentration of the two peaks afforded the two enantiomers of 4-(5,6-dimethoxythieno[3,2-b]pyridin-2-yl)-2-ethyl-4-oxopentanoic acid.

Peak 1 (R or S)-2-(2-(5,6-Dimethoxythieno[3,2-b]pyridin-2-yl)-2-oxoethyl) pentanoic acid (Example 13): LCMS (C₁₆H₂₀NO₅S) (ES, m/z) 338 [M+H]⁺. ¹H NMR (499 MHz, DMSO-d₆) δ 12.18 (s, 1H), 8.29 (s, 1H), 7.98 (s, 1H), 3.96 (s, 3H), 3.89 (s, 3H), 3.42 (dd, J=17.6 Hz, 9.6 Hz, 1H), 3.13 (dd, J=17.5 Hz, 4.1 Hz, 1H), 2.86-2.77 (m, 1H), 1.65-1.48 (m, 2H), 1.43-1.28 (m, 2H), 0.89 (t, J=7.3 Hz, 3H).

Peak 2 (R or S)-2-(2-(5,6-Dimethoxythieno[3,2-b]pyridin-2-yl)-2-oxoethyl) pentanoic acid (Example 14): LCMS (C₁₆H₂₀NO₅S) (ES, m/z) 338 [M+H]⁺. ¹H NMR (499 MHz, DMSO-d₆) δ 12.18 (s, 1H), 8.29 (s, 1H), 7.98 (s, 1H), 3.96 (s, 3H), 3.89 (s, 3H), 3.42 (dd, J=17.6 Hz, 9.6 Hz, 1H), 3.13 (dd, J=17.5 Hz, 4.1 Hz, 1H), 2.86-2.77 (m, 1H), 1.65-1.47 (m, 2H), 1.43-1.28 (m, 2H), 0.89 (t, J=7.3 Hz, 3H).

Example 15: 4-(6-Bromo-5-methoxythieno[3,2-b]pyridin-2-yl)-4-oxobutanoic Acid

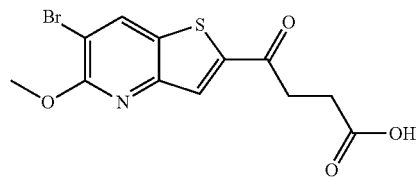 [SMILES: COc1nc2cc(C(=O)CCC(=O)O)sc2cc1Br]

Step 1: 6-Bromothieno[3,2-b]pyridine

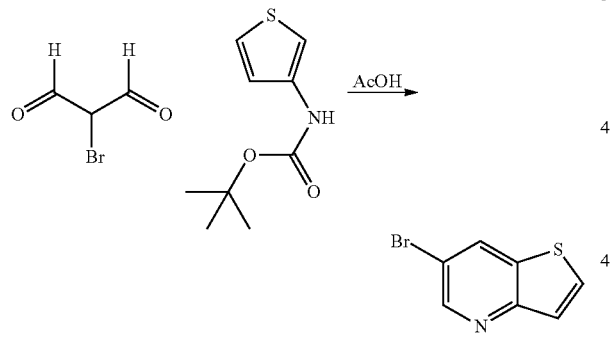

AcOH (50 mL) was added to a mixture of 2-bromomalonaldehyde (3.56 g, 23.6 mmol) and tert-butyl thiophen-3-ylcarbamate (4.70 g, 23.6 mmol) at RT under air atmosphere (septum was vented via needle). The reaction mixture was stirred and heated to 100° C. for 24 hours. The reaction mixture was then cooled to RT and diluted with EtOAc (300 mL). Sat aq NaHCO₃ was added until gas evolution ceased. The organic layer was separated, washed with brine (50 mL), dried over MgSO₄, filtered, and concentrated under reduced pressure. The residue was purified by silica gel chromatography (eluting EtOAc in Hex) to afford 6-bromothieno[3,2-b]pyridine. LCMS (C₇H₅BrNS) (ES, m/z): 214, 216 [M+H]⁺. ¹H NMR (499 MHz, DMSO-d₆) δ 8.86 (s, 1H), 8.74 (s, 1H), 8.18 (d, J=5.4 Hz, 1H), 7.58 (d, J=5.4 Hz, 1H).

Step 2: 6-Bromothieno[3,2-b]pyridine 4-oxide

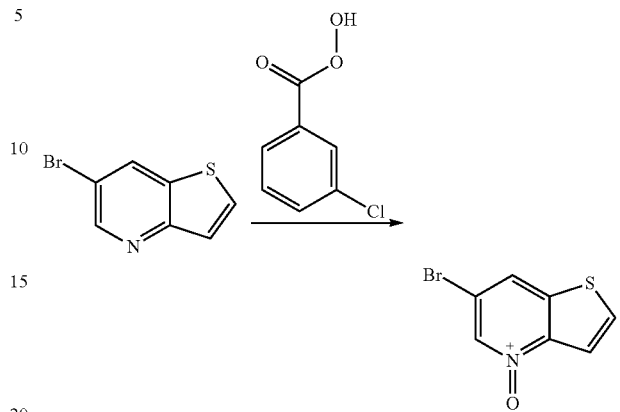

mCPBA (1.49 g, 6.63 mmol) was added to a mixture of 6-bromothieno[3,2-b] pyridine (1.42 g, 6.63 mmol) in DCM (50 mL) at 0° C. under Ar. The reaction mixture was then allowed to warm to RT and stirred for an additional 24 hours. The reaction mixture was then concentrated under reduced pressure. The residue was purified by silica gel chromatography (eluting [5% MeOH in EtOAc] in DCM) to afford 6-bromothieno[3,2-b]pyridine 4-oxide. LCMS (C₇H₅BrNOS) (ES, m/z): 230, 232 [M+H]⁺.

Step 3: 6-Bromothieno[3,2-]pyridin-5-yl Acetate

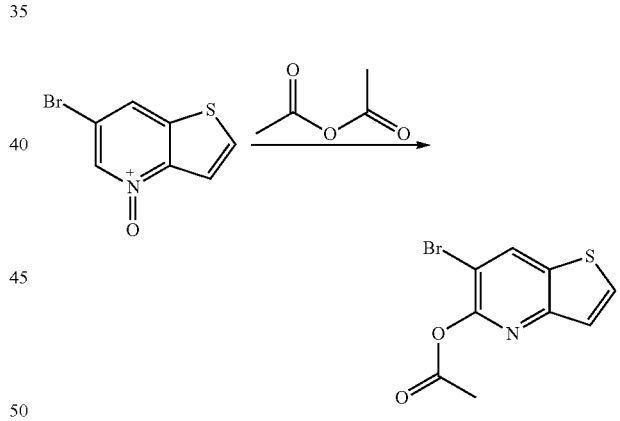

Acetic anhydride (20 mL, 210 mmol) was added to 6-bromothieno[3,2-b]pyridine 4-oxide (1.38 g, 6.00 mmol) at RT under N₂. The reaction mixture was then heated to 140° C. and stirred for 4 hours. The reaction mixture was then cooled to RT and diluted with EtOAc (200 mL) and H₂O (200 mL). NaHCO₃ was slowly added portionwise to the reaction mixture until all gas evolution ceased. The organic layer was separated, washed with brine (25 mL), dried over MgSO₄, filtered, and concentrated under reduced pressure. The residue was purified by silica gel chromatography (eluting [5% MeOH in EtOAc] in DCM) to afford 6-bromothieno[3,2-b]pyridin-5-yl acetate. LCMS (C₉H₇BrNO₂S—C₂H₂O) (ES, m/z): 230, 232 [M+H-acetate]⁺. ¹H NMR (499 MHz, DMSO-d₆) δ 9.04 (s, 1H), 8.29 (d, J=5.2 Hz, 1H), 7.54 (d, J=5.4 Hz, 1H), 2.41 (s, 3H).

Step 4: 6-Bromothieno[3,2-b]pyridin-5-ol

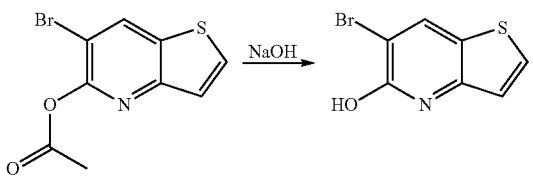

NaOH (2.0M in H$_2$O, 4.0 mL, 8.0 mmol) was added to a solution of 6-bromothieno [3,2-b]pyridin-5-yl acetate (431 mg, 1.58 mmol) in MeOH (5.0 mL) at 20° C. under N$_2$. The reaction mixture was then stirred for 1 hour at 20° C. The reaction mixture was quenched with HCl (1.0M in H$_2$O, 8.0 mL, 8.0 mmol) and then diluted by the addition of H$_2$O (10 mL). The reaction mixture was stirred for 30 minutes and then filtered. The collected material was washed with additional H$_2$O (10 mL) and then dried under reduced pressure to afford 6-bromothieno[3,2-b]pyridin-5-ol. LCMS (C$_7$H$_5$BrNOS) (ES, m/z): 230, 232 [M+H]$^+$. $^1$H NMR (499 MHz, DMSO-d$_6$) δ 12.65 (s, 1H), 8.59 (s, 1H), 7.91 (d, J=5.3 Hz, 1H), 6.99 (d, J=5.1 Hz, 1H).

Step 5: 6-Bromo-5-chlorothieno[3,2-b]pyridine

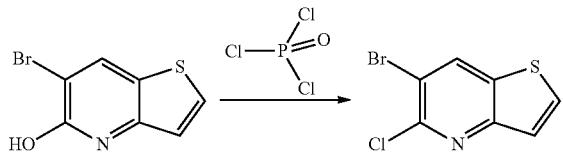 [SMILES: Oc1nc2ccsc2cc1Br ; O=P(Cl)(Cl)Cl ; Clc1nc2ccsc2cc1Br]

Phosphorus oxychloride (15.2 mL, 163 mmol) was added to 6-bromothieno[3,2-b]pyridin-5-ol (375 mg, 1.63 mmol) at 20° C. under N$_2$. The reaction mixture was then stirred and heated to 100° C. for 2 days. The reaction mixture was cooled to RT and quenched by the dropwise addition of the reaction mixture to a solution of aqueous saturated NaHCO$_3$ solution. The reaction mixture was further diluted with EtOAc (250 mL) and stirred. The organic layer was separated, washed with brine (25 mL), dried over MgSO$_4$, filtered, and concentrated under reduced pressure to afford 6-bromo-5-chlorothieno[3,2-b]pyridine which was used without purification. LCMS (C$_7$H$_4$BrClNS) (ES, m/z): 248, 250 [M+H]$^+$.

Step 6: 6-Bromo-5-methoxythieno[3,2-b]pyridine

NAOMe (25% in MeOH, 3.24 mL, 14 mmol) was added to a mixture of 6-bromo-5-chlorothieno[3,2-b]pyridine (352 mg, 1.42 mmol) in MeOH (10 mL) at 20° C. under N$_2$. The reaction mixture was stirred and heated to 100° C. for 1 hour in a microwave reactor. The reaction mixture was quenched with citric acid (1.0M in H$_2$O, 28 mL, 28 mmol) and diluted with EtOAc (250 mL). The organic layer was separated, washed with brine (25 mL), dried over MgSO$_4$, filtered, and concentrated under reduced pressure. The residue was purified by silica gel chromatography (eluting [5% MeOH in EtOAc] in DCM) to afford 6-bromo-5-methoxythieno [3,2-b]pyridine. LCMS (C$_8$H$_7$BrNOS) (ES, m/z): 244, 246 [M+H]$^+$. $^1$H NMR (499 MHz, DMSO-d$_6$) δ 8.78 (s, 1H), 8.09 (d, J=5.3 Hz, 1H), 7.44 (d, J=5.2 Hz, 1H), 3.99 (s, 3H).

Step 7: 4-(6-Bromo-5-methoxythieno[3,2-b]pyridin-2-yl)-4-oxobutanoic Acid

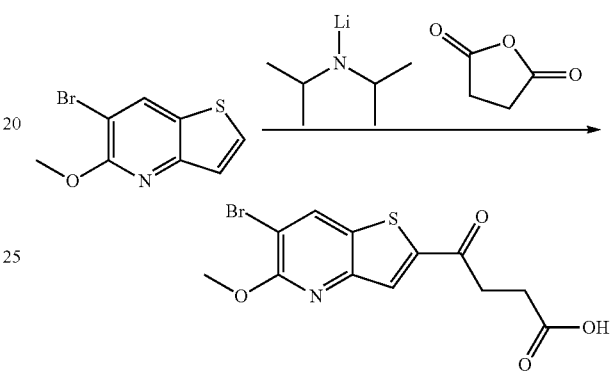

LDA (2.0M in THF, 0.090 mL, 0.18 mmol) was added to a solution of 6-bromo-5-methoxythieno[3,2-b]pyridine (40 mg, 0.16 mmol) in THF (2.0 mL) at −78° C. The reaction mixture was stirred for 15 min while warming to approximately −40° C., and was then quenched at −40° C. by the addition of a solution of dihydrofuran-2,5-dione (98 mg, 0.98 mmol) in THF (2.0 mL). The reaction mixture was then allowed to warm to 20° C. and was stirred for an additional 15 min at 20° C. The reaction mixture was quenched with HCl (1.0N, 0.20 mL, 0.20 mmol) and diluted with EtOAc (100 mL). The organic layer was separated, washed with brine (10 mL), dried over MgSO$_4$, filtered, and concentrated under reduced pressure. The residue was purified by reverse phase HPLC (eluting ACN/water gradient with 0.1% TFA modifier, C-18 stationary phase) to afford 4-(6-bromo-5-methoxythieno[3,2-b]pyridin-2-yl)-4-oxobutanoic acid. LCMS (C$_{12}$H$_{11}$BrNO$_4$S) (ES, m/z): 344, 346 [M+H]$^+$. $^1$H NMR (499 MHz, DMSO-d$_6$) δ 12.22 (br s, 1H), 8.88 (s, 1H), 8.36 (s, 1H), 4.02 (s, 3H), 3.37-3.34 (m, 2H), 2.64-2.60 (m, 2H).

Example 16: 4-(2,3-Dimethoxythieno[2,3-b]pyrazin-6-yl)-4-oxobutanoic Acid

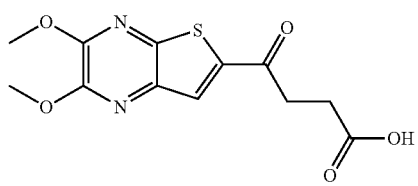 [SMILES: COc1nc2cc(C(=O)CCC(=O)O)sc2nc1OC]

Step 1: di-tert-Butyl 2-[(2,3-dimethoxythieno[2,3-b]pyrazin-6-yl)carbonyl]butanedioate

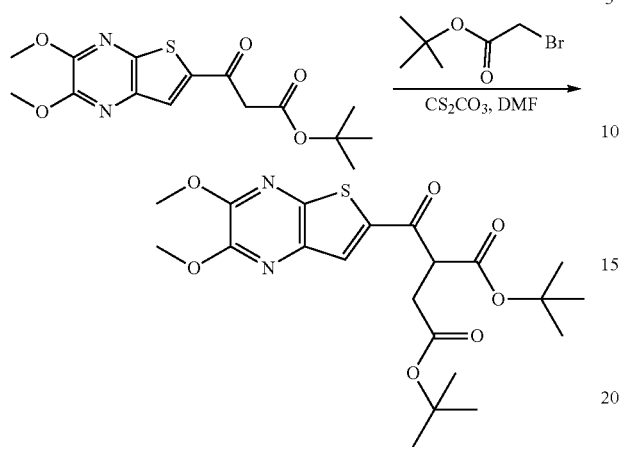

To a stirred solution of tert-butyl 3-(2,3-dimethoxythieno[2,3-b]pyrazin-6-yl)-3-oxopropanoate (Preparation 2) (21 mg, 0.062 mmol) in DMF (310 μL) was added Cs$_2$CO$_3$ (24 mg, 0.074 mmol) followed by tert-butyl bromoacetate (94, 0.06 mmol) at RT. The reaction mixture was stirred at RT for 3 hours, and then diluted with Et$_2$O and H$_2$O. The organic layers were separated, washed with brine, dried over Na$_2$SO$_4$, filtered, and concentrated under reduced pressure to afford di-tert-butyl 2-[(2,3-dimethoxythieno[2,3-b]pyrazin-6-yl)carbonyl]butane dioate, which was used without purification. LCMS (C$_{21}$H$_{29}$N$_2$O$_7$S) (ES, m/z): 453 [M+H]$^+$.

Step 2: 4-(2,3-Dimethoxythieno[2,3-b]pyrazin-6-yl)-4-oxobutanoic Acid

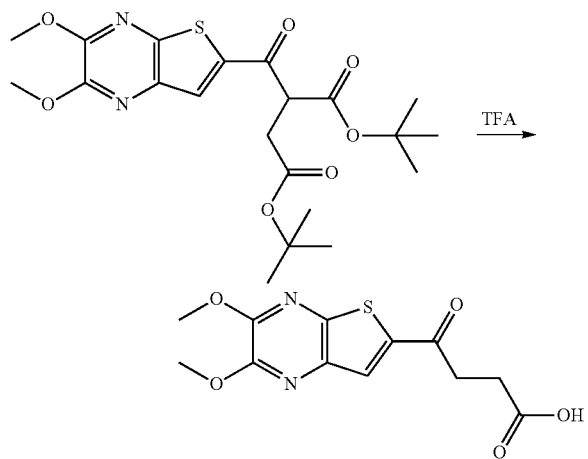

TFA (17 μL) was added to a stirred solution of di-tert-butyl 2-[(2,3-dimethoxythieno[2,3-b]pyrazin-6-yl)carbonyl]butanedioate (28 mg, 0.062 mmol) in CH$_2$Cl$_2$ (33 μL) at RT. The reaction mixture was heated to 35° C. and stirred overnight. The reaction mixture was concentrated under reduced pressure, and the residue was purified by reverse phase HPLC (eluting ACN/H$_2$O gradient with 0.1% TFA modifier, C-18 stationary phase) to afford 4-(2,3-dimethoxythieno[2,3-b]pyrazin-6-yl)-4-oxobutanoic acid. LCMS (C$_{12}$H$_{13}$N$_2$O$_5$S) (ES, m/z): 297 [M+H]$^+$. $^1$H NMR (500 MHz, DMSO-d$_6$) δ 12.21 (br s, 1H), 8.32 (s, 1H), 4.04 (s, 3H), 4.00 (s, 3H), 3.30 (t, J=6.3 Hz, 2H), 2.60 (t, J=6.2 Hz, 2H).

Example 17: (R or S)-4-(2,3-Dimethoxythieno[2,3-b]pyrazin-6-yl)-2-ethyl-4-oxobutanoic Acid

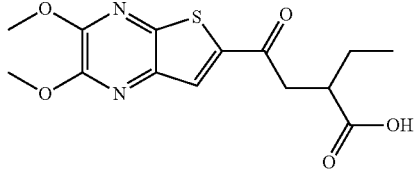 [SMILES: CCC(CC(=O)c1cc2nc(OC)c(OC)nc2s1)C(=O)O]

Step 1: 1-tert-Butyl 4-methyl 2-[(2,3-dimethoxythieno[2,3-b]pyrazin-6-yl)carbonyl]-3-ethylbutanedioate

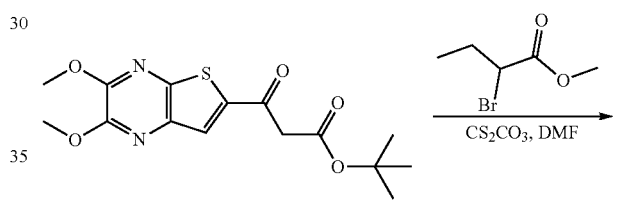

Cs$_2$CO$_3$ (173 mg, 0.532 mmol and methyl 2-bromobutyrate (75 μL, 0.65 mmol) were added to a stirred mixture of tert-butyl 3-(2,3-dimethoxythieno[2,3-b]pyrazin-6-yl)-3-oxopropanoate (Preparation 2) (90 mg, 0.27 mmol) in DMF (1.3 mL) at RT. The reaction mixture was stirred at RT for 3 hours, and then diluted with Et$_2$O and H$_2$O. The organic layers were combined, washed with brine, dried over Na$_2$SO$_4$, filtered, and concentrated under reduced pressure to afford 1-tert-butyl 4-methyl 2-[(2,3-dimethoxythieno[2,3-b]pyrazin-6-yl)carbonyl]-3-ethylbutanedioate, which was used without purification. LCMS (C$_{20}$H$_{27}$N$_2$O$_7$S—C$_4$H$_8$) (ES, m/z): 383 [M+H−tBu]$^+$.

Step 2: Methyl 4-(2,3-dimethoxythieno[2,3-b]pyrazin-6-yl)-2-ethyl-4-oxobutanoate

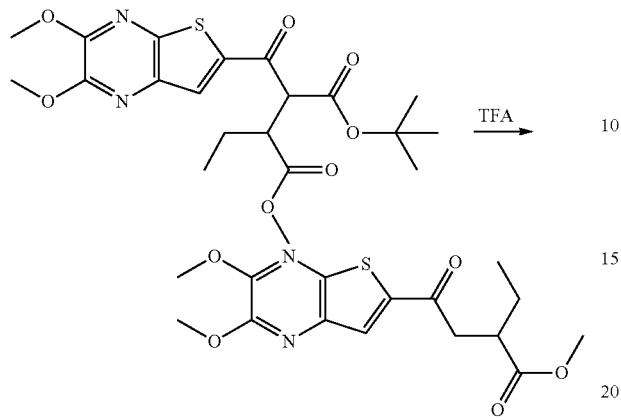

A mixture of 1-tert-butyl 4-methyl 2-[(2,3-dimethoxythieno[2,3-b]pyrazin-6-yl) carbonyl]-3-ethylbutanedioate (189 mg, 0.205 mmol) and TFA (2.0 mL) was stirred at 65° C. for 1 hour. The reaction mixture was then cooled to RT, diluted with $CH_2Cl_2$, and concentrated under reduced pressure to afford methyl 4-(2,3-dimethoxythieno[2,3-b]pyrazin-6-yl)-2-ethyl-4-oxobutanoate that was used without purification. LCMS ($C_{15}H_{19}N_2O_5S$) (ES, m/z): 339 $[M+H]^+$.

Step 3: (R or S)-4-(2,3-Dimethoxythieno[2,3-b]pyrazin-6-yl)-2-ethyl-4-oxobutanoic Acid

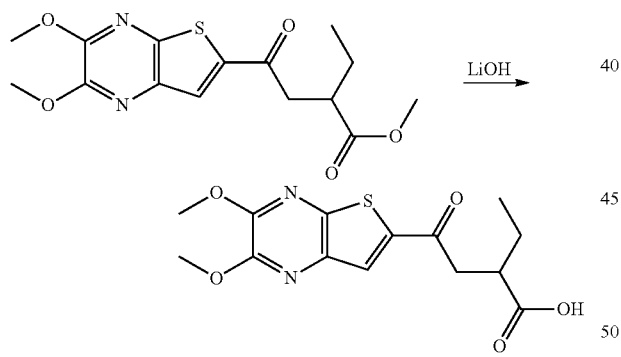

LiOH·$H_2O$ (103 mg, 2.46 mmol) and $H_2O$ (5134) were added to a stirred mixture of methyl 4-(2,3-dimethoxythieno[2,3-b]pyrazin-6-yl)-2-ethyl-4-oxobutanoate (136 mg, 0.205 mmol) in THF (1.0 mL) and MeOH (0.5 mL). The reaction mixture was stirred and heated to 40° C. for 1 hour. The reaction mixture was then cooled to RT and quenched with HCl (2N, 0.9 mL, 1.8 mmol) to pH~4. The reaction mixture was concentrated under reduced pressure. The residue was purified by reverse phase HPLC (eluting ACN/$H_2O$ with 0.1% TFA modifier, C-18 stationary phase) to afford 4-(2, 3-dimethoxythieno[2,3-b]pyrazin-6-yl)-2-ethyl-4-oxobutanoic acid as a mixture of enantiomers. The racemic mixture was resolved by Chiral-SFC (CHIRACEL OJ-H (250 mm×21 mm), 20% MeOH (with 0.25% DMEA) in $CO_2$) to afford two compounds with retention times of 2.3 min and 2.8 min. Concentration of the first eluting peak afforded (R or S)-4-(2,3-dimethoxythieno[2,3-b]pyrazin-6-yl)-2-ethyl-4-oxobutanoic acid. LCMS ($C_{14}H_{17}N_2O_5S$) (ES, m/z): 325 $[M+H]^+$. $^1H$ NMR (500 MHz, DMSO-$d_6$) δ 11.91 (br s, 1H), 8.35 (s, 1H), 4.03 (s, 3H), 4.00 (s, 3H), 3.45 (dd, J=17.5 Hz, 9.6 Hz, 1H), 3.10 (dd, J=17.0 Hz, 3.5 Hz, 1H), 2.86-2.75 (m, 1H), 1.67-1.57 (m, 2H), 0.92 (t, J=7.0 Hz, 3H).

Example 18: (R or S)-4-(2,3-Dimethoxythieno[2,3-b]pyrazin-6-yl)-2-methyl-4-oxobutanoic Acid

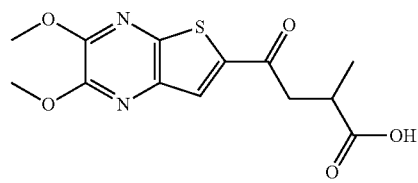 [SMILES: COc1nc2cc(C(=O)CC(C)C(=O)O)sc2nc1OC]

Step 1: di-tert-Butyl 2-[(2,3-dimethoxythieno[2,3-b]pyrazin-6-yl)carbonyl]-3-methylbutanedioate

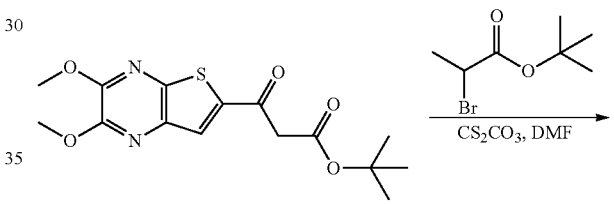

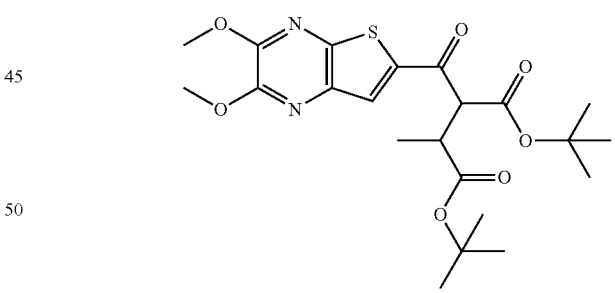

2-bromopropionic acid tert-butyl ester (584, 0.35 mmol) was added to a stirred solution of tert-butyl 3-(2,3-dimethoxythieno[2,3-b]pyrazin-6-yl)-3-oxopropanoate (59 mg, 0.17 mmol) and $Cs_2CO_3$ (114 mg, 0.349 mmol) in DMF (0.9 mL) at RT. The reaction mixture was stirred at RT for 3 hours, and then diluted with $Et_2O$ and $H_2O$. The organic layer was separated, washed with brine, dried over $Na_2SO_4$, filtered, and concentrated under reduced pressure to afford di-tert-butyl 2-[(2,3-dimethoxythieno[2,3-b]pyrazin-6-yl) carbonyl]-3-methylbutanedioate, which was used without purification. LCMS ($C_{22}H_{31}N_2O_7S$—$C_8H_{16}$) (ES, m/z): 355 $[M+H-tBu-tBu]^+$.

Step 2: (R or S)-4-(2,3-Dimethoxythieno[2,3-b]pyrazin-6-yl)-2-methyl-4-oxobutanoic Acid

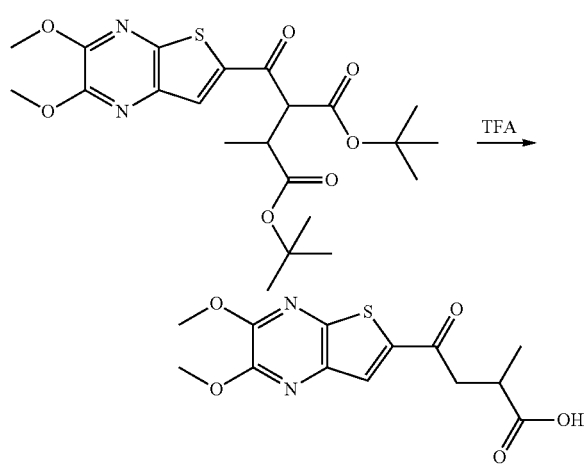

A mixture of di-tert-butyl 2-[(2,3-dimethoxythieno[2,3-b]pyrazin-6-yl)carbonyl]-3-methylbutanedioate (50 mg, 0.11 mmol) and TFA (1.0 mL) was stirred at 75° C. for 1 hour. The reaction mixture was then cooled to RT, diluted with CH$_2$Cl$_2$, and concentrated under reduced pressure. The residue was purified by reverse phase HPLC (eluting ACN/H$_2$O with 0.1% TFA modifier, C-18 stationary phase) to afford 4-(2,3-dimethoxythieno[2,3-b]pyrazin-6-yl)-2-methyl-4-oxobutanoic acid as a mixture of isomers. The racemic mixture was resolved by Chiral-SFC (Lux-4 (250 mm×21 mm), 35% MeOH (with 0.25% DMEA) in CO$_2$) to afford two products with retention times of 3.1 min and 5.1 min. The second eluting peak was concentrated under reduced pressure to afford (R or S)-4-(2,3-dimethoxythieno[2,3-b]pyrazin-6-yl)-2-methyl-4-oxobutanoic acid. LCMS (C$_{13}$H$_{15}$N$_2$O$_5$S) (ES, m/z): 311 [M+H]$^+$. $^1$H NMR (500 MHz, DMSO-d$_6$) δ 11.79 (br s, 1H), 8.30 (s, 1H), 4.03 (s, 3H), 4.00 (s, 3H), 3.44 (dd, J=17.4 Hz, 8.3 Hz, 1H), 3.07 (dd, J=17.0 Hz, 3.5 Hz, 1H), 2.93-2.81 (m, 1H), 1.17 (d, J=6.8 Hz, 3H).

Example 19: (S)-4-(5,6-Dimethoxythiazolo[4,5-b]pyridin-2-yl)-2-methyl-4-oxobutanoic Acid

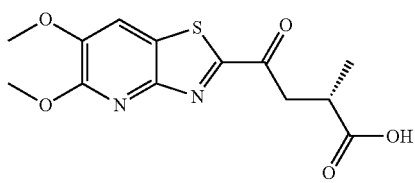 [SMILES: COc1cc2sc(C(=O)C[C@H](C)C(=O)O)nc2nc1OC]

Step 1: Methyl 2-((5,6-dimethoxypyridin-2-yl)amino)-2-oxoacetate

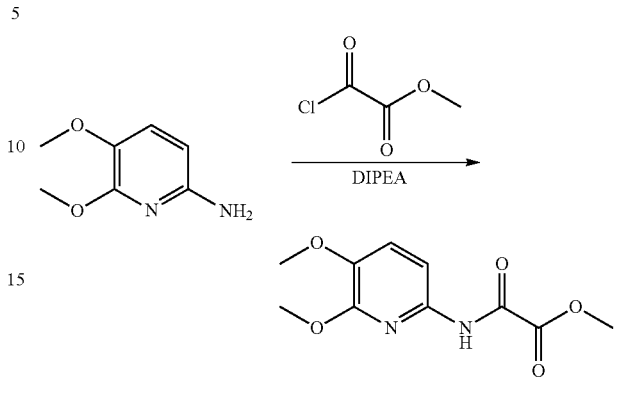

A mixture of 5,6-dimethoxypyridin-2-amine (500 mg, 3.24 mmol), N-ethyl-N-isopropylpropan-2-amine (0.861 mL, 4.86 mmol), and CH$_2$Cl$_2$ (20 mL) was cooled to 0° C. and stirred. Methyl 2-chloro-2-oxoacetate (0.36 mL, 3.9 mmol) was added dropwise to the reaction mixture over a period of 5 min. Aq NaHCO$_3$ (saturated, 2 mL) was added to the reaction mixture, and the mixture was extracted with DCM (2×30 mL). The organic layers were combined, dried over Na$_2$SO$_4$, filtered, and concentrated under reduced pressure to afford methyl 2-((5,6-dimethoxypyridin-2-yl)amino)-2-oxoacetate, which was used without purification. $^1$H NMR (499 MHz, CDCl$_3$) δ 9.11 (s, 1H), 7.78 (d, J=8.3 Hz, 1H), 7.13 (d, J=8.4 Hz, 1H), 4.00 (s, 3H), 3.99 (s, 3H), 3.89 (s, 3H).

Step 2: Methyl 2-((5,6-dimethoxypyridin-2-yl)amino)-2-thioxoacetate

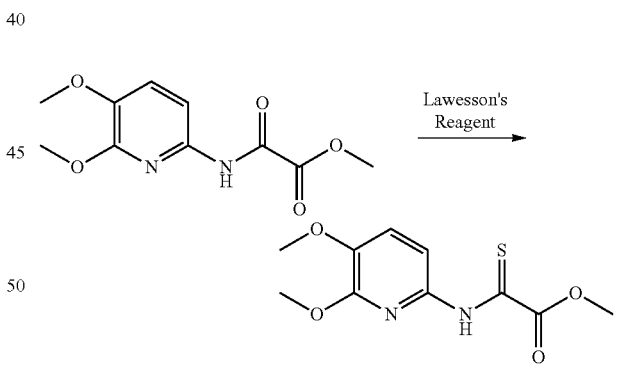

Lawesson's reagent (715 mg, 1.77 mmol) was added to a stirred mixture of methyl 2-((5,6-dimethoxypyridin-2-yl)amino)-2-oxoacetate (772 mg, 3.21 mmol) in toluene (10 mL). The reaction mixture was heated to 75° C. and stirred for 60 hours. The mixture was cooled to RT and filtered. The collected materials were washed with DCM, and the filtrate was concentrated under reduced pressure. The residue was purified by silica gel chromatography (eluting EtOAc in DCM) to afford methyl 2-((5,6-dimethoxypyridin-2-yl)amino)-2-thioxoacetate. $^1$H NMR (499 MHz, CDCl$_3$) δ 10.86 (s, 1H), 8.82 (d, J=8.4 Hz, 1H), 7.14 (d, J=8.4 Hz, 1H), 4.02 (s, 6H), 3.93 (s, 3H).

Step 3: 5,6-Dimethoxythiazolo[4,5-b]pyridine-2-carboxylic Acid

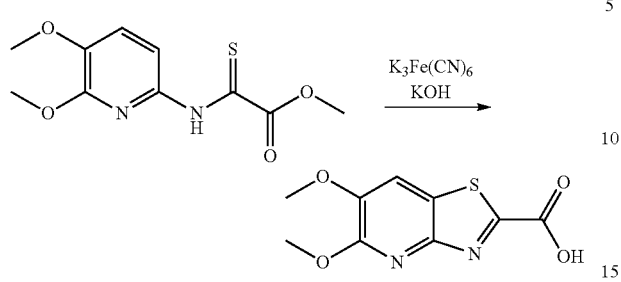

KOH (2N, 4 mL, 8 mmol) was added to a mixture of methyl 2-((5,6-dimethoxy-pyridin-2-yl)amino)-2-thioxoacetate (300 mg, 1.17 mmol) in CH$_2$Cl$_2$ (5 mL). The mixture was stirred for 10 min. The reaction mixture was partially concentrated under reduced pressure. A solution of potassium ferricyanide(III) hydrate (1.22 g, 3.51 mmol) in H$_2$O (8 mL) was added to the reaction mixture, and the mixture was stirred vigorously for 10 min. The reaction mixture was diluted with H$_2$O (40 mL), acidified to pH 2.6 with aq HCl (2N), stirred for 10 min, and filtered. The collected materials were washed with H$_2$O (3×5 mL), ACN (2×3 mL), and Et$_2$O (2×10 mL). The washed materials were then dried under reduced pressure to afford 5,6-dimethoxythiazolo[4,5-b]pyridine-2-carboxylic acid. $^1$H NMR (499 MHz, DMSO-d$_6$) δ 8.13 (s, 1H), 3.99 (s, 3H), 3.90 (s, 3H).

Step 4: 5,6-Dimethoxythiazolo[4,5-b]pyridine-2-carbonyl Chloride

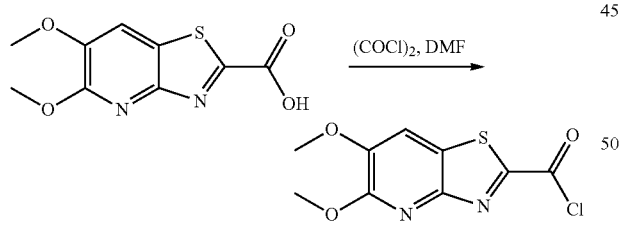

(COCl)$_2$ (0.158 mL, 1.81 mmol) was added dropwise over a period of 5 min to a stirred mixture of 5,6-dimethoxythiazolo[4,5-b]pyridine-2-carboxylic acid (207 mg, 0.860 mmol) and DMF (0.013 ml, 0.17 mmol) in CH$_2$Cl$_2$ (2 mL) at 0° C. After 15 min, the reaction mixture was warmed to RT and then stirred for an additional 30 min. The reaction mixture was concentrated under reduced pressure to afford 5,6-dimethoxythiazolo[4,5-b]pyridine-2-carbonyl chloride, which was used without purification.

Step 5: Methyl (S)-4-(5,6-dimethoxythiazolo[4,5-b]pyridin-2-yl)-2-methyl-4-oxobutanoate

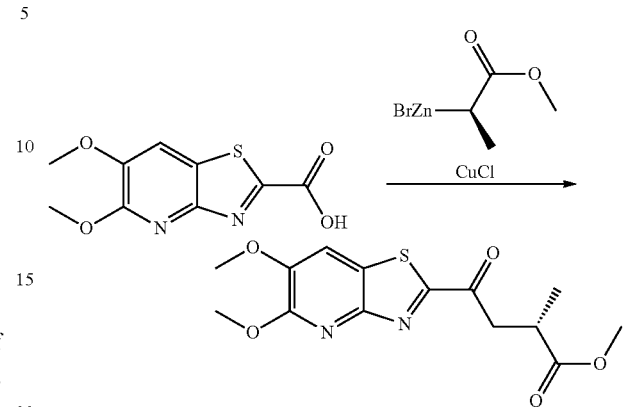

A mixture of CuCl (80 mg, 0.81 mmol) in THF (0.6 mL) was sparged with N$_2$. The mixture was stirred and cooled to 0° C. (R)-(3-methoxy-2-methyl-3-oxopropyl)zinc(II) bromide (0.50M in THF, 8.1 mL, 4.1 mmol) was added dropwise to the reaction mixture over a period of 2 min. The reaction mixture was stirred for 10 min at 0° C. A solution of 5,6-dimethoxythiazolo[4,5-b]pyridine-2-carbonyl chloride (210 mg, 0.812 mmol) in degassed NMP (4 mL) was then added dropwise over a period of 10 min to the reaction mixture. The reaction mixture was stirred for an additional 10 min. The reaction mixture was quenched by the dropwise addition of concentrated aq NH$_3$ (4 mL), diluted with EtOAc (30 mL), and washed with H$_2$O (2×40 mL). The organic layer was dried over Na$_2$SO$_4$, filtered, and concentrated under reduced pressure. The residue was purified by silica gel chromatography (eluting EtOAc in Hex) to afford (S)-methyl 4-(5,6-dimethoxythiazolo[4,5-b]pyridin-2-yl)-2-methyl-4-oxobutanoate. LCMS (C$_{14}$H$_{17}$H$_{17}$O$_5$S) (ES, m/z): 325 (M+H)$^+$. $^1$H NMR (499 MHz, CDCl$_3$) δ 7.56 (s, 1H), 4.21 (s, 3H), 4.02 (s, 3H), 3.81 (dd, J=18.4 Hz, 8.6 Hz, 1H), 3.72 (s, 3H), 3.41 (dd, J=18.4 Hz, 5.2 Hz, 1H), 3.21-3.14 (m, 1H), 1.33 (d, J=7.2 Hz, 3H).

Step 6: (S)-4-(5,6-Dimethoxythiazolo[4,5-b]pyridin-2-yl)-2-methyl-4-oxobutanoic Acid

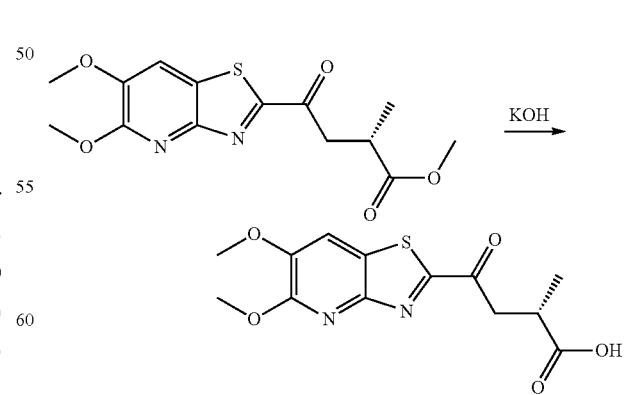

KOH (0.50M in H$_2$O, 0.31 mL, 0.15 mmol) was added dropwise to a stirred mixture of (S)-methyl 4-(5,6-dimethoxythiazolo[4,5-b]pyridin-2-yl)-2-methyl-4-oxobutanoate (24.8 mg, 0.0760 mmol) in 2-propanol (0.5 mL) at RT. After 15 min, the reaction mixture was acidified with HCl (1N) to pH~2. After stirring for an additional 5 min, the reaction mixture was filtered, and the collected materials were washed with $H_2O$ (3×2 mL). The washed materials were dissolved in DMSO (2 mL) and purified by reverse phase HPLC (eluting $ACN/H_2O$ with 0.1% TFA) to afford (S)-4-(5,6-dimethoxythiazolo[4,5-b]pyridin-2-yl)-2-methyl-4-oxobutanoic acid. LCMS ($C_{13}H_{15}N_2O_5S$) (ES, m/z): 311 $(M+H)^+$. $^1H$ NMR (499 MHz, DMSO-$d_6$) δ 12.30 (s, 1H), 8.16 (s, 1H), 4.01 (s, 3H), 3.92 (s, 3H), 3.60 (dd, J=17.9 Hz, 8.8 Hz, 1H), 3.21 (dd, J=17.9 Hz, 5.0 Hz, 1H), 3.01-2.94 (m, 1H), 1.22 (d, J=7.2 Hz, 3H).

Biological Evaluation

The individual compounds described in the Examples herein are defined as STING agonists by (i) binding to the STING protein as evidenced by a reduction in binding of tritiated cGAMP ligand to the STING protein by at least 20% at 20 uM (concentration of compound being tested) in a STING Biochemical [3H]cGAMP Competition Assay and/or (ii) demonstrating interferon production with a 6% or greater induction of IFN-β secretion at 30 uM in the THP1 cell assay (where induction caused by cGAMP at 30 μM was set at 100%).

[$^3$H]-cGAMP Synthesis 2.3 mL of buffer solution containing 80 mM TrisCl, 200 mM $MgCl_2$, and 20 mM NaCl followed by 0.32 mL of a 10 mM aq solution of GTP was added to a plastic 50 mL AMICON tube. A solution of [$^3$H]ATP (21 Ci/mmol, 45mCi) in 0.5 mL $H_2O$ was then added followed by 1 mL of a 1 mg/mL solution of DNA (Herring testes activator DNA, Sigma, #D6898) and 53 uL of a 47 mM solution of cGAS enzyme. Additional $H_2O$ was added to bring the total volume to 10 mL.

The reaction was stirred for 2 h at 37° C. and then added directly to an Amicon Ultra-15 10K centrifuge tube and spun for 1 h at 4,000 g. The collected solution was then purified on a semi-prep Mono Q column using the following mobile phases:

A: 0.05M TrisCl pH 8.5 adjusted with 1M NaOH
B: 0.05M TrisCl, 0.5M NaCl pH 8.5 adjusted with 1M NaOH
Gradient: 100% A for 5 min followed by a linear gradient to 50:50 (A:B) over 25 min, 3 mL/min, 254 nm.

The collected product fractions were pooled and adjusted to a total volume of 30 mL with buffer A. A total yield of 15.5mCi of [$^3$H]cGAMP was isolated at a radiochemical purity of 98.0% at a specific activity of 21.5 Ci/mmol.

cGAS Enzyme

A recombinant DNA vector was chemically synthesized to express the truncated human cGAS enzyme (residues 161-522). To aid in expression and purification, the amino terminus contains a hexahistidine tag, SUMO tag and TEV cleavage site. The recombinant enzyme was overexpressed in ROSETTA™ 2 (DE3) Single Competent Cells (Novagen). Affinity purification was carried out using HIS-Select HF Nickel Affinity Gel (Sigma) followed by size exclusion chromatography using a Hi-Load 26/60 SUPERDEX200 prep grade column (GE Healthcare). Fractions were pooled, concentrated, flash-frozen in liquid nitrogen and stored at −80° C. until needed.

$^3$H-cGAMP Filtration Binding Assay (HAQ STING)

The ability of compounds to bind STING is quantified by their ability to compete with tritiated cGAMP ligand for human STING receptor membrane using a radioactive filter-binding assay. The binding assay employs STING receptor obtained from *Trichoplusia ni* cell membranes (*T. ni*; Expression Systems, cat #94-002F, www.expressionsystems.com) overexpressing full-length HAQ STING and tritiated cGAMP ligand.

The basic HAQ STING filtration assay protocol is as follows:

The compounds were serially titrated by the Hamilton STARPlus CORE in a 96-well plate (Greiner, #651201) using a 1:3 ten-point dose response format. After compound preparation, a 2.2 ug/ml working concentration of STING membrane (SEQ. ID. No. 1) was prepared by diluting concentrated membrane into assay buffer (lx PBS; Invitrogen #SH30028.02) and douncing 7× using a manual tissue homogenizer (Wheaton, #357546). 148 uL of prepared membrane was then manually added to each well of a 96-well deep-well polypropylene plate (Fisher Scientific, #12-566-121). Following membrane addition, 2 uL of either titrated test compound, DMSO control (Sigma #276855), or cold cGAMP control was added to the appropriate wells using a BIOMEK FX. Compound and membrane then preincubated for 60 min at RT to allow compound binding to equilibrate. Following equilibration, 8 nM of [$^3$H] c-GAMP ligand was prepared by diluting into assay buffer, and 50 uL of this working stock was then manually added to each well of the assay plate. Plates were then incubated at RT for 60 min, and the contents of each assay plate were then filtered through a 96-well GF/B filter plate (PerkinElmer, #6005250) using a TOMTEC MACH III Cell Harvester equipped with 20 mM HEPES buffer (Fisher Scientific, #BP299500). The filter plates were then dried at 55° C. for 30 min using a pressurized oven before 30 uL of ULTIMA GOLD F scintillate was added to each well. Tritium levels for each reaction well were then measured using a PerkinElmer TopCount plate reader.

After normalization to controls, the percent activity for each compound concentration was calculated by measuring the amount of remaining radioactivity. The plot of percent activity versus the log of compound concentration was fit with a 4-parameter dose response equation to calculate $EC_{50}$ values.

The final reaction conditions were:

| Component | Volume (uL) | Final Concentration |
|---|---|---|
| STING membrane | 148 | 1.5 ug/ml |
| $^3$H-cGAMP | 50 | 2.0 nM |
| Low Control (cold cGAMP) | 2 | 10 uM |
| Test compound/DMSO | 2 | 10 uM |

Compound concentrations tested were 20.000, 637.00, 2.200, 0.740, 0.247, 0.082, 0.027, 0.009, 0.003, and 0.001 μM with 1.0% residual DMSO.

Full-Length STING (HAQ) Virus Generation

STING virus was generated using an insect cell baculovirus system. *Spodoptera frugiperda* Sf21 cells (Kempbio, Inc.) were diluted to 5e5 cells/ml in Sf-900II SFM media (LifeTechnologies #10902088) without antibiotics. The cell suspension was added to each well of a treated 6-well plate (2 mL per well, 1e6 cells total), and the cells were allowed to adhere for at least 30 min. Meanwhile, a 1 mL co-transfection mix was assembled by combining 500 ng of HAQ STING [STING(1-379)R71H,G230A,H232R,R293Q-GG-AviTag-GS-HRV3C-HIS8/pBAC1] DNA (Genewiz custom synthesis) with 1 mL Sf-900II SFM media containing 10 μL Cellfectin® II Reagent (Invitrogen #10362100) and 100 ng viral backbone BestBac 2.0, v-cath/chiA Deleted Linearized Baculovirus DNA (Expression Systems #91-

002). The transfection mixtures were allowed to incubate for 30 min. After incubation, media was gently removed from the adhered cells in the 6-well plate, the 1 mL transfection mixtures were added (1 mL per well), and the plate was placed in a humidified incubator at 27° C. The following day, 1 mL Sf-900II SFM media (no antibiotics) was added to each well of the 6-well plate. After media addition, the cells were allowed to incubate with DNA (SEQ. ID. No. 2) at 27° C. for 5-7 days to generate the P0 viral stock. To generate P1 viral stocks, 0.5 mL of P0 viral supernatant was added to 50 mL uninfected Sf21 cells (seeded the day prior to infection at a density of $5\times10^5$ cells/mL to allow for one overnight doubling) in Sf-900II SFM media containing 5 µg/mL gentamicin (Invitrogen #15710072). The infected cells were then incubated at 27° C. for 3 days while shaking at 110 rpm (ATR Biotech Multitron Infors HT #AJ118). On day 3, P1 cultures were counted using a ViCell XR (Beckman Coulter Life Sciences #383556) to confirm infection had occurred (cell size≥3 µm larger than uninfected cells and viability approximately 85-95%). Cultures were harvested in 50 mL conical tubes and centrifuged at 2000×g for 10 min at 4° C. The P1 viral supernatants were poured off into clean 50 ml centrifuge tubes, and the remaining P1 cell pellets were used to generate Baculovirus Infected Insect Cells (BIICs). Cryopreservation media containing Sf-900II SFM media with 10% heat inactivated FBS, 10% DMSO (Sigma #D2650), and 5 µg/ml gentamicin was prepared and sterilized through 0.22 µM filter immediately prior to use. P1 cell pellets were resuspended to a density of 2e7 cells/ml and aliquoted into cryovials (1 mL per vial). Cryovials were placed in Mr. Frosty™ cell freezers O/N at −80° C. and transferred to liquid nitrogen for long term storage the following day. To generate P2 viral stock, 0.5 mL of the P1 viral supernatant was added to 50 mL uninfected Sf21 cells (seeded the day prior to infection at a density of $5\times10^5$ cells/mL to allow for one overnight doubling) in Sf-900II SFM media containing 5 µg/mL gentamicin. These cells were incubated at 27° C. for 3 days while shaking at 110 rpm before harvesting P2 stock with centrifugation at 2000×g for 10 min at 4° C. The P2 viral supernatants were poured off and discarded, while the P2 cell pellets were used to generate P2 BIICs following the same protocol described above. The baculovirus generation protocol has been validated to consistently produce P1/P2 BIICs with titers of 2e9 pfu/mL (2e7 cells/mL×100 pfu/cell).

Full-Length STING (HAQ) Expression

To generate STING membranes, P1/P2 BIICs were amplified overnight by adding thawed BIICs to Sf21 cells seeded at a density of $1.0\times10^6$ cells/mL. The volume of BIIC used to infect the culture was calculated using an assumed BIIC titer of 2e9 pfu/ml to achieve an MOI of 10 in the overnight amplification. After culturing overnight, the cells were counted on a ViCell XR to confirm infection had occurred (cell size≥3 µm larger than uninfected cells and viability approximately 80-90%). The volume of infected Sf21 cells from the overnight amplification used to infect the large-scale expression of Trichoplusia ni (T. ni; Expression Systems, cat #94-002F, www.expressionsystems.com) seeded at a density of $1.0\times10^6$ in cell media (ESF921 SFM containing 5 µg/mL gentamicin) at MOI=2.0 was calculated based on (100 pfu/infected Sf21 cell). The cells were allowed to express for 48 h at 27° C. before harvesting the cell pellet, by centrifugation at 3,400×g for 10 min at 4° C. T. ni cells were counted on a ViCell XR to confirm infection had occurred (cell size≥3 µm larger than uninfected cells and viability approximately 80-90%) prior to harvest.

Full-Length STING (HAQ) Membrane Generation

Buffer Stock Reagents:
1) 1M HEPES pH 7.5, Teknova, Cat #H1035
2) 5M NaCl, Sigma Aldrich, Cat #S5150-1 L
3) KCl, Sigma Aldrich, Cat #319309-500 ML
4) Complete EDTA-free protease inhibitor tablets, Roche Diagnostics, Cat #11873580001
5) Benzonase, Universal Nuclease, Pierce, Cat #88702

Lysis buffer [25 mM HEPES pH 7.5, 10 mM $MgCl_2$, 20 mM KCl, (Benzonase 1:5000, Complete Protease Inhibitor tab/50 mL)] was added to the pellet of cells expressing full-length STING (HAQ) prepared above at 5 mL Lysis buffer per g of cell pellet. The pellet was resuspended and dounced twenty times using a Wheaton Dounce Homogenizer to disrupt the cell membrane. Homogenized lysate was then passed through the EMULSIFLEX-C5 microfluidizer at a pressure close to 5000 PSI. The resuspended pellet was centrifuged at 36,000 rpm (100,000×g) in a 45Ti rotor ultra-high speed centrifuge for 45 min, 4° C. The supernatant was removed. The pellet then was resuspended in wash buffer [(25 mM HEPES pH7.5, 1 mM $MgCl_2$, 20 mM KCl, 1M NaCl (Complete Protease Inhibitor tab/50 mL)] at a volume of 50 mL pellet/centrifuge tube. The pellet/wash buffer mixture was then homogenized, using a glass homogenizer on ice (20 strokes), followed by centrifugation at 36,000 rpm for 45 min at 4° C. The supernatant was removed. The wash step was repeated once more. The resulting membrane was resuspended in 20 mM HEPES pH 7.5, 500 mM NaCl, 10% glycerol, EDTA-free Protease Inhibitors (1 tablet/50 mL). The protein concentration was measured by Bradford assay (Bio-Rad Protein Assay, Cat #500-0006), and protein enrichment was determined by SDS-PAGE and confirmed by Western blot. The resuspended membranes were stored at −80° C.

```
Full-Length HAQ STING [STING(1-379)R71H, G230A, H232R, R293Q-GG-AviTag-GS-HRV3C-
HIS8]Amino Acid Sequence:
                                                                    (SEQ. ID. No. 1)
MPHSSLHPSIPCPRGHGAQKAALVLLSACLVTLWGLGEPPEHTLRYLVLHLASLQLGLLLNGVCSLAEELHHIHSRYRGS

YWRTVRACLGCPLRRGALLLLSIYFYYSLPNAVGPPFTWMLALLGLSQALNILLGLKGLAPAEISAVCEKGNFNVAHGLA

WSYYIGYLRLILPELQARIRTYNQHYNNLLRGAVSQRLYILLPLDCGVPDNLSMADPNIRFLDKLPQQTADRAGIKDRVY

SNSIYELLENGQRAGTCVLEYATPLQTLFAMSQYSQAGFSREDRLEQAKLFCQTLEDILADAPESQNNCRLIAYQEPADD

SSFSLSQEVLRHLRQEEKEEVTVGSLKTSAVPSTSTMSQEPELLISGMEKPLPLRTDFSGGGLNDIFEAQKIEWHEGSLE

VLFQGPHHHHHHHH
```

Full-length HAQ [STING(1-379)R71H, G230A, H232R, R293Q-GG-AviTag-GS-HRV3C-HIS8/pBAC1] Plasmid DNA Sequence:

(SEQ. ID. No. 2)

GGAACGGCTCCGCCCACTATTAATGAAATTAAAAATTCCAATTTTAAAAAACGCAGCAAGAGAAACATTTGTATGAAGA

ATGCGTAGAAGGAAAGAAAAATGTCGTCGACATGCTGAACAACAAGATTAATATGCCTCCGTGTATAAAAAAAATATTGA

ACGATTTGAAAGAAAACAATGTACCGCGCGGCGGTATGTACAGGAAGAGGTTTATACTAAACTGTTACATTGCAAACGTG

GTTTCGTGTGCCAAGTGTGAAAACCGATGTTTAATCAAGGCTCTGACGCATTTCTACAACCACGACTCCAAGTGTGTGGG

TGAAGTCATGCATCTTTTAATCAAATCCCAAGATGTGTATAAACCACCAAACTGCCAAAAAATGAAAACTGTCGACAAGC

TCTGTCCGTTTGCTGGCAACTGCAAGGGTCTCAATCCTATTTGTAATTATTGAATAATAAAACAATTATAAATGCTAAAT

TTGTTTTTTATTAACGATACAAACCAAACGCAACAAGAACATTTGTAGTATTATCTATAATTGAAAACGCGTAGTTATAA

TCGCTGAGGTAATATTTAAAATCATTTTCAAATGATTCACAGTTAATTTGCGACAATATAATTTTATTTTCACATAAACT

AGACGCCTTGTCGTCTTCTTCTTCGTATTCCTTCTCTTTTTCATTTTTCTCTTCATAAAAATTAACATAGTTATTATCGT

ATCCATATATGTATCTATCGTATAGAGTAAATTTTTTGTTGTCATAAATATATATGTCTTTTTTAATGGGGTGTATAGTA

CCGCTGCGCATAGTTTTTCTGTAATTTACAACAGTGCTATTTTCTGGTAGTTCTTCGGAGTGTGTTGCTTTAATTATTAA

ATTTATATAATCAATGAATTTGGGATCGTCGGTTTTGTACAATATGTTGCCGGCATAGTACGCAGCTTCTTCTAGTTCAA

TTACACCATTTTTTAGCAGCACCGGATTAACATAACTTTCCAAAATGTTGTACGAACCGTTAAACAAAAACAGTTCACCT

CCCTTTTCTATACTATTGTCTGCGAGCAGTTGTTTGTTGTTAAAAATAACAGCCATTGTAATGAGACGCACAAACTAATA

TCACAAACTGGAAATGTCTATCAATATATAGTTGCTGATCAGATCTGATCATGGAGATAATTAAAATGATAACCATCTCG

CAAATAAATAAGTATTTTACTGTTTTCGTAACAGTTTTGTAATAAAAAAACCTATAAATATAGGATCCATGCCCCACTCC

AGCCTGCATCCATCCATCCCGTGTCCCAGGGGTCACGGGCCCAGAAGGCAGCCTTGGTTCTGCTGAGTGCCTGCCTGGT

GACCCTTTGGGGGCTAGGAGAGCCACCAGAGCACACTCTCCGGTACCTGGTGCTCCACCTAGCCTCCCTGCAGCTGGGAC

TGCTGTTAAACGGGGTCTGCAGCCTGGCTGAGGAGCTGCACCACATCCACTCCAGGTACCGGGGCAGCTACTGGAGGACT

GTGCGGGCCTGCCTGGGCTGCCCCCTCCGCCGTGGGCCCTGTTGCTGCTGTCCATCTATTTCTACTACTCCCTCCCAAA

TGCGGTCGGCCCGCCCTTCACTTGGATGCTTGCCCTCCTGGGCCTCTCGCAGGCACTGAACATCCTCCTGGGCCTCAAGG

GCCTGGCCCCAGCTGAGATCTCTGCAGTGTGTGAAAAAGGGAATTTCAACGTGGCCCATGGGCTGGCATGGTCATATTAC

ATCGGATATCTGCGGCTGATCCTGCCAGAGCTCCAGGCCCGGATTCGAACTTACAATCAGCATTACAACAACCTGCTACG

GGGTGCAGTGAGCCAGCGGCTGTATATTCTCCTCCCATTGGACTGTGGGGTGCCTGATAACCTGAGTATGGCTGACCCCA

ACATTCGCTTCCTGGATAAACTGCCCCAGCAGACCGCTGACCGTGCTGGCATCAAGGATCGGGTTTACAGCAACAGCATC

TATGAGCTTCTGGAGAACGGGCAGCGGGCGGGCACCTGTGTCCTGGAGTACGCCACCCCCTTGCAGACTTTGTTTGCCAT

GTCACAATACAGTCAAGCTGGCTTTAGCCGGGAGGATAGGCTTGAGCAGGCCAAACTCTTCTGCCAGACACTTGAGGACA

TCCTGGCAGATGCCCCTGAGTCTCAGAACAACTGCCGCCTCATTGCCTACCAGGAACCTGCAGATGACAGCAGCTTCTCG

CTGTCCCAGGAGGTTCTCCGGCACCTGCGGCAGGAGGAAAAGGAAGAGGTTACTGTGGGCAGCTTGAAGACCTCAGCGGT

GCCCAGTACCTCCACGATGTCCCAAGAGCCTGAGCTCCTCATCAGTGGAATGGAAAAGCCCCTCCCTCTCCGCACGGATT

TCTCTGGCGGTGGCCTGAACGACATCTTCGAAGCCCAGAAAATCGAATGGCATGAAGGCAGCCTGGAAGTGCTGTTCCAG

GGCCCACACCACCATCATCACCATCACCATTAATGAGCGGCCGCACTCGAGCACCACCACCACCACCACTAACCTAGGTA

GCTGAGCGCATGCAAGCTGATCCGGGTTATTAGTACATTTATTAAGCGCTAGATTCTGTGCGTTGTTGATTTACAGACAA

TTGTTGTACGTATTTTAATAATTCATTAAATTTATAATCTTTAGGGTGGTATGTTAGAGCGAAATCAAATGATTTTCAG

CGTCTTTATATCTGAATTTAAATATTAAATCCTCAATAGATTTGTAAAATAGGTTTCGATTAGTTTCAAACAAGGGTTGT

TTTTCCGAACCGATGGCTGGACTATCTAATGGATTTTCGCTCAACGCCACAAAACTTGCCAAATCTTGTAGCAGCAATCT

AGCTTTGTCGATATTCGTTTGTGTTTTGTTTTGTAATAAAGGTTCGACGTCGTTCAAAATATTATGCGCTTTTGTATTTC

TTTCATCACTGTCGTTAGTGTACAATTGACTCGACGTAAACACGTTAAATAGAGCTTGGACATATTTAACATCGGGCGTG

TTAGCTTTATTAGGCCGATTATCGTCGTCGTCCCAACCCTCGTCGTTAGAAGTTGCTTCCGAAGACGATTTTGCCATAGC

-continued

```
CACACGACGCCTATTAATTGTGTCGGCTAACACGTCCGCGATCAAATTTGTAGTTGAGCTTTTTGGAATTATTTCTGATT
GCGGGCGTTTTTGGGCGGGTTTCAATCTAACTGTGCCCGATTTTAATTCAGACAACACGTTAGAAAGCGATGGTGCAGGC
GGTGGTAACATTTCAGACGGCAAATCTACTAATGGCGGCGGTGGTGGAGCTGATGATAAATCTACCATCGGTGGAGGCGC
AGGCGGGGCTGGCGGCGGAGGCGGAGGCGGAGGTGGTGGCGGTGATGCAGACGGCGGTTTAGGCTCAAATGTCTCTTTAG
GCAACACAGTCGGCACCTCAACTATTGTACTGGTTTCGGGCGCCGTTTTTGGTTTGACCGGTCTGAGACGAGTGCGATTT
TTTTCGTTTCTAATAGCTTCCAACAATTGTTGTCTGTCGTCTAAAGGTGCAGCGGGTTGAGGTTCCGTCGGCATTGGTGG
AGCGGGCGGCAATTCAGACATCGATGGTGGTGGTGGTGGAGGCGCTGGAATGTTAGGCACGGGAGAAGGTGGTGGCG
GCGGTGCCGCCGGTATAATTTGTTCTGGTTTAGTTTGTTCGCGCACGATTGTGGGCACCGGCGCAGGCGCCGCTGGCTGC
ACAACGGAAGGTCGTCTGCTTCGAGGCAGCGCTTGGGGTGGTGGCAATTCAATATTATAATTGGAATACAAATCGTAAAA
ATCTGCTATAAGCATTGTAATTTCGCTATCGTTTACCGTGCCGATATTTAACAACCGCTCAATGTAAGCAATTGTATTGT
AAAGAGATTGTCTCAAGCTCGGATCGATCCCGCACGCCGATAACAAGCCTTTTCATTTTTACTACAGCATTGTAGTGGCG
AGACACTTCGCTGTCGTCGAGGTTTAAACGCTTCCTCGCTCACTGACTCGCTGCGCTCGGTCGTTCGGCTGCGGCGAGCG
GTATCAGCTCACTCAAAGGCGGTAATACGGTTATCCACAGAATCAGGGGATAACGCAGGAAAGAACATGTGAGCAAAAGG
CCAGCAAAAGGCCAGGAACCGTAAAAAGGCCGCGTTGCTGGCGTTTTTCCATAGGCTCCGCCCCCCTGACGAGCATCACA
AAAATCGACGCTCAAGTCAGAGGTGGCGAAACCCGACAGGACTATAAAGATACCAGGCGTTTCCCCCTGGAAGCTCCCTC
GTGCGCTCTCCTGTTCCGACCCTGCCGCTTACCGGATACCTGTCCGCCTTTCTCCCTTCGGGAAGCGTGGCGCTTTCTCA
TAGCTCACGCTGTAGGTATCTCAGTTCGGTGTAGGTCGTTCGCTCCAAGCTGGGCTGTGTGCACGAACCCCCCGTTCAGC
CCGACCGCTGCGCCTTATCCGGTAACTATCGTCTTGAGTCCAACCCGGTAAGACACGACTTATCGCCACTGGCAGCAGCC
ACTGGTAACAGGATTAGCAGAGCGAGGTATGTAGGCGGTGCTACAGAGTTCTTGAAGTGGTGGCCTAACTACGGCTACAC
TAGAAGGACAGTATTTGGTATCTGCGCTCTGCTGAAGCCAGTTACCTTCGGAAAAAGAGTTGGTAGCTCTTGATCCGGCA
AACAAACCACCGCTGGTAGCGGTGGTTTTTTTGTTTGCAAGCAGCAGATTACGCGCAGAAAAAAAGGATCTCAAGAAGAT
CCTTTGATCTTTTCTACGGGGTCTGACGCTCAGTGGAACGAAAACTCACGTTAAGGGATTTTGGTCATGAGATTATCAAA
AAGGATCTTCACCTAGATCCTTTTAAATTAAAAATGAAGTTTTAAATCAATCTAAAGTATATATGAGTAAACTTGGTCTG
ACAGTTACCAATGCTTAATCAGTGAGGCACCTATCTCAGCGATCTGTCTATTTCGTTCATCCATAGTTGCCTGACTCCCC
GTCGTGTAGATAACTACGATACGGGAGGGCTTACCATCTGGCCCCAGTGCTGCAATGATACCGCGAGACCCACGCTCACC
GGCTCCAGATTTATCAGCAATAAACCAGCCAGCCGGAAGGGCCGAGCGCAGAAGTGGTCCTGCAACTTTATCCGCCTCCA
TCCAGTCTATTAATTGTTGCCGGGAAGCTAGAGTAAGTAGTTCGCCAGTTAATAGTTTGCGCAACGTTGTTGCCATTGCT
ACAGGCATCGTGGTGTCACGCTCGTCGTTTGGTATGGCTTCATTCAGCTCCGGTTCCCAACGATCAAGGCGAGTTACATG
ATCCCCCATGTTGTGCAAAAAAGCGGTTAGCTCCTTCGGTCCTCCGATCGTTGTCAGAAGTAAGTTGGCCGCAGTGTTAT
CACTCATGGTTATGGCAGCACTGCATAATTCTCTTACTGTCATGCCATCCGTAAGATGCTTTTCTGTGACTGGTGAGTAC
TCAACCAAGTCATTCTGAGAATAGTGTATGCGGCGACCGAGTTGCTCTTGCCCGGCGTCAATACGGGATAATACCGCGCC
ACATAGCAGAACTTTAAAAGTGCTCATCATTGGAAAACGTTCTTCGGGGCGAAAACTCTCAAGGATCTTACCGCTGTTGA
GATCCAGTTCGATGTAACCCACTCGTGCACCCAACTGATCTTCAGCATCTTTTACTTTCACCAGCGTTTCTGGGTGAGCA
AAAACAGGAAGGCAAAATGCCGCAAAAAAGGGAATAAGGGCGACACGGAAATGTTGAATACTCATACTCTTCCTTTTTCA
ATATTATTGAAGCATTTATCAGGGTTATTGTCTCATGAGCGGATACATATTTGAATGTATTTAGAAAAATAAACAAATAG
GGGTTCCGCGCACATTTCCCCGAAAAGTGCCACCTGACGCGCCCTGTAGCGGCGCATTAAGCGCGGCGGGTGTGGTGGTT
ACGCGCAGCGTGACCGCTACACTTGCCAGCGCCCTAGCGCCCGCTCCTTTCGCTTTCTTCCCTTCCTTTCTCGCCACGTT
CGCCGGCTTTCCCCGTCAAGCTCTAAATCGGGGGCTCCCTTTAGGGTTCCGATTTAGTGCTTTACGGCACCTCGACCCCA
AAAAACTTGATTAGGGTGATGGTTCACGTAGTGGGCCATCGCCCTGATAGACGGTTTTTCGCCCTTTGACGTTGGAGTCC
ACGTTCTTTAATAGTGGACTCTTGTTCCAAACTGGAACAACACTCAACCCTATCTCGGTCTATTCTTTTGATTTATAAGG
```

```
-continued
GATTTTGCCGATTTCGGCCTATTGGTTAAAAAATGAGCTGATTTAACAAAAATTTAACGCGAATTTTAACAAAATATTAA

CGTTTACAATTTCCCATTCGCCATTCAGGCTGCGCAACTGTTGGGAAGGGCGATCGGTGCGGGCCTCTTCGCTATTACGC

CA
```

Certain compounds of the disclosure were evaluated in HAQ STING in vitro binding assay as described above. The following table tabulates the biological data for these compounds as $EC_{50}$ values.

TABLE 1

| 3H-cGAMP filtration binding assay for HAQ STING | |
|---|---|
| Compound | $EC_{50}$ (nM) |
| Example 1 | 13,300 |
| Example 2 | 3290 |
| Example 3 | 10600 |
| Example 4 | 6790 |
| Example 5 | 5510 |
| Example 6 | 2440 |
| Example 7 | 8760 |
| Example 8 | 1540 |
| Example 9 | 1150 |
| Example 10 | 637 |
| Example 11 | 17300 |
| Example 12 | 1750 |
| Example 13 | 7% @ 20,000 |
| Example 14 | 1390 |
| Example 15 | 2450 |
| Example 16 | 9570 |
| Example 17 | 2710 |
| Example 18 | 4500 |
| Example 19 | 10,100 |

IFN-β Secretion in THP1 Cell Culture (5 h)

The ability of compounds to stimulate the secretion of interferon-beta from THP1 cells was measured using a human IFN-β AlphaLISA kit (Perkin Elmer, Cat. No. AL265F). The basic protocol is as follows:

A Labcyte Echo 550 acoustic dispenser was used to transfer 120 nL of compound dissolved in DMSO into the wells of an empty, sterile 384-well microplate, (Corning, Cat. No. 3712). THP1 cells (American Type Culture Collection, Cat. No. TIB202) previously frozen in Recovery Medium (Life Technologies, Cat. No. 12648-010) were thawed and immediately diluted 10-fold into 37° C. assay medium (RPMI 1640+L-Glutamine & phenol red, Life Technologies, Cat. No. 11875-085; 0.5% heat inactivated fetal bovine serum, Sigma Aldrich, Cat. No. F4135; 1 mM Sodium Pyruvate, Life Technologies, Cat. No. 11360-070; lx non-essential amino acids; Life Technologies, Cat. No. 11140-050). The cell viability and count was ascertained using a Beckman Coulter V-Cell XR cell counter. The cells suspension was centrifuged at 200×g for 5 min at RT. Cells were resuspended to a density of $0.8 \times 10^6$/mL in 37° C. assay medium. Subsequent liquid transfers were performed using either a Matrix electronic multichannel pipette or an Agilent Bravo Automated Liquid Handling Platform.

The assay was started by dispensing 404, of the previously prepared cell suspension into the wells of the plate containing compounds. After 5 h incubation at 37° C., 5% $CO_2$ in a humidified atmosphere, the plate of cells and compounds was centrifuged at 200×g for 5 min at RT. From each well, 54, of supernatant was transferred into corresponding wells of a white 384-well plate (Perkin Elmer, Cat. No. 6005620). To these supernatant-containing wells was added 10 μL of 5× Anti-Analyte Acceptor beads (50 μg/mL of AlphaLISA HiBlock Buffer) and incubated for 30 min at RT while shaking on an orbital plate shaker. To each well was added 104, of 5× Biotinylated Antibody Anti-analyte (5 nM in AlphaLISA HiBlock Buffer) and incubated on an orbital plate shaker for 60 min at RT or overnight at 4° C. To each well was added 254, of 2× SA-Donor beads (80 μg/mL in AlphaLISA HiBlock Buffer) and incubated for 30-45 min at RT in the dark while shaking on an orbital plate shaker. The plate was then read on a Perkin Elmer Envision ($\lambda_{ex}$=680 nm, $\lambda_{em}$=570 nm). The percent effect of the AlphaLISA signal at each compound concentration was calculated based on 30 uM cGAMP positive controls and 0.3% DMSO negative controls. The plot of percent effect versus the log of compound concentration was fit with a 4-parameter concentration response equation to calculate $EC_{50}$ values. The test compounds were tested at concentrations 30000, 10000, 3333, 1111, 370.4, 123.4, 41.2, 13.7, 4.6, and 1.5 nM with 0.3% residual DMSO. The control compound, cGAMP was tested at concentrations 100000, 33333, 11111, 3704, 1235, 412, 137, 46, and 15 nM with 0.3% residual DMSO.

Compounds of the disclosure were evaluated for IFN-β secretion in THP1 cell culture as described above. The following table tabulates the biological data for these compounds as percent activation relative to 2'3'-cGAMP at the 30 μM concentration.

TABLE 2

| IFN-β secretion in THP1 cell culture (5 h) | |
|---|---|
| Compound | % Effect at 30 μM relative to 2'3'-cGAMP |
| Example 1 | 56 |
| Example 2 | 94 |
| Example 3 | 11 |
| Example 4 | 19 |
| Example 5 | 146 |
| Example 6 | 107 |
| Example 7 | 55 |
| Example 8 | 55 |
| Example 9 | 100 |
| Example 10 | 70 |
| Example 11 | 58 |
| Example 12 | 85 |
| Example 13 | 55 |
| Example 14 | 89 |
| Example 15 | 142 |
| Example 16 | 108 |
| Example 17 | 116 |
| Example 18 | 77 |
| Example 19 | 14 |

It will be appreciated that various of the above-discussed and other features and functions, or alternatives thereof, may be desirably combined into many other different systems or applications. It also will be appreciated that various presently unforeseen or unanticipated alternatives, modifications, variations or improvements therein may be subsequently made by those skilled in the art and are also intended to be encompassed by the following claims.

SEQUENCE LISTING

<160> NUMBER OF SEQ ID NOS: 2

<210> SEQ ID NO 1
<211> LENGTH: 414
<212> TYPE: PRT
<213> ORGANISM: Artificial Sequence
<220> FEATURE:
<223> OTHER INFORMATION: Full-Length HAQ STING
      [STING(1-379)R71H,G230A,H232R,R293Q-GG-AviTag-GS-HRV3C-HIS8]Amino
      Acid Sequence

<400> SEQUENCE: 1

```
Met Pro His Ser Ser Leu His Pro Ser Ile Pro Cys Pro Arg Gly His
1               5                   10                  15

Gly Ala Gln Lys Ala Ala Leu Val Leu Leu Ser Ala Cys Leu Val Thr
            20                  25                  30

Leu Trp Gly Leu Gly Glu Pro Pro Glu His Thr Leu Arg Tyr Leu Val
        35                  40                  45

Leu His Leu Ala Ser Leu Gln Leu Gly Leu Leu Leu Asn Gly Val Cys
50                  55                  60

Ser Leu Ala Glu Glu Leu His His Ile His Ser Arg Tyr Arg Gly Ser
65                  70                  75                  80

Tyr Trp Arg Thr Val Arg Ala Cys Leu Gly Cys Pro Leu Arg Arg Gly
                85                  90                  95

Ala Leu Leu Leu Leu Ser Ile Tyr Phe Tyr Tyr Ser Leu Pro Asn Ala
            100                 105                 110

Val Gly Pro Pro Phe Thr Trp Met Leu Ala Leu Leu Gly Leu Ser Gln
        115                 120                 125

Ala Leu Asn Ile Leu Leu Gly Leu Lys Gly Leu Ala Pro Ala Glu Ile
130                 135                 140

Ser Ala Val Cys Glu Lys Gly Asn Phe Asn Val Ala His Gly Leu Ala
145                 150                 155                 160

Trp Ser Tyr Tyr Ile Gly Tyr Leu Arg Leu Ile Leu Pro Glu Leu Gln
                165                 170                 175

Ala Arg Ile Arg Thr Tyr Asn Gln His Tyr Asn Asn Leu Leu Arg Gly
            180                 185                 190

Ala Val Ser Gln Arg Leu Tyr Ile Leu Leu Pro Leu Asp Cys Gly Val
        195                 200                 205

Pro Asp Asn Leu Ser Met Ala Asp Pro Asn Ile Arg Phe Leu Asp Lys
210                 215                 220

Leu Pro Gln Gln Thr Ala Asp Arg Ala Gly Ile Lys Asp Arg Val Tyr
225                 230                 235                 240

Ser Asn Ser Ile Tyr Glu Leu Leu Glu Asn Gly Gln Arg Ala Gly Thr
                245                 250                 255

Cys Val Leu Glu Tyr Ala Thr Pro Leu Gln Thr Leu Phe Ala Met Ser
            260                 265                 270

Gln Tyr Ser Gln Ala Gly Phe Ser Arg Glu Asp Arg Leu Glu Gln Ala
        275                 280                 285

Lys Leu Phe Cys Gln Thr Leu Glu Asp Ile Leu Ala Asp Ala Pro Glu
290                 295                 300

Ser Gln Asn Asn Cys Arg Leu Ile Ala Tyr Gln Glu Pro Ala Asp Asp
305                 310                 315                 320

Ser Ser Phe Ser Leu Ser Gln Glu Val Leu Arg His Leu Arg Gln Glu
                325                 330                 335

Glu Lys Glu Glu Val Thr Val Gly Ser Leu Lys Thr Ser Ala Val Pro
            340                 345                 350
```

```
Ser Thr Ser Thr Met Ser Gln Glu Pro Glu Leu Leu Ile Ser Gly Met
        355                 360                 365

Glu Lys Pro Leu Pro Leu Arg Thr Asp Phe Ser Gly Gly Gly Leu Asn
    370                 375                 380

Asp Ile Phe Glu Ala Gln Lys Ile Glu Trp His Glu Gly Ser Leu Glu
385                 390                 395                 400

Val Leu Phe Gln Gly Pro His His His His His His His His
                405                 410

<210> SEQ ID NO 2
<211> LENGTH: 6482
<212> TYPE: DNA
<213> ORGANISM: Artificial Sequence
<220> FEATURE:
<223> OTHER INFORMATION: Full-length HAQ
      [STING(1-379)R71H,G230A,H232R,R293Q-GG-AviTag-GS-HRV3C-HIS8/pBAC1]
      Plasmid DNA Sequence

<400> SEQUENCE: 2
```

| | | |
|---|---|---|
| ggaacggctc cgcccactat taatgaaatt aaaaattcca attttaaaaa acgcagcaag | 60 |
| agaaacattt gtatgaaaga atgcgtagaa ggaaagaaaa atgtcgtcga catgctgaac | 120 |
| aacaagatta atatgcctcc gtgtataaaa aaaatattga acgatttgaa agaaaacaat | 180 |
| gtaccgcgcg gcggtatgta caggaagagg tttatactaa actgttacat tgcaaacgtg | 240 |
| gtttcgtgtg ccaagtgtga aaaccgatgt ttaatcaagg ctctgacgca tttctacaac | 300 |
| cacgactcca gtgtgtgggg tgaagtcatg catcttttaa tcaaatccca agatgtgtat | 360 |
| aaaccaccaa actgccaaaa aatgaaaact gtcgacaagc tctgtccgtt tgctggcaac | 420 |
| tgcaagggtc tcaatcctat ttgtaattat tgaataataa acaattata aatgctaaat | 480 |
| ttgttttta ttaacgatac aaaccaaacg caacaagaac atttgtagta ttatctataa | 540 |
| ttgaaaacgc gtagttataa tcgctgaggt aatatttaaa atcattttca aatgattcac | 600 |
| agttaatttg cgacaatata attttatttt cacataaact agacgccttg tcgtcttctt | 660 |
| cttcgtattc cttctctttt tcatttttct cttcataaaa attaacatag ttattatcgt | 720 |
| atccatatat gtatctatcg tatagagtaa atttttttgtt gtcataaata tatatgtctt | 780 |
| ttttaatggg gtgtatagta ccgctgcgca tagtttttct gtaatttaca acagtgctat | 840 |
| tttctggtag ttcttcggag tgtgttgctt taattattaa atttatataa tcaatgaatt | 900 |
| tgggatcgtc ggttttgtac aatatgttgc cggcatagta cgcagcttct tctagttcaa | 960 |
| ttacaccatt ttttagcagc accgattaa cataactttc caaaatgttg tacgaaccgt | 1020 |
| taaacaaaaa cagttcacct ccctttttcta tactattgtc tgcgagcagt tgtttgttgt | 1080 |
| taaaaataac agccattgta atgagacgca caaactaata tcacaaactg gaaatgtcta | 1140 |
| tcaatatata gttgctgatc agatctgatc atggagataa ttaaaatgat aaccatctcg | 1200 |
| caaataaata gtatttttac tgtttttcgta acagttttgt aataaaaaaa cctataaata | 1260 |
| taggatccat gccccactcc agcctgcatc catccatccc gtgtcccagg ggtcacgggg | 1320 |
| cccagaaggc agccttggtt ctgctgagtg cctgcctggt gacccctttgg gggctaggag | 1380 |
| agccaccaga gcacactctc cggtacctgg tgctccacct agcctccctg cagctgggac | 1440 |
| tgctgttaaa cggggtctgc agcctggctg aggagctgca ccacatccac tccaggtacc | 1500 |
| ggggcagcta ctggaggact gtgcgggcct gctgggctg ccccctccgc cgtggggccc | 1560 |
| tgttgctgct gtccatctat ttctactact ccctcccaaa tgcggtcggc ccgcccttca | 1620 |

```
cttggatgct tgccctcctg ggcctctcgc aggcactgaa catcctcctg ggcctcaagg   1680
gcctggcccc agctgagatc tctgcagtgt gtgaaaaagg gaatttcaac gtggcccatg   1740
ggctggcatg gtcatattac atcggatatc tgcggctgat cctgccagag ctccaggccc   1800
ggattcgaac ttacaatcag cattacaaca acctgctacg gggtgcagtg agccagcggc   1860
tgtatattct cctcccattg gactgtgggg tgcctgataa cctgagtatg gctgacccca   1920
acattcgctt cctggataaa ctgcccagc agaccgctga ccgtgctggc atcaaggatc    1980
gggtttacag caacagcatc tatgagcttc tggagaacgg gcagcgggcg ggcacctgtg   2040
tcctggagta cgccacccc ttgcagactt tgtttgccat gtcacaatac agtcaagctg    2100
gctttagccg ggaggatagg cttgagcagg ccaaactctt ctgccagaca cttgaggaca   2160
tcctggcaga tgcccctgag tctcagaaca actgccgcct cattgcctac caggaacctg   2220
cagatgacag cagcttctcg ctgtcccagg aggttctccg gcacctgcgg caggaggaaa   2280
aggaagaggt tactgtgggc agcttgaaga cctcagcggt gcccagtacc tccacgatgt   2340
cccaagagcc tgagctcctc atcagtggaa tggaaaagcc cctccctctc cgcacggatt   2400
tctctggcgg tggcctgaac gacatcttcg aagcccagaa aatcgaatgg catgaaggca   2460
gcctggaagt gctgttccag ggcccacacc accatcatca ccatcaccat taatgagcgg   2520
ccgcactcga gcaccaccac caccaccact aacctaggta gctgagcgca tgcaagctga   2580
tccgggttat tagtacattt attaagcgct agattctgtg cgttgttgat ttacagacaa   2640
ttgttgtacg tattttaata attcattaaa tttataatct ttagggtggt atgttagagc   2700
gaaaatcaaa tgattttcag cgtctttata tctgaattta aatattaaat cctcaataga   2760
tttgtaaaat aggtttcgat tagtttcaaa caagggttgt ttttccgaac cgatggctgg   2820
actatctaat ggattttcgc tcaacgccac aaaacttgcc aaatcttgta gcagcaatct   2880
agctttgtcg atattcgttt gtgttttgtt ttgtaataaa ggttcgacgt cgttcaaaat   2940
attatgcgct tttgtatttc tttcatcact gtcgttagtg tacaattgac tcgacgtaaa   3000
cacgttaaat agagcttgga catatttaac atcgggcgtg ttagctttat taggccgatt   3060
atcgtcgtcg tcccaaccct cgtcgttaga agttgcttcc gaagacgatt tgccatagc    3120
cacacgacgc ctattaattg tgtcggctaa cacgtccgcg atcaaatttg tagttgagct   3180
ttttggaatt atttctgatt gcgggcgttt tgggcgggt ttcaatctaa ctgtgcccga   3240
ttttaattca gacaacacgt tagaaagcga tggtgcaggc ggtggtaaca tttcagacgg   3300
caaatctact aatggcggcg gtggtggagc tgatgataaa tctaccatcg gtggaggcgc   3360
aggcggggct ggcggcggag gcggaggcgg aggtggtggc ggtgatgcag acggcggttt   3420
aggctcaaat gtctctttag caacacagt cggcacctca actattgtac tggtttcggg    3480
cgccgttttt ggtttgaccg gtctgagacg agtgcgattt ttttcgtttc taatagcttc   3540
caacaattgt tgtctgtcgt ctaaaggtgc agcgggttga ggttccgtcg gcattggtgg   3600
agcgggcggc aattcagaca tcgatggtgg tggtggtggt ggaggcgctg gaatgttagg   3660
cacgggagaa ggtggtggcg gcggtgccgc cggtataatt tgttctggtt agtttgttc    3720
gcgcacgatt gtgggcaccg gcgcaggcgc cgctggctgc acaacggaag gtcgtctgct   3780
tcgaggcagc gcttggggtg gtggcaattc aatattataa ttggaataca aatcgtaaaa   3840
atctgctata agcattgtaa tttcgctatc gtttaccgtg ccgatattta acaaccgctc   3900
aatgtaagca attgtattgt aaagagattg tctcaagctc ggatcgatcc cgcacgccga   3960
taacaagcct tttcattttt actacagcat tgtagtggcg agacacttcg ctgtcgtcga   4020
```

```
ggtttaaacg cttcctcgct cactgactcg ctgcgctcgg tcgttcggct gcggcgagcg    4080
gtatcagctc actcaaaggc ggtaatacgg ttatccacag aatcagggga taacgcagga    4140
aagaacatgt gagcaaaagg ccagcaaaag gccaggaacc gtaaaaaggc cgcgttgctg    4200
gcgtttttcc ataggctccg cccccctgac gagcatcaca aaaatcgacg ctcaagtcag    4260
aggtggcgaa acccgacagg actataaaga taccaggcgt ttccccctgg aagctccctc    4320
gtgcgctctc ctgttccgac cctgccgctt accggatacc tgtccgcctt tctcccttcg    4380
ggaagcgtgg cgctttctca tagctcacgc tgtaggtatc tcagttcggt gtaggtcgtt    4440
cgctccaagc tgggctgtgt gcacgaaccc cccgttcagc ccgaccgctg cgccttatcc    4500
ggtaactatc gtcttgagtc caacccggta agacacgact tatcgccact ggcagcagcc    4560
actggtaaca ggattagcag agcgaggtat gtaggcggtg ctacagagtt cttgaagtgg    4620
tggcctaact acggctacac tagaaggaca gtatttggta tctgcgctct gctgaagcca    4680
gttaccttcg gaaaaagagt tggtagctct tgatccggca aacaaaccac cgctggtagc    4740
ggtggttttt ttgtttgcaa gcagcagatt acgcgcagaa aaaaggatc tcaagaagat    4800 cctttgatct tttctacggg gtctgacgct cagtggaacg aaaactcacg ttaagggatt    4860
ttggtcatga gattatcaaa aaggatcttc acctagatcc ttttaaatta aaaatgaagt    4920
tttaaatcaa tctaaagtat atatgagtaa acttggtctg acagttacca atgcttaatc    4980
agtgaggcac ctatctcagc gatctgtcta tttcgttcat ccatagttgc ctgactcccc    5040
gtcgtgtaga taactacgat acgggagggc ttaccatctg gccccagtgc tgcaatgata    5100
ccgcgagacc cacgctcacc ggctccagat ttatcagcaa taaaccagcc agccggaagg    5160
gccgagcgca gaagtggtcc tgcaacttta tccgcctcca tccagtctat taattgttgc    5220
cgggaagcta gagtaagtag ttcgccagtt aatagtttgc gcaacgttgt tgccattgct    5280
acaggcatcg tggtgtcacg ctcgtcgttt ggtatggctt cattcagctc cggttcccaa    5340
cgatcaaggc gagttacatg atcccccatg ttgtgcaaaa aagcggttag ctccttcggt    5400
cctccgatcg ttgtcagaag taagttggcc gcagtgttat cactcatggt tatggcagca    5460
ctgcataatt ctcttactgt catgccatcc gtaagatgct tttctgtgac tggtgagtac    5520
tcaaccaagt cattctgaga atagtgtatg cggcgaccga gttgctcttg cccggcgtca    5580
atacgggata ataccgcgcc acatagcaga actttaaaag tgctcatcat tggaaaacgt    5640 tcttcgggc gaaaactctc aaggatctta ccgctgttga tccagttc gatgtaaccc       5700 actcgtgcac ccaactgatc ttcagcatct tttactttca ccagcgtttc tgggtgagca    5760
aaaacaggaa ggcaaaatgc cgcaaaaaag ggaataaggg cgacacggaa atgttgaata    5820
ctcatactct ccttttttca atattattga agcatttatc agggttattg tctcatgagc    5880
ggatacatat ttgaatgtat ttagaaaaat aaacaaatag gggttccgcg cacatttccc    5940
cgaaaagtgc cacctgacgc gccctgtagc ggcgcattaa gcgcggcggg tgtggtggtt    6000
acgcgcagcg tgaccgctac acttgccagc gccctagcgc ccgctccttt cgctttcttc    6060
ccttcctttc tcgccacgtt cgccggcttt ccccgtcaag ctctaaatcg ggggctccct    6120
ttagggttcc gatttagtgc tttacggcac ctcgacccca aaaaacttga ttagggtgat    6180
ggttcacgta gtgggccatc gccctgatag acggtttttc gccctttgac gttggagtcc    6240
acgttcttta atagtggact cttgttccaa actggaacaa cactcaaccc tatctcggtc    6300
tattcttttg atttataagg gattttgccg atttcggcct attggttaaa aaatgagctg    6360
```

| | |
|---|---|
| atttaacaaa aatttaacgc gaattttaac aaaatattaa cgtttacaat ttcccattcg | 6420 |
| ccattcaggc tgcgcaactg ttgggaaggg cgatcggtgc gggcctcttc gctattacgc | 6480 |
| ca | 6482 |

What is claimed is:

1. A compound of formula (I):

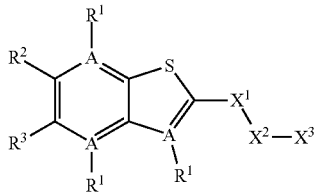

or a pharmaceutically acceptable salt thereof, wherein each A-$R^1$ is selected independently from the group consisting of C—$R^1$ and N, and

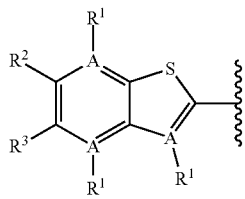

is selected from the group consisting of

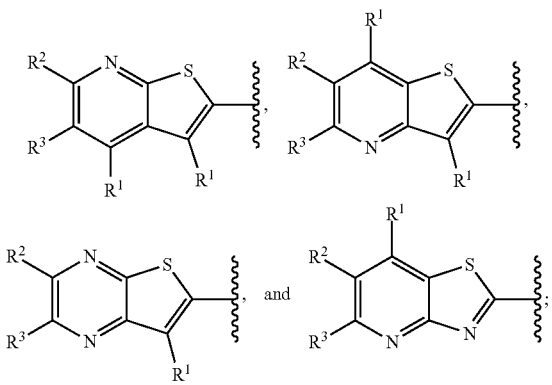

each $R^1$ is selected independently from the group consisting of H, halogen, $OR^6$, $N(R^6)_2$, $SR^6$, $C_1$-$C_6$ alkyl, $C_1$-$C_6$ haloalkyl, $C_1$-$C_6$ alkyl substituted by $OR^6$, $C_1$-$C_6$ alkyl substituted by $SR^6$, $C_1$-$C_6$ alkyl substituted by $N(R^6)_2$, $C_1$-$C_6$ haloalkyl substituted by $OR^6$, $C_1$-$C_6$ haloalkyl substituted by $SR^6$, and $C_1$-$C_6$ haloalkyl substituted by $N(R^6)_2$;

$R^2$ is selected from the group consisting of halogen, CN, $OR^6$, $N(R^6)_2$, $COOR^6$, $C(O)N(R^6)_2$, $SR^6$, $SO_2R^6$, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and a 3- to 6-membered heterocyclic ring including 1 to 2 ring members selected from the group consisting of O, S, N, and N($R^6$), wherein said $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and 3- to 6-membered heterocyclic ring groups are optionally substituted by one or more substituents independently selected from the group consisting of CN, $OR^6$, $N(R^6)_2$, and $SR^6$, and wherein said $C_3$-$C_6$ cycloalkyl and 3- to 6-membered heterocyclic ring are each further optionally substituted with a member of the group consisting of $C_1$-$C_3$ alkyl and $C_1$-$C_3$ haloalkyl;

$R^3$ is selected from the group consisting of H, halogen, CN, $OR^6$, $N(R^6)_2$, $COOR^6$, $C(O)N(R^6)_2$, $SR^6$, $SO_2R^6$, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and a 3- to 6-membered heterocyclic ring including 1 to 2 ring members selected from the group consisting of O, S, N, and N($R^6$), wherein said $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and 3- to 6-membered heterocyclic ring groups are optionally substituted by one or more substituents independently selected from the group consisting of CN, $OR^6$, $N(R^6)_2$, and $SR^6$, and wherein said $C_3$-$C_6$ cycloalkyl and 3- to 6-membered heterocyclic ring are each further optionally substituted with a member of the group consisting of $C_1$-$C_3$ alkyl and $C_1$-$C_3$ haloalkyl;

optionally $R^3$ and an adjacent A-$R^1$ may be taken together with the atoms to which they are attached form a fused 5- or 6-membered heterocyclic ring including 1 to 2 ring members selected from the group consisting of O, S, N, and N($R^6$) wherein said heterocyclic ring is optionally substituted with or more members of the group consisting of $C_1$-$C_3$ alkyl and $C_1$-$C_3$ haloalkyl;

each $R^6$ is independently selected from the group consisting of H, $C_1$-$C_6$ alkyl, and $C_1$-$C_6$ haloalkyl, wherein said $C_1$-$C_6$ alkyl, and $C_1$-$C_6$ haloalkyl are optionally substituted with OH, O($C_1$-$C_3$ alkyl), and O($C_1$-$C_3$ haloalkyl);

$X^1$ is selected from the group consisting of $CH_2$ and C(O);

$X^2$ is $(C(R^8)_2)_{(1-3)}$;

each $R^8$ is independently selected from the group consisting of H, halogen, CN, $OR^6$, $N(R^6)_2$, $SR^6$, $C_1$-$C_6$ alkyl, $C_1$-$C_6$ haloalkyl, $C_3$-$C_6$ cycloalkyl, and a 3- to 6-membered heterocyclic ring including 1 to 2 ring members selected from the group consisting of O, S, N, and N($R^6$), wherein said $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and 3- to 6-membered heterocyclic ring groups are optionally substituted by one or more substituents independently selected from the group consisting of CN, $OR^6$, $N(R^6)_2$, and $SR^6$, and wherein said $C_3$-$C_6$ cycloalkyl and 3- to 6-membered heterocyclic ring are each further optionally substituted with a member of the group consisting of $C_1$-$C_3$ alkyl and $C_1$-$C_3$ haloalkyl;

optionally 2 $R^8$ on different carbon atoms may be taken together, along with the atoms to which they are attached, to form a 3- to 6-membered fused ring;
optionally 2 $R^8$ on a single carbon atom may be taken together, along with the atom to which they are attached, to form a 3- to 6-membered spirocycle;
$X^3$ is selected from the group consisting of $COOR^6$,

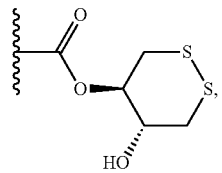

$C(O)SR^6$, $C(S)OR^6$, $SO_2R^6$, and $C(O)N(R^9)_2$; and
each $R^9$ is independently selected from the group consisting of H, $COOR^6$, and $SO_2R^6$.

2. The compound according to claim 1, or a pharmaceutically acceptable salt thereof, wherein

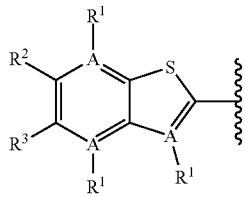

is selected from the group consisting of

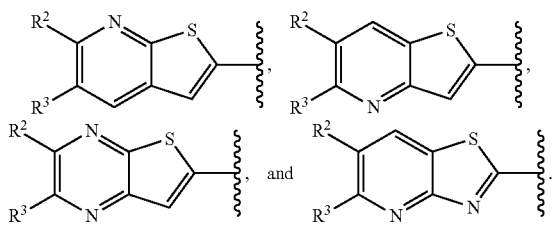

3. The compound according to claim 1, or a pharmaceutically acceptable salt thereof, wherein each $R^1$ is selected independently from the group consisting of H, F, Cl, $C_1$-$C_3$ alkyl, and $C_1$-$C_3$ haloalkyl.

4. The compound according to claim 3, or a pharmaceutically acceptable salt thereof, wherein each $R^1$ is selected independently from the group consisting of H and F.

5. The compound according to claim 1, or a pharmaceutically acceptable salt thereof, wherein $R^2$ is selected from the group consisting of halogen, $C_1$-$C_3$ haloalkyl, $OC_1$-$C_3$ alkyl, $C_2$-$C_3$ alkenyl, and $N(R^6)_2$.

6. The compound according to claim 1, or a pharmaceutically acceptable salt thereof, wherein $R^2$ is selected from the group consisting of Br, Cl, $CH=CH_2$, $OCH_3$, and $N(R^6)_2$.

7. The compound according to claim 1, or a pharmaceutically acceptable salt thereof, wherein $R^3$ is selected from the group consisting of halogen, $C_1$-$C_3$ alkyl, $C_1$-$C_3$ haloalkyl, $OC_1$-$C_3$ alkyl, $C_2$-$C_3$ alkenyl, and $N(R^6)_2$.

8. The compound according to claim 1, or a pharmaceutically acceptable salt thereof, wherein $R^3$ is selected from the group consisting of Br, Cl, $CH_3$, $CH_2CH_3$, $CH=CH_2$, $OCH_3$, and $N(R^6)_2$.

9. The compound according to claim 1, or a pharmaceutically acceptable salt thereof, wherein

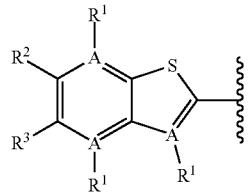

is selected from the group consisting of,

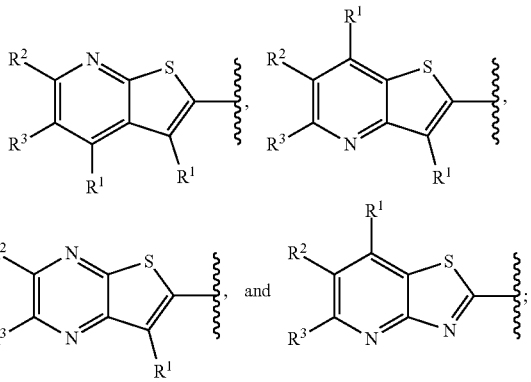

each $R^1$ is selected independently from the group consisting of H, F, Cl, $C_1$-$C_3$ alkyl, and $C_1$-$C_3$ haloalkyl;
$R^2$ is selected from the group consisting of halogen, $C_1$-$C_3$ haloalkyl, $OC_1$-$C_3$ alkyl, $C_2$-$C_3$ alkenyl, and $N(R^6)_2$;
$R^3$ is selected from the group consisting of halogen, $C_1$-$C_3$ alkyl, $C_1$-$C_3$ haloalkyl, $OC_1$-$C_3$ alkyl, $C_2$-$C_3$ alkenyl, and $N(R^6)_2$;
$X^1$-$X^2$-$X^3$ is selected from the group consisting of $C(O)$—$CH_2CHR^8$—$COOR^6$, $C(O)$—$CH_2CHR^8$—$SO_2R^6$, and $C(O)$—$CH_2CHR^8$—$C(O)N(R^9)_2$;
each $R^6$ is independently selected from the group consisting of H, $C_1$-$C_3$ alkyl, and $C_1$-$C_3$ haloalkyl; and
each $R^8$ is selected from the group consisting of H, $C_1$-$C_3$ alkyl, $C_1$-$C_3$ alkyl substituted by OH, $C_1$-$C_3$ alkyl substituted by $OC_1$-$C_3$ alkyl, and $C_3$-$C_6$ cycloalkyl.

10. The compound according to claim 1, or a pharmaceutically acceptable salt thereof, wherein

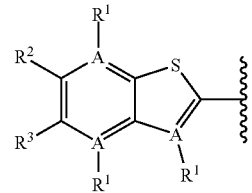

is selected from the group consisting of,

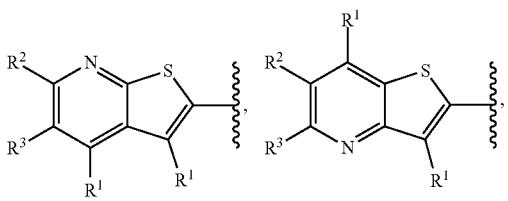

-continued

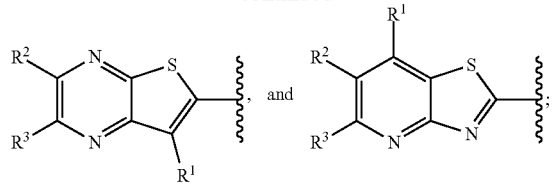

each R¹ is selected from the group consisting of H and F;
R² is selected from the group consisting of Br, Cl, CH=CH₂, OCH₃, and N(R⁶)₂;
R³ is selected from the group consisting of Br, Cl, CH₃, CH₂CH₃, CH=CH₂, OCH₃, and N(R⁶)₂;
X¹-X²-X³ is C(O)—CH₂CHR⁸—COOH;
each R⁶ is independently selected from the group consisting of H and CH₃;
R⁸ is selected from the group consisting of H, CH₃, CH₂CH₃, CH₂CH₂CH₃, CH(CH₃)₂, CH₂OCH₃, and cyclopropyl.

11. The compound according to claim 1, or a pharmaceutically acceptable salt thereof, wherein

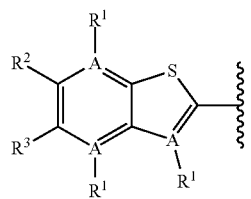

is selected from the group consisting of,

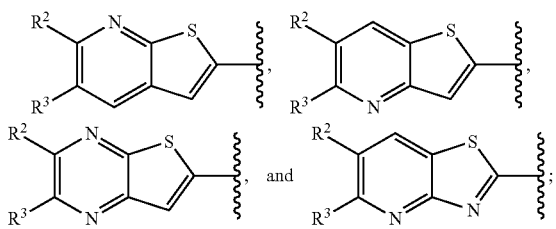

R² is selected from the group consisting of Br, Cl, CH=CH₂, OCH₃, and N(R⁶)₂;
R³ is selected from the group consisting of Br, Cl, CH₃, CH₂CH₃, CH=CH₂, OCH₃, and N(R⁶)₂;
X¹-X²-X³ is C(O)—CH₂CHR⁸—COOH;
each R⁶ is independently selected from the group consisting of H and CH₃;
R⁸ is selected from the group consisting of H, CH₃, CH₂CH₃, CH₂CH₂CH₃, CH(CH₃)₂, CH₂OCH₃, and cyclopropyl.

12. A compound selected from the group consisting of:

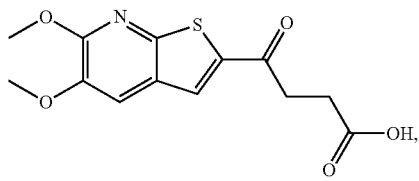

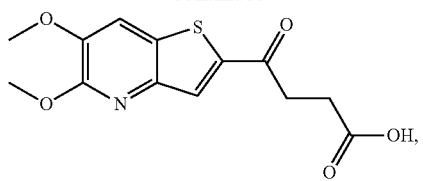

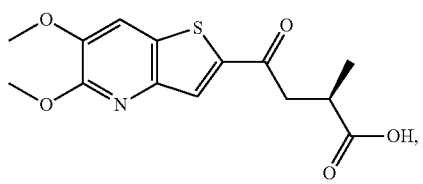

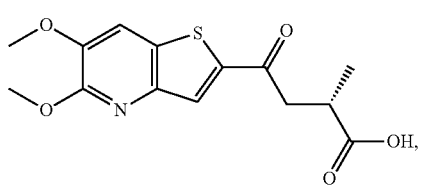

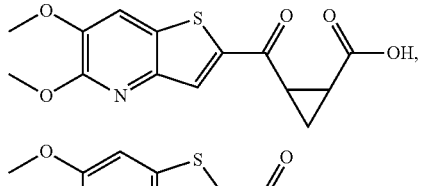

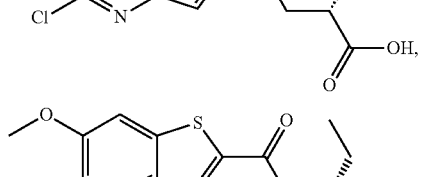

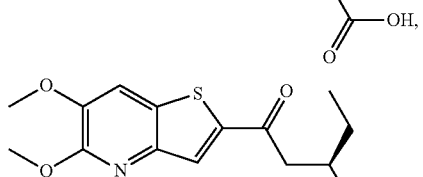

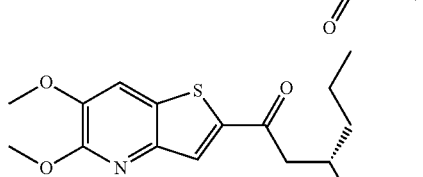

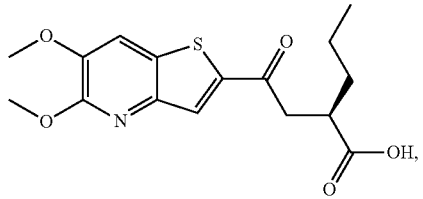

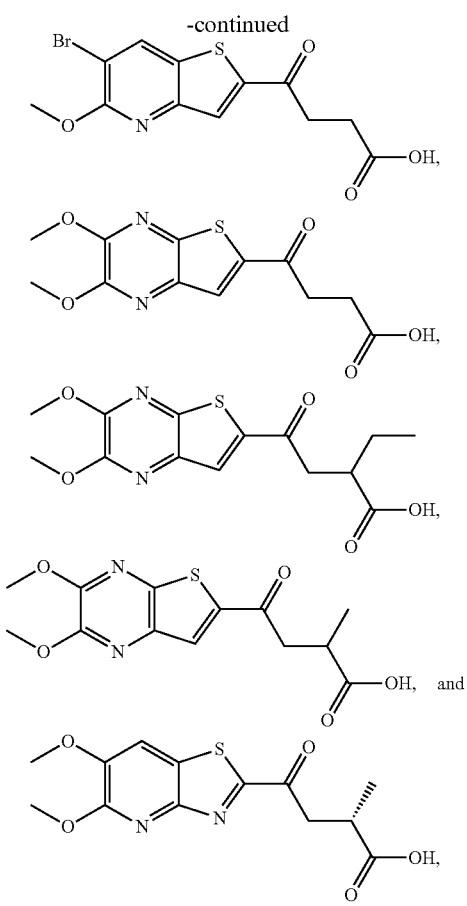

or a pharmaceutically acceptable salt thereof.

13. A pharmaceutical composition, said pharmaceutical composition comprising a compound according to claim 1, or a pharmaceutically acceptable salt thereof, and a pharmaceutically acceptable carrier.

14. A method of inducing an immune response in a patient in need of therapy, said method comprising:
administering a therapeutically effective amount of a compound according to claim 1, or a pharmaceutically acceptable salt thereof, to the patient.

15. A method of inducing an immune response in a patient in need of therapy, said method comprising:
administering a therapeutically effective amount of a pharmaceutical composition according to claim 13 to the patient.

16. A method of inducing STING-dependent type I interferon production in a patient in need of therapy, said method comprising administering a therapeutically effective amount of a compound according to claim 1, or a pharmaceutically acceptable salt thereof, to the patient.

17. A method of inducing STING-dependent type I interferon production in a patient in need of therapy, said method comprising administering a therapeutically effective amount of a pharmaceutical composition according to claim 13 to the patient.

18. A method of treating a cell proliferation disorder in a patient in need of therapy, said method comprising administering a therapeutically effective amount of a compound according claim 1, or a pharmaceutically acceptable salt thereof, to the patient.

19. The method of claim 18, wherein the cell proliferation disorder is cancer.

20. A method of treating a cell proliferation disorder in a patient in need of therapy, said method comprising administering a therapeutically effective amount of a pharmaceutical composition according to claim 13 to the patient.

21. The method of claim 20, wherein the cell proliferation disorder is cancer.

* * * * *